US010987500B2

(12) United States Patent
Fine et al.

(10) Patent No.: US 10,987,500 B2
(45) Date of Patent: Apr. 27, 2021

(54) NANOCHANNELED DEVICE WITH ELECTRODES AND RELATED METHODS

(71) Applicant: The Board of Regents of the University of Texas System, Austin, TX (US)

(72) Inventors: Daniel Fine, Houston, TX (US); Alessandro Grattoni, Houston, TX (US); Mauro Ferrari, Houston, TX (US); Xuewu Liu, Sugar Land, TX (US); Randal Goodall, Austin, TX (US); Sharath Hosali, Austin, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 1901 days.

(21) Appl. No.: 14/449,683

(22) Filed: Aug. 1, 2014

(65) Prior Publication Data
US 2015/0088102 A1 Mar. 26, 2015

Related U.S. Application Data

(60) Provisional application No. 61/861,070, filed on Aug. 1, 2013.

(51) Int. Cl.
*A61M 37/00* (2006.01)
*B81C 1/00* (2006.01)
*A61M 31/00* (2006.01)
*B82Y 5/00* (2011.01)

(52) U.S. Cl.
CPC .......... *A61M 37/00* (2013.01); *A61M 31/002* (2013.01); *B81C 1/00071* (2013.01); *B82Y 5/00* (2013.01); *A61M 2205/04* (2013.01); *B81B 2201/058* (2013.01); *B81B 2203/04* (2013.01)

(58) Field of Classification Search
CPC .............. A61M 37/00; A61M 2205/04; A61M 31/002; A61M 5/14276; B81C 1/00071; B81C 1/00119; B82Y 5/00; B81B 2203/0338; B81B 2203/04; B81B 2201/058; A61K 9/0097; Y10T 137/8593; Y10T 156/1064
See application file for complete search history.

(56) References Cited

U.S. PATENT DOCUMENTS

| | | |
|---|---|---|
| 2005/0023156 A1 | 2/2005 | Ramsey et al. |
| 2006/0093488 A1 | 5/2006 | Wong et al. |
| 2006/0275138 A1* | 12/2006 | Sheng .................... F04B 17/00 417/48 |
| 2007/0066138 A1 | 3/2007 | Ferrari et al. |

(Continued)

OTHER PUBLICATIONS

Fine et al., "A low-voltage electrokinetic nanochannel drug delivery system", *Lab on a Chip*, 11:2526-2534, 2011.

(Continued)

*Primary Examiner* — Lauren P Farrar
*Assistant Examiner* — Hamza A Darb
(74) *Attorney, Agent, or Firm* — Parker Highlander PLLC

(57) ABSTRACT

A nanochannel delivery device and method of manufacturing and use. The nanochannel delivery device comprises an inlet, an outlet, electrodes and a nanochannel. The nanochannel may be oriented parallel to the primary plane of the nanochannel delivery device. The inlet and outlet may be in direct fluid communication with the nanochannel.

28 Claims, 27 Drawing Sheets

(56) References Cited

U.S. PATENT DOCUMENTS

| | | |
|---|---|---|
| 2009/0136948 A1 | 5/2009 | Han et al. |
| 2010/0099136 A1 | 4/2010 | Prabhakarpandian et al. |
| 2010/0152699 A1* | 6/2010 | Ferrari ................. A61K 9/0097 604/500 |
| 2011/0220498 A1 | 9/2011 | Ko et al. |
| 2013/0263946 A1* | 10/2013 | Afzali-Ardakani .... B82Y 15/00 137/561 R |

OTHER PUBLICATIONS

PCT International Search Report and Written Opinion issued in International Application No. PCT/US2014/049404, dated Dec. 16, 2014.
Sih et al., "Characterization of nanochannel delivery membrane systems for the sustained release of resveratrol and atorvastatin: new perspectives on promoting heart health", *Analytical and Bioanalytical Chemistry*, 405(5): 1547-1557, 2012.
Extended European Search Report issued in European Application No. 14832195.3, dated Mar. 15, 2017.

\* cited by examiner

Schematic of the fluorescence microscopy imaging system (A), and release testing apparatus (B).

Cumulative release data of FITC-BSA.

A schematic illustration of the balance between electroosmosis and electrophoresis.

Three-dimensional model of a membrane.

Types of nanochannels, (A) straight nanochannels, (B) perpendicular nanochannels and (C) tilted nanochannels.

Electrodes Layouts

Testing device. (a) nDS2 membrane, (b) epoxy glue, (c) basket, (d) cell culture well.

Wires bonded on the nDS2 electrodes

Assembled basket. The nDS2 membrane is shown embedded in the epoxy glue (amber color)

Bubble motion caused by the electroosmotic transport of PBS.

Effect of the nanochannel size over BSA-FITC release throughout nDS2#3.

Effect of electrodes configuration on the BSA-FITC release throughout nDS2 SO#3 and nDS2 SO#4

Effect of the applied voltage on the BSA-FITC release throughout nDS2 150#7

Effect of the nanochannel size over BSA-FITC release throughout nDS2#3

NANOCHANNELED DEVICE WITH ELECTRODES AND RELATED METHODS

CROSS-REFERENCE TO RELATED APPLICATIONS

This application claims priority to U.S. Provisional Patent Application Ser. No. 61/861,070, filed Aug. 1, 2013, the contents of which are incorporated by reference herein.

This invention was made with government support under grants NNJ06HE06A and NNX08AW91G from NASA and DODW81XWH-09-1-0212 from the Department of Defense. The government has certain rights in the invention.

BACKGROUND INFORMATION

Considerable advances have been made in the field of therapeutic agent (e.g. drug) delivery technology over the last three decades, resulting in many breakthroughs in clinical medicine. The creation of therapeutic agent delivery devices that are capable of delivering therapeutic agents in controlled ways is still a challenge. One of the major requirements for an implantable drug delivery device is controlled release of therapeutic agents, ranging from small drug molecules to larger biological molecules. It is particularly desirable to achieve a continuous passive drug release profile consistent with zero order kinetics whereby the concentration of drug in the bloodstream remains constant throughout an extended delivery period.

These devices have the potential to improve therapeutic efficacy, diminish potentially life-threatening side effects, improve patient compliance, minimize the intervention of healthcare personnel, reduce the duration of hospital stays, and decrease the diversion of regulated drugs to abusive uses.

Nanochannel delivery devices may be used in drug delivery products for the effective administration of drugs. In addition, nanochannel delivery devices can be used in other applications where controlled release of a substance over time is needed.

While several implantable passive drug delivery devices have been designed for the constant administration of therapeutics, the lack of mechanisms for the continuous regulation of the release of drug from these devices is a limiting factor for their usage. The ability of actively control the administration rate of therapeutics from implanted devices would allow employing such systems for therapies which requires non-constant drug administration such as chronotherapy. In some cases cyclic drug administration can enhance the therapeutic efficacy of treatments. The study of chronobiology indeed, demonstrated the rhythmicity in the pathophysiology of diseases. In other words, the therapeutic efficacy of drugs was shown to be strongly dependent on the administration schedule. Non-constant drug administration from passive release implantable systems requires the development of simple and safe devices for the remote activation and deactivation and fine tuning of the drug release.

Recent work has elucidated the potential of important new therapeutic paradigms, including metronomic delivery and chronotherapy, in which the precise timing and location of therapeutic administration has a significant impact on efficacy and toxicity. New drug delivery architectures are needed to not only release drug continuously at precise rates, but also synchronize their release with circadian cycles.

Conventional systemically administered chemotherapy often relies on a dosing regimen in which cytotoxic drugs are delivered at the maximum tolerable dose (MTD) either once or infused for a finite duration followed by a 2-3 week recovery period [31]. The recovery period is needed to allow patients to overcome the side effects associated with this mode of administration. New delivery regimes, including metronomic delivery [31, 32] and chronotherapy [33, 34], demonstrated in pre-clinical trials that by adjusting the timing and/or frequency of delivery, the required dose can be scaled back from the MTD with a subsequent reduction in adverse side effects while maintaining or even increasing therapeutic efficacy [31, 33]. In metronomic delivery a lower dose than the MTD is administrated at short time increments without requiring a recovery period [31] whereas in chronotherapy delivery is synchronized to natural circadian cycles [34].

To realize the full potential of these new delivery paradigms a host of new delivery vehicles have been developed. Implants passively controlled by silicon based nanofluidic membranes have already been demonstrated both in vitro and in vivo to be capable of sustained concentration-independent constant and reproducible drug release, the goal of metronomic delivery [35-37]. Such passive release membranes are precisely fabricated, mechanically robust, and capable of clinically appropriate delivery rates comparable to other delivery modalities without the necessity of moving parts. However, the synchronization of chronotherapy further requires active control.

To date, a number of actively controlled drug delivery architectures have appeared in the literature. Preprogrammed pulsatile delivery has been realized both in vitro and in vivo from silicon microchips possessing reservoirs capped with thin gold membranes that can be electrically ruptured and individually addressed [38-39]. As pulsatile delivery is limited to releasing discrete quantities of drug, however, electrokinetic actuation has also been investigated.

The direct electrokinetic control of nanofluidic channels has been achieved by the application of longitudinal and/or transverse electric fields [40-50] in nanochannels with critical dimensions as small as 2 nm [51]. Such devices have been investigated as preconcentrators [52-55] and separators [56, 57] for a host of diagnostic techniques, for single molecule manipulation [58-61], and for their potential in drug delivery applications [62]. Electroosmotic-pump-based delivery devices utilize a separate electroosmotic pumping compartment to exert pressure on a piston or diaphragm to exude drug from a second drug containing compartment [63, 64]. These devices, typically implemented with glass frits or track etched polymer membranes [65], have been shown to be switchable and capable of continuous release. However, such a system requires a large implant volume to house a sealed pumping compartment, which places additional limitations on the geometry of the implant. Electrophoretic devices for sample processing [66] and drug delivery [67] benefit from the lack of a net bulk fluid flow that increases ambient pressure gradients but have historically required high power. In electroosmosis such pressure gradients, potential limitations to sustained release of molecules, must include complex implant designs.

Several implantable passive drug delivery devices have been designed for the constant administration of therapeutics [34]. However, the lack of a mechanism for the continuous regulation of the release of drug from these devices is a limiting factor for their usage. The ability of actively control the administration rate of therapeutics from implanted devices would allow employing such systems for therapies which requires non-constant drug administration such as chronotherapy. In some cases cyclic drug administration can enhance the therapeutic efficacy of treatments. The study of chronobiology indeed, demonstrated the rhythmicity in the pathophysiology of diseases [35]. In other words the therapeutic efficacy of drugs was shown to be strongly dependent on the administration schedule. Non-constant drug administration from passive release implantable systems requires the development of simple and safe devices for the remote activation and deactivation and fine tuning of the drug release.

Micro- and nanofabrication has enabled the production of fluidic channels with dimensions sufficient to study and exploit a range of transport phenomena, including zero-order passive diffusion [1], field effect flow control [2, 3], surface dominated conduction [2, 4], entropic trapping [5], and concentration polarization [2, 7, 8, 9, 10], that are unique to fluids confined at the nanoscale. Most of these phenomena are in some way related to how counter ions accumulate and then arrange themselves at the interface between the solution and the nanochannel wall in order to screen the surface charge, a structure referred to as the electrical double layer (EDL) [11]. Controlling how analytes interact with the EDL has been demonstrated to be useful for such applications as drug delivery [12], molecular sieving [13, 14], controlling hydrogen diffusion in fuel cells [15], and preconcentration of biological samples [16].

Previously reported silicon-based nanochannel membranes are mechanically robust with hundreds of thousands of nanofabricated monodispersed parallel slit nanochannels as small as 3 nm [13, 14]. This membrane architecture has been incorporated into implantable drug reservoirs for the zero-order release of pharmaceutical agents at clinically relevant release rates over extended durations both in vitro and in vivo. The nanochannel monodispersity is of crucial importance as zero-order passive release relies on a definite relationship between the effective nanochannel height (physical height plus any electrostatic interactions between the walls and charged analytes) and the size of the diffusing analyte [17, 19]. It would be desirable, however, to enable release rate modulation from these passive diffusion devices for such applications as chronotherapy [20]. Chronotherapy represents a dosing regimen in which the delivery of pharmaceutical agents is synchronized to natural circadian cycles and has been shown to increase therapeutic efficacy for a range of pathological conditions [21, 22]. In this context, we have previously demonstrated electrokinetic release modulation using electrophoresis as the primary mode of temporal control [17]. These electrophoretically controlled prototypes, derived from an earlier generation of much slower releasing 100 nm nanochannel membranes with embedded platinum electrodes, demonstrated a 10× increase in release rate at an applied potential of 2V. Other alternative implantable and transdermal electrokinetic and electromagnetic approaches have also been developed based on electroosmotic pumps [23], galvanic cells, magnetic resonance [24], and iontophoresis [25] to name a few.

Concentration polarization is defined by the accumulation and depletion of charged analytes at the inlets and outlets of nanochannels upon the application of an electric field [8, 9, 10, 26 and 27]. These accumulation and depletion regions result from electrostatic interactions that reject co-ions of the same polarity while accumulating counter-ions of opposite polarity to the inherent surface charge on the nanochannel walls, while still maintaining charge neutrality in the bulk solution. Within the depletion regions, the Debye length increases leading to further limitations to translocation of co-ions through the nanochannel [26, 28]. This phenomenon has previously been used for the preconcentration of analytes prior to molecular detection [29]. It has also proven to be useful for the separation of complex mixtures through the adjustment of pH around the isoelectric points of the constituents, even at moderate ionic strength when the Debye length is relatively short [28].

This disclosure reports the modification of fast releasing nanochannel delivery system membranes to enable electrokinetically modulated drug release. The analyte of choice, dendritic fullerene 1 (DF-1), was selected because of its high valence charge, −10.4 at a pH of 7.4, to maximize the analyte response to applied potentials in high ionic strength solutions that better simulate the in vivo environment, as well as its potential use as a free radical scavenger and carrier molecule for MRI contrast agents [30]. In the case of these smaller nanochannel devices, however, the application of 1.5 V resulted in a decrease in release rate regardless of the polarity of the applied voltage instead of the increase seen with the previous generation of 100 nm membranes. Depending on the separation distance between the platinum electrodes (~1 mm for the electron beam deposited thin films), this downward release rate modulation could be as much as two orders of magnitude. Such a result is inconsistent with both electrophoresis and electroosmosis. The sealed UV-based testing apparatus further ruled out electroosmosis because of the associated pressure gradients that would be expected to build quickly in opposition to the bulk fluid flow in such a closed system. The Debye length adjustment seen in concentration polarization therefore represents a potential explanation for the observed release dynamics with parallels from earlier experiments that used changes to ionic strength to modulate DF-1 release [20]. Similar to the zero-order kinetics achieved with the passive release membranes, the definite relationship between analyte size and nanochannel height would also have to be maintained for the Debye length adjustments observed in concentration polarization to dramatically affect analyte release as has been demonstrated here, especially in the high ionic strength environment present in vivo where the Debye length is expected to be on the order of several nanometers or less.

SUMMARY

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The term "inlet microchannel" is defined as a microchannel through which a molecule travels prior to entering a nanochannel in a nanochanneled delivery device.

The term "outlet microchannel" is defined as a microchannel through which a molecule travels immediately prior to exiting a nanochanneled delivery device.

The term "nanochannel" is defined as a channel with a cross-section having at least one dimension (e.g. height, width, diameter, etc.) that is less than 200 nm.

The term "macrochannel" is defined as a channel with a cross-section having a maximum dimension (e.g. height, width, diameter, etc.) that is greater than about 10 µm.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

Exemplary embodiments of the present disclosure comprise an actively controlled nanofluidic membrane that exploits electrophoresis to control the magnitude, duration, and timing of drug release. In exemplary embodiments, the membrane, produced using high precision silicon fabrication techniques, has platinum electrodes integrated at the inlet and outlet that allow both amplification and reversal of analyte delivery with low applied voltage (at or below 2 VDC). Device operation was demonstrated with a solution of fluorescein isothiocyanate conjugated bovine serum albumin using fluorescence spectroscopy and microscopy and has been characterized for long-term molecular release and release reversibility. Through a combination of theoretical and experimental analysis, the relative contributions of electrophoresis and electroosmosis have been determined. The membrane's clinically relevant electrophoretic release rate at 2 VDC exceeds the passive release by nearly one order of magnitude, demonstrating the potential to realize the therapeutic paradigm goal.

Exemplary embodiments comprise an implantable and mechanically robust nanofluidic membrane with integrated platinum electrodes at the inlet and outlet. This electrokinetically actuated nanofluidic membrane, the nanochannel Delivery System (NDS), is manufactured using highly precise silicon nanofabrication techniques. Such a design enables the electrophoretic transport of analytes through its nanofluidic channels at low applied voltage with minimal electrolysis. We employed florescence spectroscopy to measure the membrane release characteristics of bovine serum albumin conjugated with fluorescein isothiocyanate (FITC-BSA) over a period of 30 days and fluorescence microscopy to visualize the dynamics of FITC-BSA in the micro- and nanochannels. The electrophoretic transport was fully reversible and capable of increasing the release rate by over 9 times as compared to a concentration-driven transport enabling release rates of clinical relevance [35]. Certain embodiments include a nanochannel delivery device comprising: an inlet microchannel; a nanochannel; an outlet microchannel; a first electrode; and a second electrode, where the inlet microchannel and the outlet microchannel are in direct fluid communication with the nanochannel, and where the first electrode is directly coupled to a first surface of the nanochannel delivery device. In specific embodiments, the second electrode is directly coupled to a second surface of the nanochannel delivery device. In certain embodiments, the first electrode comprises electrically-conductive material deposited on the first surface and the second electrode comprises electrically-conductive material deposited on the second surface. In particular embodiments, the second surface is a surface of the inlet microchannel, the outlet microchannel, or the nanochannel. In some embodiments, the first surface is a surface of the inlet microchannel, the outlet microchannel, or the nanochannel. In specific embodiments, the nanochannel delivery device is configured to control a diffusion rate of molecules passing through the nanochannel by application of a voltage between the first and second electrodes. In certain embodiments, the nanochannel is oriented parallel to the primary plane of the nanochannel delivery device. In particular embodiments, a flow path from the inlet microchannel to the nanochannel to the outlet microchannel requires a maximum of two changes in direction.

In some embodiments, the inlet microchannel has a length, a width, and a depth; the outlet microchannel has a length, a width, and a depth; the nanochannel has a length, a width, and a depth; the ratio of the nanochannel length to the inlet microchannel length is between 0.01 and 50.0; and the ratio of the nanochannel length to the outlet microchannel length is between 0.01 and 10.0. In particular embodiments, the inlet microchannel is in direct fluid communication with the outlet microchannel via a single nanochannel.

Some embodiments include a nanochannel delivery device comprising: an inlet microchannel; a nanochannel; an outlet microchannel; a first electrode; a second electrode; and a fluid flow path from the inlet microchannel to the outlet microchannel, where the fluid flow path requires a maximum of two changes in direction, and the first electrode is directly coupled to a first surface of the nanochannel delivery device. In particular embodiments, the second electrode is directly coupled to a second surface of the nanochannel delivery device. In some embodiments, the first electrode comprises electrically-conductive material deposited on the first surface and the second electrode comprises electrically-conductive material deposited on the second surface. In specific embodiments, the second surface is a surface of the inlet microchannel, the outlet microchannel, or the nanochannel. In certain embodiments, the first surface is a surface of the inlet microchannel, the outlet microchannel, or the nanochannel. In particular embodiments, the nanochannel delivery device is configured to control a diffusion rate of molecules passing through the nanochannel by application of a voltage to the first and second electrodes. In some embodiments, the nanochannel is oriented parallel to the primary plane of the nanochannel delivery device. In specific embodiments, the inlet microchannel and the outlet microchannel are in direct fluid communication with the nanochannel.

Certain embodiments include a nanochannel delivery comprising: a substantially planar body comprising a first surface and a second surface opposing the first surface; a nanochannel disposed within the substantially planar body; a first electrode; a second electrode; an inlet microchannel in fluid communication with the nanochannel; an outlet microchannel in fluid communication with the nanochannel, where the inlet microchannel extends from the nanochannel to the first surface and where the outlet microchannel extends from the nanochannel to second surface; and a fluid flow path from the inlet microchannel to the outlet microchannel, where the fluid flow path requires a maximum of two changes in direction, and where the first electrode is directly coupled to a first surface of the nanochannel delivery device.

In particular embodiments, the second electrode is directly coupled to a second surface of the nanochannel delivery device. In certain embodiments, the first electrode comprises electrically-conductive material deposited on the first surface and the second electrode comprises electrically-conductive material deposited on the second surface. In particular embodiments, the second surface is a surface of the inlet microchannel, the outlet microchannel, or the nanochannel. In some embodiments, the first surface is a surface of the inlet microchannel, the outlet microchannel, or the nanochannel. In specific embodiments, the nanochannel delivery device is configured to control a diffusion rate of molecules passing through the nanochannel by application of a voltage to the first and second electrodes. In certain embodiments, the first electrode is directly coupled to a first surface proximal to a first end the fluid flow path, and wherein the second electrode is directly coupled to a second surface proximal to a second end the fluid flow path.

Particular embodiments include a nanochannel delivery device comprising: a plurality of inlet microchannels; a first electrode; a second electrode; a plurality of nanochannels; and a plurality of outlet microchannels, where each inlet microchannel is in direct fluid communication with an outlet microchannel via a single nanochannel, and where the first electrode is directly coupled to a first surface of the nanochannel delivery device. In some embodiments, the second electrode is directly coupled to a second surface of the nanochannel delivery device. In certain embodiments, the second surface is a surface of a first inlet microchannel of the plurality of inlet microchannels, a first outlet microchannel of the plurality of outlet microchannels, or a first nanochannel of the plurality of nanochannels. In particular embodiments, the first surface is a surface of the first inlet microchannel, the first outlet microchannel, or the first nanochannel. In some embodiments, the nanochannel delivery device is configured to control a diffusion rate of molecules passing through the first nanochannel by application of a voltage to the first and second electrodes. In specific embodiments, the nanochannel delivery device comprises a second nanochannel of the plurality of nanochannels, and wherein application of the voltage to the first and second electrodes does not control a diffusion rate of molecules passing through the second nanochannel. In certain embodiments, the first electrode comprises electrically-conductive material deposited on the first surface and the second electrode comprises electrically-conductive material deposited on the second surface. In particular embodiments, the nanochannel is oriented parallel to the primary plane of the nanochannel delivery device. In some embodiments, an inlet microchannel of the plurality of inlet microchannels and an outlet microchannel of the plurality of outlet microchannels are in direct fluid communication with a common nanochannel of the plurality of nanochannels. In specific embodiments, individual inlet and outlet microchannels are arranged perpendicular to a primary plane of the nanochannel delivery device; the plurality of inlet microchannels form a first array; the plurality of outlet microchannels form a second array; and the first array the second array are overlapping so that individual inlet microchannels are distributed between individual outlet microchannels when viewed along a section taken perpendicular to the primary plane.

Certain embodiments include a nanochannel delivery device comprising: a substantially planar body including: a length, a width, and a thickness, where the length and the width are each greater than the thickness; an inlet surface on a first side of the substantially planar body, where the inlet surface is bounded by the length and the width of the substantially planar body; an outlet surface on a second side of the substantially planar body, where the outlet surface is bounded by the length and the width of the substantially planar body, and where the inlet surface is substantially parallel with the outlet surface; a first electrode; a second electrode; a nanochannel disposed within the substantially planar body, where the nanochannel comprises an inlet end and an outlet end; an inlet microchannel in fluid communication with the nanochannel; and an outlet microchannel in fluid communication with the nanochannel, where the inlet microchannel and nanochannel are configured such that a first linear axis can extend between the inlet surface and the inlet end of the nanochannel, and where the first electrode is directly coupled to a first surface of the nanochannel delivery device.

In some embodiments, the second electrode is directly coupled to a second surface of the nanochannel delivery device. In specific embodiments, the first electrode comprises electrically-conductive material deposited on the first surface and the second electrode comprises electrically-conductive material deposited on the second surface. In certain embodiments, the second surface is a surface of the inlet microchannel, the outlet microchannel, or the nanochannel. In particular embodiments, the first surface is a surface of the inlet microchannel, the outlet microchannel, or the nanochannel. In some embodiments, the nanochannel delivery device is configured to control a diffusion rate of molecules passing through the nanochannel by application of a voltage to the first and second electrodes. In specific embodiments, the outlet microchannel and nanochannel are configured such that a second linear axis can extend between the outlet surface and the outlet end of the nanochannel. In certain embodiments, a primary axis of the inlet microchannel is perpendicular to a plane that is parallel to the substantially planar body. Particular embodiments further comprise an inlet macrochannel between the inlet surface the inlet microchannel, wherein the inlet macrochannel comprises boundary walls that are generally perpendicular to the inlet surface. In some embodiments, the inlet macrochannel is formed by deep reactive-ion etching. In specific embodiments, a primary axis of the outlet microchannel is perpendicular to a plane that is parallel to the substantially planar body.

Certain embodiments include an apparatus comprising a first nanochannel delivery device as disclosed herein inserted into a capsule. In particular embodiments, the first nanochannel delivery device is installed perpendicular to the primary axis of the capsule. In some embodiments, the capsule shape is a disc or oval with thickness less than any diametric measure of the capsule. In specific embodiments, the first nanochannel delivery device is installed in the primary plane of the capsule. In certain embodiments, the capsule comprises a septum. In certain embodiments, the septum comprises a self-sealing material. In particular embodiments, the septum comprises silicone rubber. In some embodiments, the septum is configured to receive an injection of a therapeutic agent. Specific embodiments further comprise a cap covering the septum. In certain embodiments, the cap comprises an orifice configured to guide a needle towards the septum. In particular embodiments, the capsule comprises a cover extending over the first nanochannel delivery device. In some embodiments, the cover comprises one or more orifices. In specific embodiments, the one or more orifices are sized so that they do not limit diffusion of a therapeutic agent from the capsule during use.

In certain embodiments, the cover is configured to protect the first nanochannel delivery device from mechanical damage. In particular embodiments, the cover is configured to protect the first nanochannel delivery device from incursion by biological tissue structures after the capsule has been implanted in a living body. In some embodiments, the capsule comprises a first inner reservoir. In specific embodiments, the first nanochannel delivery device is in fluid communication with the first inner reservoir. In certain embodiments, the capsule comprises a second inner reservoir in fluid communication with a second nanochannel delivery device. In particular embodiments, the first and second inner reservoir are not in fluid communication with each other. In some embodiments, the first and second inner reservoirs are separated by a wall. In specific embodiments, the first inner reservoir contains a first therapeutic agent and the second inner reservoir comprises a second therapeutic agent. In certain embodiments, the first nanochannel delivery is configured to diffuse a first therapeutic agent at a first diffusion rate and wherein the second nanochannel delivery device is configured to diffuse the second therapeutic agent a second diffusion rate. In particular embodiments, the volume of the first inner reservoir can be modified by replacing a first removable component of the capsule with a larger removable component. In some embodiments, the first inner reservoir comprises a coating compatible with a therapeutic substance. In specific embodiments, the capsule comprises an outer coating configured to prevent deleterious tissue encapsulation. In certain embodiments, the capsule comprises a cylindrical shape. In particular embodiments, the capsule comprises a disc shape. In some embodiments, the capsule comprises a rectangular surface and an arched surface. In specific embodiments, the capsule comprises a uniform cross-section. In certain embodiments, the capsule comprises one or more of the following materials: stainless steel, titanium, polyetheretherkeytone, polysulfone, epoxy, silicone rubber, polyetherketoneketone, and thermoplastic polyurethane.

In particular embodiments, the capsule comprises an anchor member. In some embodiments, the anchor member is configured to receive a suture. In specific embodiments, the capsule comprises a color coding to indicate a characteristic of the capsule or the nanochannel delivery device. In certain embodiments, the color coding indicates a characteristic of a therapeutic agent contained within the capsule. In particular embodiments, the capsule comprises a translucent or transparent cover extending over the first nanochannel delivery device.

Certain embodiments include a method of fabricating a nanochannel delivery device, where the method comprises: providing a first substrate; forming a plurality of nanochannels in the first substrate; forming a plurality of inlet microchannels in the nanochannels of the first substrate; providing a first electrode directly coupled to an inlet microchannel; providing a second substrate; forming a plurality of outlet microchannels in the second substrate; providing a second electrode directly coupled to an outlet microchannel; and coupling the second substrate to the first substrate, where each inlet microchannel is in direct fluid communication with a nanochannel.

In particular embodiments, the first substrate comprises a silicon-on-insulator wafer. In some embodiments, the height of each nanochannel is between approximately two nanometers and two hundred and fifty nanometers. In specific embodiments, the height of each nanochannel is between approximately one and five hundred nanometers. In certain embodiments, the second substrate comprises a sacrificial release layer of indium tin oxide film on silicon. Particular embodiments further comprise depositing a glass film on the second substrate prior to forming the plurality of inlet microchannels in the second substrate. In some embodiments, the second substrate comprises a glass wafer; and the glass wafer is bonded to the first substrate and the glass wafer is ground to reduce the thickness prior to forming the plurality of outlet microchannels.

Specific embodiments include a method of fabricating a nanochannel delivery device, where the method comprises: providing first substrate; directly coupling a first electrode to the first substrate; forming a plurality of inlet microchannels in the first substrate; filling in the plurality of inlet microchannels with a first sacrificial material; forming a plurality of nanochannels on the first substrate; filling in the plurality of nanochannels with a second sacrificial material forming a capping layer that covers the plurality of nanochannels; forming a plurality of outlet microchannels in the capping layer; directly coupling a second electrode to the capping layer; removing the second sacrificial material from the plurality of nanochannels; and removing the first sacrificial material from the plurality of inlet microchannels.

In certain embodiments, an inlet microchannel is arranged perpendicular to a primary plane of the first substrate. In particular embodiments, an outlet microchannel is arranged perpendicular to a primary plane of the first substrate. In some embodiments, an inlet microchannel is in direct fluid communication with a nanochannel. In specific embodiments, an outlet microchannel is in direct fluid communication with a nanochannel. In certain embodiments, the first substrate comprises a silicon-on-insulator wafer comprising an internal oxide layer. In particular embodiments, the inlet and outlet microchannels are patterned using a photolithography process. In some embodiments, forming the plurality of inlet microchannels comprises etching material from the first substrate, and wherein the etching is terminated at the internal oxide layer. In specific embodiments, forming a plurality of inlet macrochannels comprises etching material from a back side of the first substrate, and wherein the etching is terminated at the internal oxide layer. In certain embodiments, the removal of the internal oxide layer after etching material to form the inlet microchannel and inlet macrochannels opens a pathway between the inlet microchannels and inlet macrochannels. In some embodiments, each nanochannel is between approximately one and ten nanometers deep. In specific embodiments, each nanochannel is between approximately ten and twenty nanometers deep. In certain embodiments, each nanochannel is between approximately twenty and thirty nanometers deep. In particular embodiments, each nanochannel is between approximately thirty and forty nanometers deep. In some embodiments, each nanochannel is between approximately forty and two hundred and fifty nanometers deep.

In specific embodiments, the first sacrificial material can be subsequently removed by selective etching. In some embodiments, the first sacrificial material is selected from the group consisting of: tungsten, copper, doped glass, and undoped glass. In specific embodiments, the first sacrificial material is filled into the plurality of inlet microchannels so that the second sacrificial material extends above the top of the inlet microchannels and is planarized by chemical-mechanical planarization (CMP). In certain embodiments, the second sacrificial material is tungsten, titanium nitride, aluminum, titanium tungsten, or nickel. In particular embodiments, the second sacrificial material can be subsequently removed by selective etching. In certain embodiments, the capping layer is selected from silicon nitride, silicon oxide, silicon carbonitride, silicon carbide, and silicon. In some embodiments, the capping layer comprises multiple depositions of materials comprising tensile and compressive stresses such that the net capping layer stress is tensile. In specific embodiments, the capping layer is between approximately 0.5 and 1.0 microns thick. In certain embodiments, the capping layer is between approximately 1.0 and 2.0 microns thick. In particular embodiments, the capping layer is between approximately 2.0 and 4.0 microns thick. In certain embodiments, the capping layer is between approximately 4.0 and 10.0 microns thick. In particular embodiments, the capping layer is greater than 10.0 microns thick.

Specific embodiments include a method of fabricating a nanochannel delivery device, where the method comprises: providing a first substrate; forming a plurality of nanochannels on a first side of the first substrate; filling in the plurality of nanochannels with a sacrificial material; coupling an initial capping layer to the first side of the first substrate; forming a plurality of inlet microchannels in the capping layer; preparing a second substrate with a bonding layer; directly coupling a first electrode to the first substrate; directly coupling a second electrode to the second substrate; coupling the second substrate to a second side of the first substrate; removing a first portion of the second substrate; providing an additional capping layer to the second substrate; forming a plurality of outlet microchannels in the second substrate; and removing the sacrificial material to open the plurality of nanochannels.

In certain embodiments, the second substrate comprises a release layer, and wherein the release layer can be selectively removed to cause separation of the second substrate from the first substrate. In particular embodiments, an outlet microchannel is in direct fluid communication with a nanochannel. In some embodiments, the first substrate comprises a silicon-on-insulator wafer comprising an internal layer, which can be for example, a dielectric or metal layer. In specific embodiments, forming the plurality of inlet microchannels comprises etching material from the capping layer, and the etching is terminated at the internal layer. In certain embodiments, forming a plurality of inlet macrochannels comprises etching material from a back side of the first substrate, and the etching is terminated at the internal layer. In particular embodiments, the removal of the internal layer after etching material to form the inlet microchannel and inlet macrochannels opens a pathway between the inlet microchannels and inlet macrochannels. In some embodiments, each nanochannel is between approximately one and ten nanometers deep. In specific embodiments, each nanochannel is between approximately ten and twenty nanometers deep. In certain embodiments, each nanochannel is between approximately twenty and thirty nanometers deep. In particular embodiments, each nanochannel is between approximately thirty and forty nanometers deep. In some embodiments, each nanochannel is between approximately forty and two hundred nanometers deep. In specific embodiments, the sacrificial material can be subsequently removed by selective etching. In certain embodiments, the sacrificial material is tungsten, titanium nitride, aluminum, titanium tungsten, or nickel. In particular embodiments, the initial capping layer is silicon nitride deposited by plasma enhanced chemical vapor deposition. In some embodiments, the initial capping layer is between approximately 0.01 and 0.5 microns thick. In specific embodiments, the initial capping layer is between approximately 0.5 and 1.0 microns thick. In certain embodiments, the initial capping layer is between approximately 1.0 and 2.0 microns thick. In particular embodiments, the initial capping layer is between approximately 2.0 and 4.0 microns thick. In some embodiments, the initial capping layer is between approximately 4.0 and 10.0 microns thick. In specific embodiments, the initial capping layer is greater than 10.0 microns thick. In particular embodiments, the initial capping layer is selected from silicon nitride, silicon oxide, silicon carbonitride, silicon carbide, and silicon. In some embodiments, the initial capping layer comprises multiple depositions of materials comprising tensile and compressive stresses such that the net capping layer stress is tensile. In specific embodiments, the bonding layer is selected from the group consisting of benzocyclobutene, silicon oxide, copper, doped glass, gold and gold alloys. In certain embodiments, the method of coupling the second substrate to the first substrate is selected from the group consisting of anodic bonding, fusion bonding, and thermocompression bonding.

Particular embodiments include a nanochannel delivery device comprising: a plurality of inlet microchannels, where each of the inlet microchannels has a length, a width, and a depth, and where the inlet microchannel length is greater than the inlet microchannel width and depth; a first electrode; a second electrode; a plurality of outlet microchannels, wherein each of the outlet microchannels has a length, a width, and a depth; a plurality of nanochannels in fluid communication with the plurality of inlet microchannels and outlet microchannels, where the plurality of inlet microchannels are arranged so that the inlet microchannel width and depth define a first plane that is parallel to the primary plane of the nanochannel delivery device; and where the plurality of outlet microchannels are arranged so that the outlet microchannel width and depth define a second plane that is parallel to the primary plane of the nanochannel delivery device, wherein the first electrode is directly coupled to a first surface of the nanochannel delivery device.

In some embodiments, the second electrode is directly coupled to a second surface of the nanochannel delivery device. In specific embodiments, the first electrode comprises electrically-conductive material deposited on the first surface and the second electrode comprises electrically-conductive material deposited on the second surface. In certain embodiments, the second surface is a surface of the inlet microchannel, the outlet microchannel, or the nanochannel. In particular embodiments, the first surface is a surface of the inlet microchannel, the outlet microchannel, or the nanochannel. In some embodiments, the nanochannel delivery device is configured to control a diffusion rate of molecules passing through a nanochannel by application of a voltage to the first and second electrodes.

Certain embodiments include a nanochannel delivery device comprising: an inlet channel; an outlet channel; and a nanochannel in fluid communication with the inlet channel and the outlet channel, where the nanochannel comprises a first surface and a second surface, wherein the first surface is substantially parallel to the second surface; and where the first surface and the second surface are electrically conductive. In particular embodiments, the nanochannel delivery device is configured to control a diffusion rate of molecules passing through the nanochannel by application of a voltage to the first and second surfaces. In some embodiments, the first surface is electrically coupled to the second surface. In specific embodiments, the first and second surfaces of the nanochannel are separated by a distance that is less than 500 nm. In certain embodiments, the first and second surfaces of the nanochannel are separated by a distance that is less than 100 nm. In particular embodiments, the first and second surfaces of the nanochannel are separated by a distance that is less than 50 nm. In some embodiments, the first and second surfaces of the nanochannel form a first electrode; the nanochannel delivery device comprises a second electrode; and at least one of the inlet channel and the outlet channel is between the nanochannel and the second electrode.

In certain embodiments, the first and second surfaces of the nanochannel are electrically coupled via a third surface extending substantially perpendicular to the first and second surfaces of the nanochannel. In particular embodiments, during operation a voltage can be applied to the first and second surfaces and movement of a fluid through the nanochannel can be controlled by varying the voltage. In some embodiments, the nanochannel is in direct fluid communication with the first and second microchannels.

Certain embodiments include a nanochannel delivery comprising: a first exterior surface and a second exterior surface; a first electrode and a second electrode; a nanochannel; a first microchannel in fluid communication with the nanochannel; and a second microchannel in fluid communication with the nanochannel, where the first microchannel extends from the nanochannel to the first exterior surface; where the second microchannel extends from the nanochannel to the second exterior surface; and where the first and second electrodes extend from the nanochannel to the first exterior surface. In particular embodiments, the first electrode is directly coupled to a first surface of the nanochannel. In some embodiments, the second electrode is directly coupled to a second surface of the nanochannel. In specific embodiments, the first electrode is directly coupled to a first end of the nanochannel proximal to the first microchannel. In certain embodiments, the second electrode is directly coupled to a second end of the nanochannel proximal to the second microchannel. In particular embodiments, nanochannel delivery device is configured to control a diffusion rate of molecules passing through the nanochannel by application of a voltage to the first and second electrodes. In some embodiments, the nanochannel delivery device comprises a substantially planar body and wherein the first exterior surface and the second exterior surface are substantially parallel. In particular embodiments, the nanochannel is in direct fluid communication with the first and second microchannels.

BRIEF DESCRIPTION OF THE FIGURES

FIG. 35 shows a current profile over elapsed time at applied voltage steps (0.4V, 0.8 V, 1.2V and 1.6V). The data were collected with an NDDE 150 #2 membrane. FIG. 36 shows a current profile over elapsed time at applied voltage steps (1.9V, 1.6 V, 1.2V, 0.8V and 0.4V). The data were collected with the NDDE 150 #2 membrane.

FIG. 38 shows "step-up" V-I curve for nDS2, 15 #1, #2, #6, #7, #8, and #9. FIG. 39 shows hysteresis effect in the V-I curves for nDS2 150 #2 at increasing and decreasing voltage.

DETAILED DESCRIPTION OF ILLUSTRATIVE EMBODIMENTS

Nanodevice Design and Fabrication

Certain exemplary embodiments of the bulk microfabricated nanochannel membranes (also referred to as "NDS") described herein consist of a micromachined silicon wafer and a Pyrex cap housing electrodes. Exemplary embodiments comprise features and fabrication techniques described in U.S. Patent Publications 2007/0066138 ("Diffusion Delivery Systems and Methods of Fabrication") 2010/0152699 ("Nanochanneled Device and Method of Fabrication"), incorporated herein by reference.

In addition to the preceding design and fabrication techniques, NDD devices can also be designed and fabricated according to methods and apparatus disclosed in U.S. Patent Publications U.S. Patent Publication 2007/0066138 ("Diffusion Delivery Systems and Methods of Fabrication") and U.S. Patent Publication 2010/0152699 ("Nanochanneled Device and Method of Fabrication"), incorporated herein by reference. Various methods can be used to apply conductive (e.g. metal) coatings for use as electrodes using a "baseline" NDS device. Exemplary embodiments of a baseline NDS device comprise a planar body (with first and second opposing surfaces) comprising a plurality of nanochannel lines. Along the nanochannel lines are alternating inlet microchannel and outlet microchannel structures. The inlet microchannels extend into the body of the device to couple a nanochannel with the first opposing surface, optionally intersecting with the larger macrochannels. The outlet microchannels couple the second opposing surface with a nanochannel. Multiple nanochannel lines can be coupled to each macrochannel, and the device may contain multiple macrochannels.

Figure 1:
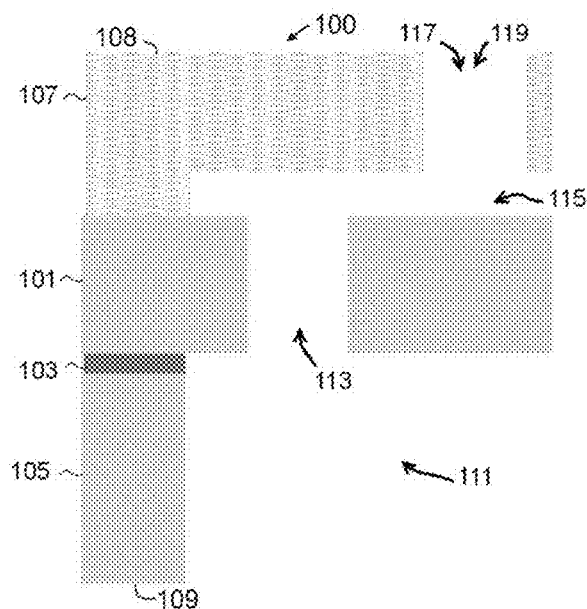
FIG. 1 illustrates an exemplary method of manufacturing a nanochannel device without electrodes.

Furthermore, multiple NDS devices can be simultaneously fabricated on larger Silicon-on-Insulator (SOI) silicon wafers through processes described below. The individual NDS devices can be obtained by dicing this larger wafer. Referring now to FIG. 1, a cross section of an NDS device 100 is shown with a nanochannel line located within a planar body with opposing surfaces 108, 109. In this embodiment, comprising a nanochannel line coupled to microchannels and a macrochannel, one exemplary method of manufacturing the baseline NDS configuration without electrodes is described as follows.

In this embodiment, an underlayer and hardmask layers (not shown) can be deposited on a SOI wafer (101, 103, 105) prior to an inlet microchannel 113 being patterned and etched. Following a cleaning step, a liner layer (not shown) can be deposited and then a plug can be deposited and chemical-mechanical polished. Following another cleaning step, a layer that will form nanochannel 115 can be deposited. An overlayer (not shown) can then be deposited and nanochannel 115 patterned and etched.

Following another cleaning step, a dielectric layer or stacks of layers 107 can be deposited, the outlets patterned, and a first outlet microchannel 117 etched. Following another cleaning step, a protective liner layer or layers can be deposited and a second outlet microchannel 119 etched. After cleaning, a frontside protective layer (not shown) can be deposited and the apparatus inverted (from the position shown in FIG. 1). Hardmask layers can then be deposited and macrochannels 111 patterned and etched to stop on the buried oxide layer 103. The buried oxide layer 103 is then etched along with residual hardmask. The wafer is cleaned to remove the inlet and liner sacrificial layers. A protective liner layer (not shown) can be deposited. Alternately, the other sacrificial materials can be removed at the wafer level and the wafer can be then divided up into individual nanochannel devices.

In another method, the outlet 117, the inlet 113, the nanochannel 115 and the macrochannel 111 can be formed without protective layers and the protective layers can be applied after all the sacrificial materials are removed.

Figure 2:
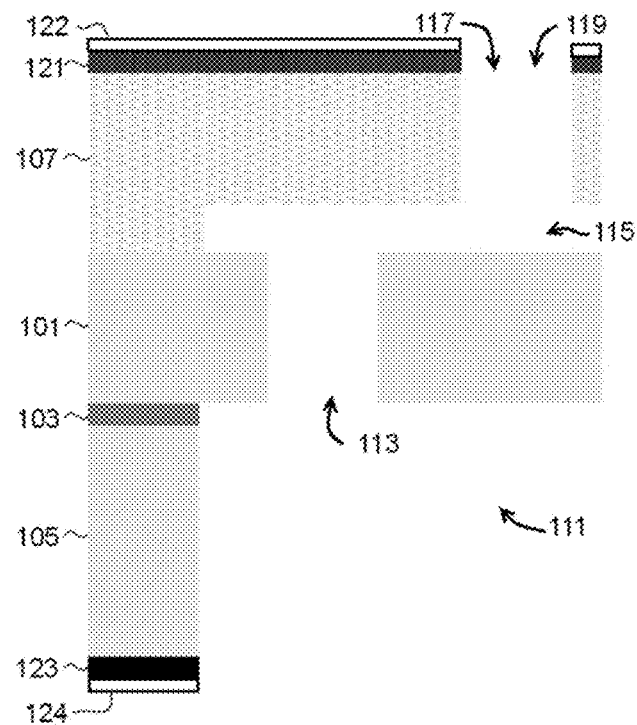
FIGS. 2-7 illustrate exemplary methods to provide for electrodes in a nanochannel device.

Referring now to FIG. 2, in another embodiment, additional steps can be incorporated to provide for electrodes in the nanochannel device. For example, an underlayer and hardmask layers (not shown) can be deposited on a wafer prior to an inlet 113 being patterned and etched. Following a cleaning step, a liner layer (not shown) can be deposited and then a plug can be deposited and chemical-mechanical polished. Following another cleaning step, a layer that will form nanochannel 115 can be deposited. An overlayer (not shown) can then be deposited and nanochannel 115 patterned and etched.

Following another cleaning step, a dielectric layer 107 can be deposited. This embodiment differs from the embodiment described in the discussion of FIG. 1 above, however. In this embodiment, after dielectric layer 107 has been deposited, a conductive layer 121 (that can serve as an electrode) is also deposited. As used herein, the term "electrode" comprises any electrically-conductive material, including for example, metal. In the embodiment shown, conductive layer 121 is directly coupled to a surface of the nanochannel device. In exemplary embodiments, metal layers (e.g. electrodes) can be directly coupled to a surface of the nanochannel device including for example a surface of an exterior surface of the device, a surface of an inlet or outlet microchannel surface, or a surface of a nanochannel surface.

Following the deposition of dielectric layer 107 and conductive layer 121, the outlets can be patterned and a first outlet 117 etched. The next several steps are equivalent to those used in the embodiment shown and described in FIG. 1. For example, following another cleaning step, a protective liner layer can be deposited and a second outlet 119 etched. After cleaning, a frontside protective layer (not shown) can be deposited and the apparatus inverted (from the position shown in FIG. 2). Hardmask layers can then be deposited and macrochannels 111 patterned and etched to stop on the buried oxide layer 103. The buried oxide layer 103 is then etched and the wafer is cleaned and a liner layer (not shown) is deposited. Unlike the previous embodiment, a non-conformal conductive layer 123 can then be deposited to serve as a second electrode. In certain embodiments, additional optional layers 122 and 124 can be applied to layers 121 and 123 respectively, to protect and/or isolate layers 121 and 123 from the outside environment. It is understood that other embodiments described herein can include layers similar to layers 122 and 124 to protect and/or isolate conductive layers from the outside environment. Again, the wafer can then be divided up into individual nanochannel devices and the sacrificial layers removed.

Figure 3:
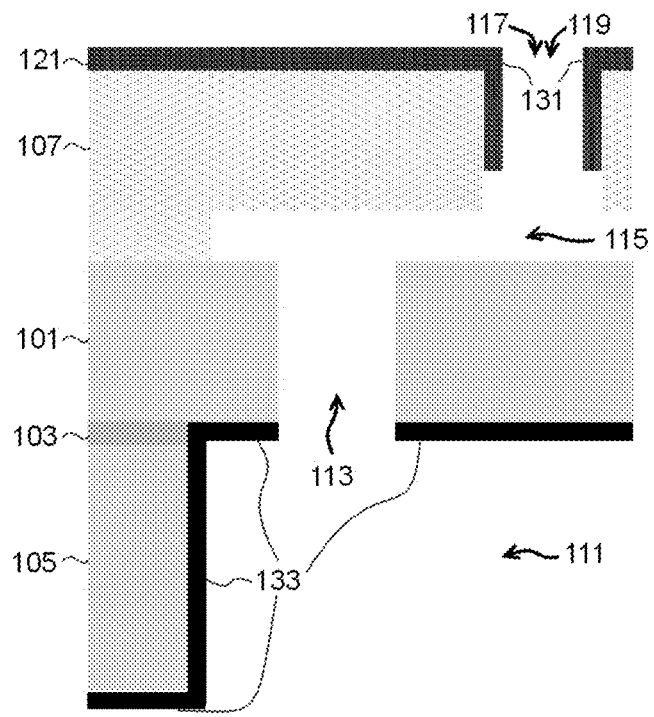

Referring now to FIG. 3, in yet another embodiment, additional steps can be incorporated to provide for electrodes with a different configuration than that shown in FIG. 3. In this embodiment, additional material is deposited to provide electrodes that are even closer to nanochannel 115 than that of previously-described embodiments. The first several steps are generally equivalent to those provided in the description of FIG. 2.

For example, an underlayer and hardmask layers (not shown) can be deposited on a wafer prior to an inlet 113 being patterned and etched. Following a cleaning step, a liner layer (not shown) can be deposited and then a plug can be deposited and chemical-mechanical polished. Following another cleaning step, a layer that will form nanochannel 115 can be deposited. An overlayer (not shown) can then be deposited and nanochannel 115 patterned and etched.

Following another cleaning step, a dielectric layer 107 can be deposited. After dielectric layer 107 has been deposited, a conductive layer 121 (that can serve as a portion of an electrode) is also deposited.

Following the deposition of dielectric layer 107 and conductive layer 121, the outlets can be patterned and a first outlet 117 etched. Following a cleaning step, a metal liner layer 131 can be deposited that extends into first outlet 117. Metal liner layer 131 is deposited in a manner and location so that it is electrically couple to previously-deposited metal liner layer 121. Accordingly, metal liner layers 121 and 131 can serve as a continuous unit and function as a single electrode.

To protect this electrode sidewall layer from further process induced damage, a sacrificial layer can be deposited on top of this conductive layer 131, which can later be selectively removed. The next several steps are equivalent to those used in the embodiment shown and described in FIG. 2. For example, a second outlet 119 can then be etched and after cleaning, a frontside protective layer (not shown) can be deposited. The apparatus can then be inverted from the position shown in FIG. 3.

Hardmask layers can then be deposited and macrochannels 111 patterned and etched to stop on the buried oxide layer 103. The buried oxide layer 103 is then etched along with the residual hardmask. The wafer is cleaned to remove the inlet and liner sacrificial layers. A protective liner layer (not shown) is deposited. A conformal metal layer 133 can then be deposited to serve as a second electrode. Unlike the non-conformal metal layer deposited in FIG. 2, the conformal metal layer 133 extends into the macrochannels 111. This again places the second electrode in close proximity to nanochannel 115. In certain specific embodiments, metal layers 131 and 133 are within approximately 30 microns of nanochannel 115. In particular embodiments, metal layers 131 and 133 are within 10, 15, 20, 21, 22, 23, 24, 25, 26, 27, 28, 29, 30, 31, 32, 33, 34, 35, 36, 37, 38, 39, 40, 45 or 50 microns of nanochannel 115.

After depositing metal layers 131 and 133, the wafer can then be divided up into individual nanochannel devices and the sacrificial layers removed. Alternately, the other sacrificial materials can be removed at the wafer level and the wafer is then divided up into individual nanochannel devices Referring now to FIG. 4, in yet another embodiment, additional steps can be incorporated to provide for electrodes with a different configuration than that shown in FIGS. 2 and 3. In this embodiment, additional material is deposited to provide electrodes that are even closer to nanochannel 115 than that of previously-described embodiments.

In the initial steps, an underlayer and hardmask layers (not shown) can be deposited on a wafer prior to an inlet 113 being patterned and etched. Following a cleaning step, a metallic liner layer 135 can be deposited on inlets 113. In addition, any sacrificial liner layers, which can be easily removed later in the process, can be deposited to protect the electrode material, if needed. This is followed by a plug that can be deposited and chemical-mechanical polished.

The remaining processing steps are equivalent to those provided in the description of FIG. 3 above. For example, following another cleaning step, a layer that will form nanochannel 115 can be deposited. An overlayer (not shown) can then be deposited and nanochannel 115 patterned and etched. Following another cleaning step, a dielectric layer 107 can be deposited. After dielectric layer or layers 107 have been deposited, a conductive layer 121 (that can serve as a portion of an electrode) is also deposited.

Following the deposition of dielectric layer 107 and conductive layer 121, the outlets can be patterned and a first outlet 117 etched. Following a cleaning step, a metal liner layer 131 can be deposited that extends into first outlet 117. Metal liner layer 131 is deposited in a manner and location so that it is electrically coupled to previously-deposited metal liner layer 121. Accordingly, conductive liner layers 121 and 131 can serve as a continuous unit and function as a single electrode. To protect this electrode sidewall layer from further process induced damage, a sacrificial layer can be deposited on top of this conductive layer 131, which can later be selectively removed A second outlet 119 can then be etched and after cleaning, a frontside protective layer (not shown) can be deposited. The apparatus can then be inverted from the position shown in FIG. 4.

Hardmask layers can then be deposited and macrochannels 111 patterned and etched to stop on the buried oxide layer 103. The buried oxide layer 103 is then etched along with residual hardmask and the inlet sacrificial materials removed. A conformal metal layer 133 can then be deposited to serve as a portion of second electrode. The conformal metal layer 133 extends into the macrochannels 111 and is electrically coupled to metallic liner layer 135. Accordingly, metal liner layers 133 and 135 can serve as a continuous unit and function as a single electrode.

Figure 4:
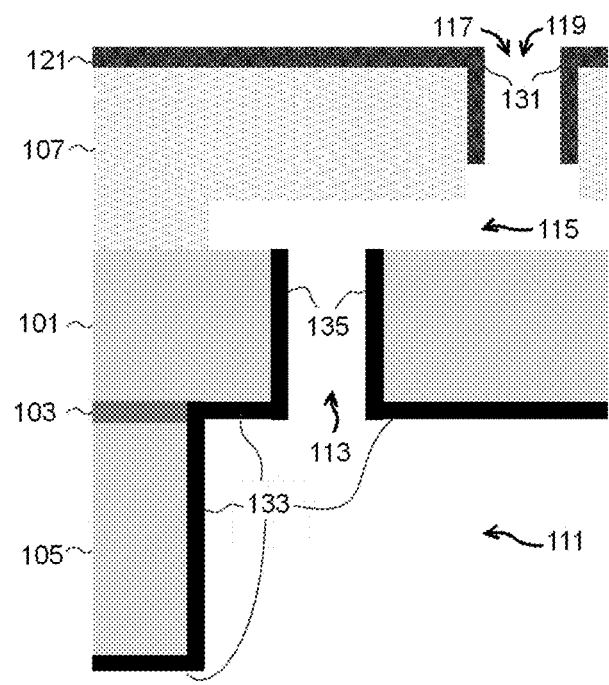

The configuration shown in FIG. 4 places the second electrode in close proximity (e.g. adjacent) to nanochannel 115. In certain specific embodiments, metal layers 131 and 135 are within approximately 15 microns of nanochannel 115. In particular embodiments, conductive layer 131 is within 0.0, 0.1, 0.2, 0.3, 0.4, 0.5, 0.6, 0.7, 0.8, 0.9, 1, 2, 3, 4, 5, 6, 7, 8, 9 or 10 microns of nanochannel 115 and conductive layer 135 is within 0.0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45 or 50 microns of nanochannel 115. In certain embodiments, metal layer 135 extends fully into inlet 113 such that it is directly adjacent to nanochannel 115 (e.g. within 1 micron of nanochannel 115).

After depositing metal layers 131 and 133, the wafer can then be divided up into individual nanochannel devices and the sacrificial layers removed. Alternatively, the sacrificial materials are first removed at the wafer level and then the wafer is divided up into individual devices.

Figure 5:
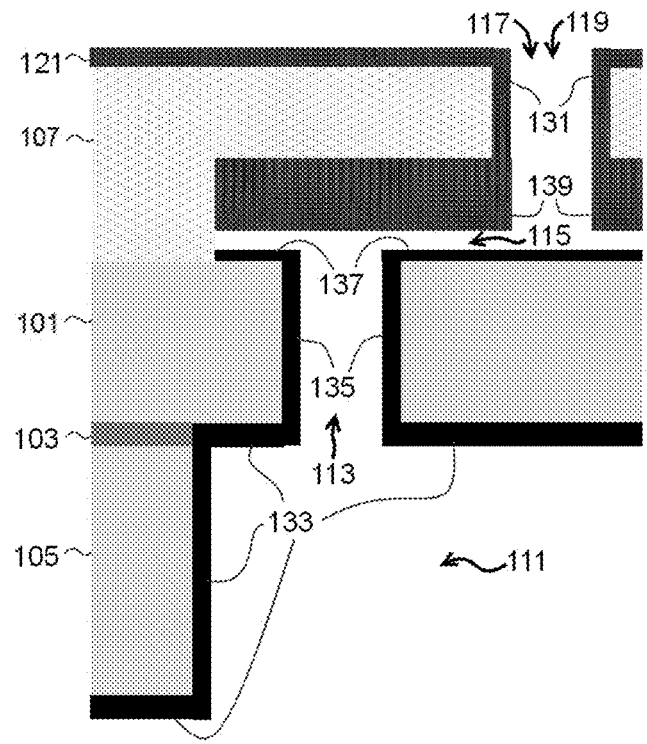

Referring now to FIG. 5, another embodiment comprises processing steps that allow for the top and bottom surfaces of nanochannel 115 to be coated with material that can be used as electrodes during operation. In the embodiment shown, a metal underlayer 137 can be initially deposited on a wafer prior to the deposition of hardmask layers (not shown). An inlet 113 can then be patterned and etched, followed by a cleaning step. A metallic liner layer 135 can be deposited on inlets 113, followed by a plug that can be deposited and chemical-mechanical polished. In exemplary embodiments, metallic liner layer 135 can be deposited in a manner and location such that it is electrically coupled with metal underlayer 137.

Following another cleaning step, a layer that will form nanochannel 115 can be deposited. A metal overlayer 139 can then be deposited and nanochannel 115 patterned and etched. The remaining processing steps are generally equivalent to those provided in the description of FIG. 4 above.

For example, following another cleaning step, a dielectric layer 107 can be deposited. After dielectric layer 107 has been deposited, a conductive layer 121 (that can serve as a portion of an electrode) is also deposited.

Following the deposition of dielectric layer 107 and conductive layer 121, the outlets can be patterned and a first outlet 117 etched. Following a cleaning step, a conductive liner layer 131 can be deposited that extends into first outlet 117. Conductive liner layer 131 is deposited in a manner and location so that it is electrically coupled to previously-deposited conductive layer 121 and conductive underlayer 139. Accordingly, conductive layers 121, 131 and 139 can serve as a continuous unit and function as a single electrode. Any additional sacrificial layers to protect the electrode sidewall can then be deposited. A second outlet 119 can then be etched and after cleaning, a frontside protective layer (not shown) can be deposited. The apparatus can then be inverted from the position shown in FIG. 5.

Hardmask layers can then be deposited and macrochannels 111 patterned and etched to stop on the buried oxide layer 103. The buried oxide layer 103 is then etched along with residual hardmask and the inlet sacrificial materials removed. A conformal metal layer 133 can then be deposited to serve as a portion of second electrode. The conformal metal layer 133 extends into the macrochannels 111 and is electrically coupled to metallic liner layer 135, which is in turn electrically coupled to metallic underlayer 137. Accordingly, metal liner layers 133, 135 and 137 can serve as a continuous unit and function as a single electrode.

After depositing conductive layer 131, the wafer can then be divided up into individual nanochannel devices and the sacrificial layers removed. Alternatively, the sacrificial materials are first removed at the wafer level and then the wafer is divided up into individual devices.

The configuration shown in FIG. 5 places metallic layers 137 and 139 of the first and second electrodes on opposing surfaces of nanochannel 115. In certain specific embodiments, metal layers 137 and 139 are within approximately 250 nanometers (nm) of each other. In particular embodiments, metal layers 137 and 139 are within 500, 400, 300, 200, 100, 90, 80, 70, 60, 50, 40, 30, 20 or 1, 2, 3, 4, 5, 6, 7, 8, 9, or 10 nm of each other.

The proximity and location of metal layers 137 and 139 directly on the surfaces of the nanochannels 115 provides numerous advantages during operation of the nanochannel delivery systems with electrodes (NDSE). For example, the movement of molecules passing through nanochannels 115 can be influenced or controlled with a smaller voltage than would be required with configurations that placed the electrodes more distal from the nanochannel.

The configuration shown and described in FIG. 5 can also provide for more precise control of the movement of molecules through nanochannels 115 during operation. For example, during operation a user can apply positive and negative voltage to the entire surfaces opposing each other in nanochannels 115. This can expose molecules passing through nanochannel 115 to electrical energy from the electrodes (as compared to configurations with electrodes only on the inlet and outlet microchannels, which have a much greater cross-sectional area than the nanochannels). Molecules that pass through the central portions of the inlet and outlet microchannels will not be as affected by the electrical energy from the electrodes as molecules that are in close proximity to the electrodes. By locating the electrodes on the nanochannel surfaces (which are much closer to each other than electrodes located on micro or macrochannel surfaces) each molecule passing through the nanochannel will be in relatively close proximity to an electrode. This configuration will allow electrical energy from the electrodes to affect the movement of molecules to a greater degree and will in turn provide greater control of the passage of molecules through nanochannel 115 (e.g., the diffusion rate of the molecules through nanochannel 115).

Figure 6:
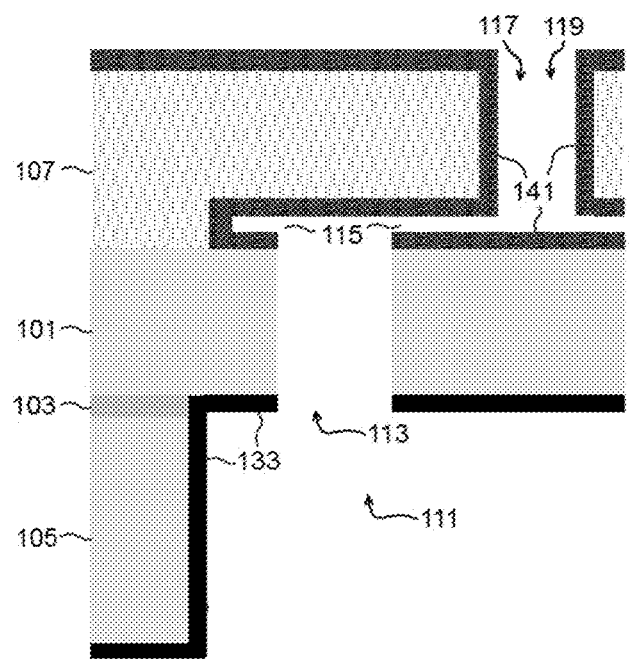

Referring now to FIG. 6, another embodiment comprises processing steps similar to those used in the "baseline" NDS design shown and described in FIG. 1.

In this embodiment, inlets 113 can be patterned and etched on a wafer. Following a cleaning step, a liner layer (not shown) can be deposited and then a plug can be deposited and chemical-mechanical polished. Following another cleaning step, a layer that will form nanochannel 115 can be deposited. An overlayer (not shown) can then be deposited and nanochannel 115 patterned and etched.

Following another cleaning step, a dielectric layer 107 can be deposited, the outlets patterned, and a first outlet 117 and a second outlet 119 etched. After cleaning, a frontside protective layer (not shown) can be deposited and the apparatus inverted (from the position shown in FIG. 6). Hardmask layers can then be deposited and macrochannels 111 patterned etched to stop on the buried oxide layer 103.

The buried oxide layer 103 can then be etched along with the residual hardmask and the inlet sacrificial materials removed. A conformal metal layer 133 can then be deposited on the exposed surfaces on one side of inlet 113 as shown in FIG. 6.

The wafer can then be divided up into individual nanochannel devices and the sacrificial layers removed. After the wafer is divided into individual nanochannel devices, a conformal metal layer 141 can be deposited to the exposed surfaces on nanochannel 115 and outlets 117, 119. Alternatively, the sacrificial materials are first removed at the wafer level. The wafer is then divided into individual devices and the conformal metal layer 141 can be deposited to the exposed surfaces on the nanochannel 115 and outlets 117, 119. Similar to the previous embodiment shown in FIG. 5, this embodiment comprises metal layers on either side of nanochannel 115. However, unlike the previous embodiment, metal layers 141 on either side of nanochannel 115 are electrically coupled and therefore will have the same electrical polarity (e.g. positive or negative voltage, as measured against ground).

Nanochannel 115 can effectively be used similar to a control valve with electrically-coupled metal layers 141 on each side of nanochannel 115. For example, applying the same type of electric charge to metal layers 141 can repel molecules of a fluid in nanochannel 115 away from metal layers 141 on opposing surfaces of nanochannel. This can effectively narrow the pathway through nanochannels 115 in which molecules are capable of passing and restrict the movement of the fluid molecules.

Figure 7:
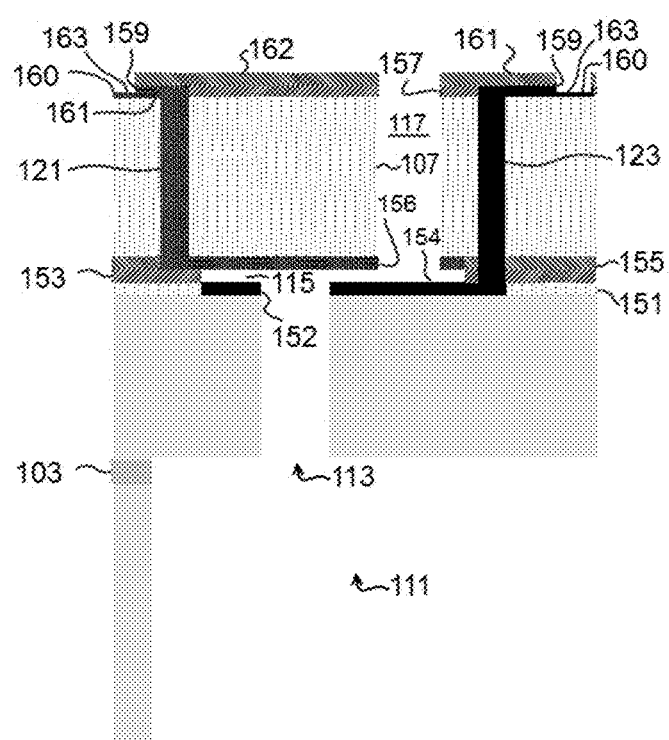

Referring now to FIG. 7, this embodiment comprises a significantly different process than those previously described. This embodiment also provides several structural distinctions as compared to previous embodiments. For example, while providing electrodes with opposing polarities on surfaces on opposite sides of the nanochannel, it also allows external electrical connections to be made to the electrodes from the same "side" of the nanochannel (as explained in greater detail below).

The structure as in FIG. 7 can be accomplished by a multiplicity of methods, and three examples are provided. Bondpads connecting the outside to the electrodes on the nanochannel surfaces are connected through lines and contact vias.

In one embodiment, a dielectric layer 151 can initially be deposited on a wafer. A metal underlayer can then be patterned and etched. After a cleaning step the metal underlayer can be filled, followed by chemical-mechanical polishing/planarizing (CMP) of the metal underlayer.

Next, the wafer can be cleaned to complete the metal underlayer 152. Inlets 113 can be patterned and etched, followed by a cleaning and lining of inlets 113. A plug (not shown) can then be deposited and subjected to a CMP process.

A dielectric layer 153 can be deposited and then space for nanochannels 115 can be patterned and etched. After a cleaning step, a nanochannel layer 154 (e.g., a layer that is on the same plane as nanochannels 115) can be deposited and subjected to a CMP process. A dielectric layer 155 can then be deposited and an overlayer space patterned and etched.

After a cleaning step, an overlay metal layer 156 can be deposited, subjected to a CMP process, and then cleaned. Alternatively, the overlay metal layer can be deposited, patterned, etched and cleaned. A dielectric layer 107 can then be deposited, followed by deposition of a dielectric overlayer 157. Lines 159 and bond pads 160 can be patterned and etched, followed by a cleaning step.

Contact vias 161 can then be patterned and etched up to metal overlayer 156 or metal underlayer 152. Following another cleaning step, interconnect metal can be deposited in lines 159, bond pads 160 and vias 161. A passivation layer 162 can then be deposited and bond pads 163 patterned and etched up to lines 159. After another cleaning step, outlets can be patterned in passivation layer 162. Outlets 117 can then be etched in passivation layer 162, dielectric overlayer 157, dielectric layer 107, and metal overlayer 156, stopping at nanochannel layer 154.

Following another cleaning step, a protective later can be deposited and the apparatus inverted (from the position shown in FIG. 7). Hardmask layers can then be deposited and macrochannels 111 patterned and etched to stop on the buried oxide layer 103. The buried oxide layer 103 is then etched and the wafer is cleaned and a liner layer (not shown) is deposited. The wafer can then be divided up into individual nanochannel devices and the sacrificial layers removed.

In a second embodiment, a dielectric layer 151 can initially be deposited on a wafer. A trench in the dielectric, to be later filled with underlayer electrode, is then patterned and etched. After a cleaning step the metal underlayer is deposited to fill in the trench, followed by chemical-mechanical polishing/planarizing (CMP) of the metal overburden to stop on the dielectric layer 151. The wafer can be cleaned to complete the underlayer metal electrode 152.

Inlets 113 can be patterned and etched in the layer 152 and into the silicon, stopping on the buried oxide, followed by a cleaning and lining of inlets 113. A plug (not shown) can then be deposited and subjected to a CMP process.

A sacrificial nanochannel layer 154 can be deposited, with an optional sacrificial dielectric overlayer and nanochannel lines can be patterned and etched and the sacrificial material removed.

A dielectric layer 155 can then be deposited and a trench in the dielectric, to be later filled with overlayer electrode, is then patterned and etched. After a cleaning step, an overlay metal layer 156 can be deposited to fill in the trench, followed by a CMP process of the metal overburden to stop on the dielectric 155, and then cleaned to complete the overlayer metal electrode 156.

A thick dielectric layer or stack 107 can then be deposited, followed by deposition of a dielectric overlayer 157. Lines 159 and bond pads 160 can be patterned and etched in the dielectric layer 157, followed by a cleaning step.

Contact vias 161 can then be patterned and etched down to metal overlayer 156 or metal underlayer 152. Following another cleaning step, an interconnect metal can be deposited in lines 159, bond pads 160 and to fill the vias 161. A CMP process is again used to remove the excess overburden. Optionally, a passivation layer 162 can then be deposited and bond pads 163 patterned, etched and cleaned. This results in electrical contact between the bond pads and the metal under or overlayers through the lines and the contact vias.

After another cleaning step, outlets can be patterned on passivation layer 162. Outlets 117 can then be etched in passivation layer 162, dielectric overlayer 157, dielectric layer 107, and stopping in the metal overlayer 156. After a clean and the application of a protective liner layer, a second etch is performed, stopping at nanochannel layer 154 or the metal underlayer 152.

Following another cleaning step, a protective later can be deposited and the apparatus inverted (from the position shown in FIG. 7). Hardmask layers can then be deposited and macrochannels 111 patterned and etched to stop on the buried oxide layer 103. The buried oxide layer 103 and the residual hardmask layer are then etched and the wafer is cleaned and a liner layer (not shown) is deposited. The wafer can then be divided up into individual nanochannel devices and the sacrificial layers removed, or the sacrificial layers removed and then divided up into individual nanochannel devices.

An alternate embodiment begins with the deposition of the metal underlayer 152, which is patterned, etched and cleaned. A dielectric layer 151 is then applied onto this surface and using a CMP process, the dielectric on top of the metal layer 152 is removed.

A sacrificial nanochannel layer 154 can be deposited, with an optional sacrificial dielectric overlayer and nanochannel lines can be patterned and etched and the sacrificial overlay can be removed.

A metal overlayer is then deposited and patterned, etched and cleaned to form the overlayer 156. A thick dielectric layer 107 is then deposited and planarized as necessary. Contact vias 161 can then be patterned and etched down to metal overlayer 156 or metal underlayer 152. Metal lines and bondpads are then patterned on the surface which contacts the via. This results in electrical contact between the bond pads and the metal under or overlayers through the lines and the contact vias. Optionally, a passivation layer 162 can then be deposited and bond pads 163 opened by patterning, etching and cleaning.

Outlets can be patterned on passivation layer 162. Outlets 117 can then be etched in passivation layer 162, dielectric overlayer 157, dielectric layer 107, and stopping in the metal overlayer 156. After a clean and the application of a protective liner layer, a second etch is performed, stopping at nanochannel layer 154 or the metal underlayer 152.

Following another cleaning step, a protective later can be deposited and the apparatus inverted (from the position shown in FIG. 7). Hardmask layers can then be deposited and macrochannels 111 patterned and etched to stop on the buried oxide layer 103. The buried oxide layer 103 and the residual hardmask layer are then etched and the wafer is cleaned and a liner layer (not shown) is deposited. The wafer can then be divided up into individual nanochannel devices and the sacrificial layers removed, or the sacrificial layers removed and then divided up into individual nanochannel devices.

Discussion of Additional Embodiment

Figure 8:
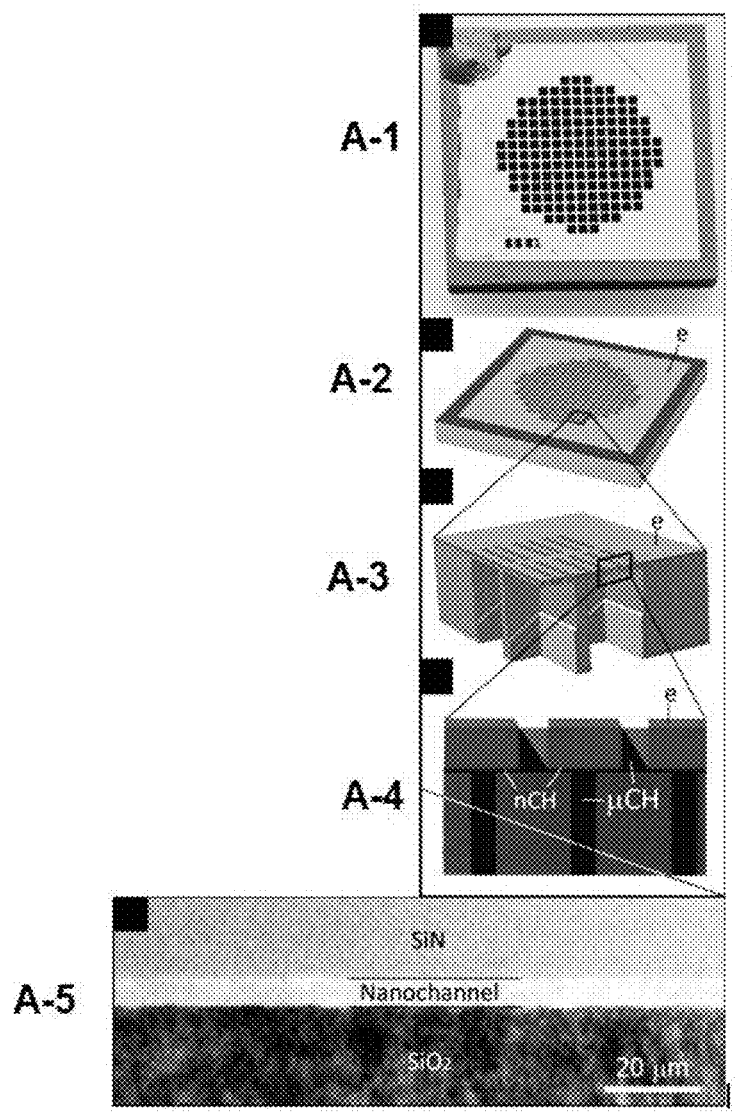
FIG. 8 illustrates images and schematics of a nanochannel device with electrodes. Image A-1 shows electrodes deposited in both surfaces of the membrane. Images A-2, A-3 and A-4 are magnifications of the membranes; nanochannels (nCH) and microchannels (μCH) are indicated. Image A-5 is a transmission electron microscope image of 5.7 nm nanochannel.

The nDS membranes discussed in this section were created using high precision silicon microfabrication technique as described in U.S. Pat. No. 8,480,637. In this work, nDS membranes presenting 5.7 nm were used. Additionally, microchannel membranes were employed, obtained by removing the SiN layer from the structure. All membrane adopted presented microchannels with a cross section of 1×3 $\mu m^2$ employed to integrate the electrodes onto nDS (FIG. 8). For the electron beam deposition, an ion assisted electron beam evaporator (CHA Industries, Inc., Fremont, Calif., USA) was employed.

Both sides of nDS membranes were coated with an electrode stack. Two different stack combinations were used: i) SiC—Ti (thickness 340 Å) and Pt (thickness 1800 Å), with a deposition angle of 10°; ii) SiN—Ta (thickness 100 Å) and Pt (thickness 600 Å), with a deposition angle of 90°. The coating procedure was performed as follows: first, the tungsten sacrificial layer was removed from the outlet side and the membranes were cleaned in a hot piranha bath ($H_2SO_4$+ $H_2O_2$). The nDS membranes were placed silicon-side down on a 4" silicon carrier wafer mounted on a dedicated U-shaped membrane holders made of Double Sided Scotch® reusable tabs (3M Company, St. Paul, Minn., USA), used to create an angled deposition inside the ion assisted electron beam evaporator. A Kapton® tape (DuPont, Wilmington, Del., USA) was cut in small strips and placed over the very edge of the membranes and affixed to the top of the reusable tabs to hold in place the nDS membranes and to avoid electrical short-circuit due to the possible deposition of metal on the sides of the chip. The outlet side of the membranes with nanochannels was deposited at 10° to avoid clogging of nanochannels. The extreme angle was necessitated by the low aspect ratio of the outlet microchannels (depth to width=1.5 to 5). The chips with only microchannels were deposited at 90°. Details of the assembly of nDS membranes into the diffusion device are described in the section below titled "DF-1 Diffusion".

Figure 9:
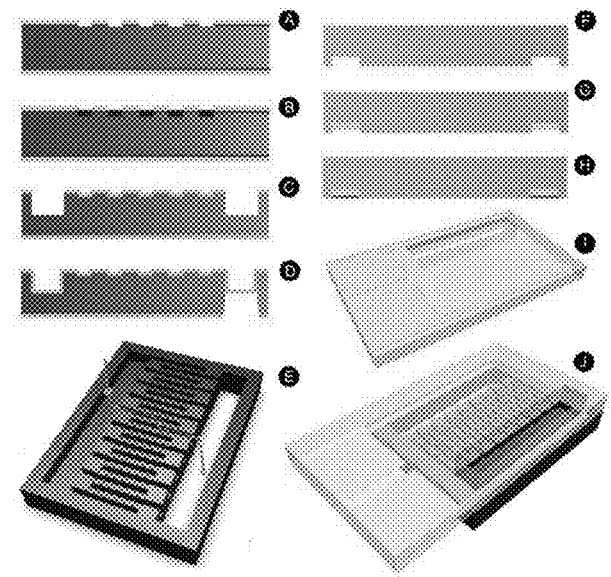
FIG. 9 illustrates the structure of an exemplary embodiment of the device and the microfabrication process flow. Schematic of the micro-fabrication process of the nanochannel Drug Delivery System (A-J). 3D illustrations of the machined silicon wafer (E), the Pyrex wafer (I), and the complete membrane (J).

As illustrated in FIG. 9 below, in exemplary embodiments the silicon wafer presents an interdigitated finger geometry composed of parallel microchannels connected to each other by an array of perpendicular nanochannels. In certain embodiments, the top surfaces of the micro- and nanochannels are obtained by anodically bonding the Pyrex capping wafer to a grid of anchor points. In exemplary embodiments, the nano-metric dimension of the nanochannels is the depth. As a result of a difference in potential applied to the embedded membrane electrodes, drug molecules can enter the membrane through the inlet that is drilled through the Pyrex, move through a set of 136 microchannels, then into a mesh of 120 nanochannels (two sets of 60 on each microchannel), and finally reach the outlet that is wet etched through the silicon wafer through another set of 136 microchannels.

FIG. 9 shows the structure of an exemplary embodiment of the device and the microfabrication process flow. In this embodiment, double side polished (DSP) silicon substrates were first cleaned in piranha solution (3:1 $H_2SO_4$ (96 vol %): $H_2O_2$ (30 vol %)) for 10 minutes at 120° C. A 50 nm silicon oxide pad layer was then thermally grown at 950° C. followed by a 150 nm thick low-stress nitride masking layer deposited using low pressure chemical vapor deposition (LPCVD). The masking layer served as a barrier to oxygen diffusion, preventing oxidation of the silicon surface. In this exemplary embodiment, nanotrenches were defined by standard photolithography with an EVG 620 aligner (EV Group, Inc.) on top of the nitride oxidation masking layer, which was later removed using a He+$SF_6$ plasma reactive ion etch (RIE). The oxide pad layer, grown to prevent over-etching by the previous RIE, can then be removed from the openings in the nitride masking layer using a 1:10 HF:$H_2O$ wet etching solution (see FIG. 9A below). A sacrificial oxide film can then be thermally grown to the desired thickness ($f$) through the nitride masking layer (see FIG. 9B below). The depth of the nanotrenches (H) can be determined using the relation H=0.46·$f$ that represents the ratio between oxide grown and silicon consumed. In this exemplary embodiment, the pad oxide, nitride, and sacrificial oxide layer can then be stripped in diluted HF solution.

Microtrenches can then be fabricated by depositing a 500 nm thick low temperature oxide (LTO) masking film onto the DSP silicon substrate by LPCVD. In this embodiment, chambers below and above the inlet and outlet as well as the microtrenches can be photolithographically defined on the LTO surface. The LTO mask can be etched in the defined areas using a He+$CHF_3$+$CF_4$ plasma RIE in this embodiment. For depths of 20 or 30 µm, an inductively coupled plasma (ICP) deep silicon etch process (Oxford Plasmalab 100) can be used. For 2 µm deep features, however, a wet etch can be performed with a 45 wt % KOH solution at 80° C. (FIG. 9C). The LTO mask can then be stripped in 1:10 diluted HF solution in this exemplary embodiment.

In one exemplary embodiment, the fabrication of the outlet through the DSP silicon substrate can be initiated with the deposition of a 150 nm thick LPCVD nitride masking film. Backside photolithography can then be performed defining the region of the outlet. The nitride mask can be etched in the defined area using a He+$SF_6$ plasma RIE in this embodiment. A through wafer etch can be performed in a 45 wt % KOH solution at 80° C. (see FIG. 9D below) followed by the removal of the nitride mask in diluted HF solution (see FIG. 9E below).

In this embodiment, a Pyrex 7740 wafer can be used for the top substrate fabrication because of its excellent bonding compatibility with silicon. First, trenches, used to house the metal electrodes, can be photolithographically defined and etched into the Pyrex substrate to a depth of 0.5 µm using a He+CHF3+CF4 plasma RIE (see FIG. 9F below). The photoresist can then be stripped off in piranha solution. Next, a second photolithography step can be performed to define the position of the metal electrodes inside the trenches. An electron-beam (e-beam) metal evaporator can be employed to blanket deposit the titanium (Ti 0.05 µm)/platinum (Pt 0.15 µm) electrodes on the substrate surface in this embodiment. Then, the excess metal on top of the photoresist can be "lifted-off" leaving behind the metal electrodes inside the 0.5 µm trenches (see FIG. 9G below). The substrate can then be covered by a 1 µm thick oxide through a PECVD process performed at 200° C., below the Pyrex transition temperature, to cover the newly deposited electrodes in. This can be followed by a chemical mechanical polishing/planarizing (CMP) step to remove the excess deposited oxide back down to the original Pyrex surface and leave only a thin layer covering the electrodes (see FIG. 9H below). Next, the areas of the metal electrodes inside the fluidic region as well as over the device contact pads were re-exposed to insure good electrical contact to both the solution and the device while preventing fluid leakage. In this embodiment, these windows can then be photolithographically defined and etched with a He+CHF3+CF4 plasma RIE to a depth of 0.6 µm leaving a small oxide plug to prevent fluid leakage (see FIG. 9I below). The internal windows can be designed to have a 25 µm overlap with the microfluidic chambers beneath and above the inlet and outlet. The exposure of the metal in this region is fundamental for the establishment of an electrokinetic flow through the device. The outlet can then be machined into the substrate by ultrasonic drilling (e.g., utilizing technology from Bullen Ultrasonics, Inc.).

In certain embodiments, the Pyrex wafer and DSP silicon substrate can be finally bonded together using an anodic bonding technique performed on an EVG520 wafer bonder to cap and form the micro- and nanochannels (see FIG. 9J below). In specific embodiments, the bonding conditions are 400 Volts at 350° C. for 10 minutes. In particular embodiments, photoresist can then be spun onto the bonded wafer to protect the nanochannels and microchannels from debris during membrane dicing. In certain embodiments, the 3×5.5 mm NDD devices can be finally diced from the bonded wafer and cleaned in ozone with an Acid Spray Tool (SPT).

DF-1 Diffusion

Figure 10:
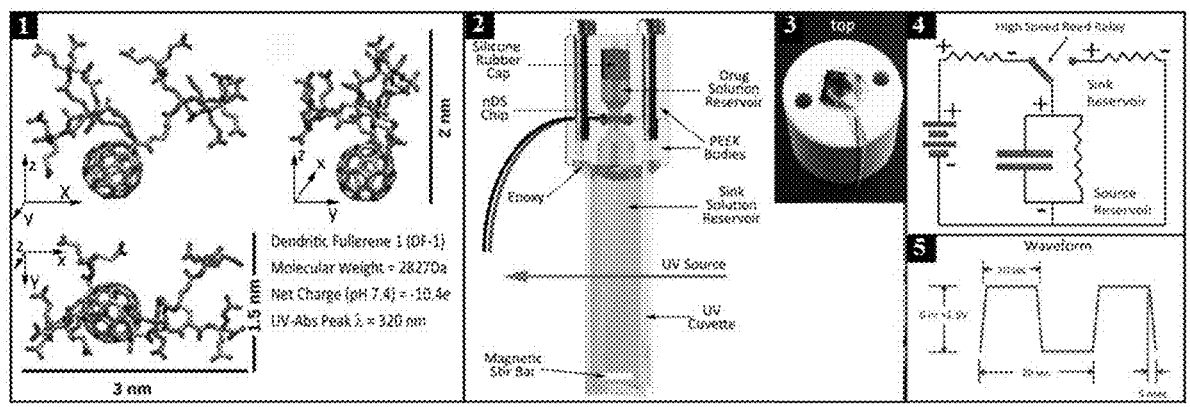
FIG. 10 illustrates schematics of a nanochannel device, a DF-1 molecule tested with the device, and a control system used during testing. Panel 1 presents the structure and the properties of DF-1. Panel 2 is a schematic of the custom diffusion device. Panel 3 is an image of an electro-deposited membrane placed into the PEEK body. Panel 4 is a schematic of the system which include the membrane clamped between the PEEK bodies of the custom diffusion device. Panel 5 is the waveform used to modulate the release.

DF-1 (MW=2827 Da) presents a hydrodynamic diameter of 2.5 nm and a high negative charge of −10.4e at pH 7.4 (section 1 of FIG. 10). It is highly water-soluble and it presents a peak of adsorption at $\lambda$=320 nm.

Study of its diffusion through nDS membranes was performed under the influence of an applied AC electric field by means of UV-Vis spectrophotometry. The AC electric field was generated by modulating the application of a DC voltage to the nDS membrane using 1052C2RO and 1051C2RO high-speed reed relays (American Relays, Inc., Santa Fe, Calif., USA) controlled by a 33250A Function/Arbitrary Wave Function Generator (Agilent Technologies, Santa Clara, Calif., USA) between an "off" (passive) and "on" (active) state (sections 4 and 5 of FIG. 10). The circuit was constructed using an Elenco 9440 breadboard (Digikey, Thief River Falls, Minn., USA), 100 Ohm shunt resistors and 3952× Molex plugs (Molex, Lisle, Ill., USA). For absorbance measurements a Varian Cary 50 Bio UV-Vis spectrophotometer (Agilent Technologies, Santa Clara, Calif., USA) integrated with a custom 48-cuvette robotic carousel (developed by Quantum Northwest in collaboration with Agilent Technologies and our group) was employed. The diffusion study was performed with a custom diffusion device composed of two polyether ether ketone (PEEK) bodies housing source and sink reservoirs separated by the nDS membrane (FIG. 2B). The sink reservoir was obtained by attaching with OG116-31 UV-curing epoxy (Epoxy Technology, Inc., Billerica, Mass., USA) one of the PEEK bodies to a UV-macrocuvette (Sigma-Aldrich, St. Luis, Mo., USA). The two bodies presented a machined conduit to allow the crossing of the wires that connect the electrodes with the control circuit (section 3 of FIG. 10). Two silicone rubber O-rings (Apple Rubber, Lancaster, N.Y., USA) sealed the membrane between the PEEK bodies. Two replicates were used for the experiment. Electrical leads were attached to the membranes using a conductive H20E 10Z epoxy (Epoxy Technology, Billerica, Mass., USA). Bare 36AWG Red and Black wire ends were attached to the membranes and cured at 150° C. for 10 minutes. The membranes were first immersed in isopropyl alcohol (IPA) for 2 hours to promote the wetting of all channels and then rinsed with Millipore water. Finally, the chips were immersed in the selected buffer solution overnight prior to performing the diffusion test. An absorbance standard curve ($\lambda$=320 nm) was obtained at DF-1 concentrations from (1.56 to 100 µg/ml). The chips were assembled into the custom diffusion devices, the source reservoir was loaded with 200 µl of DF-1 solution at concentration of 3 mg/ml in 50 mM NaCl and the sink reservoir was loaded with 4.25 ml of 50 mM NaCl solution. The custom carousel allowed homogenization of the sink solution by magnetic stirring at 300 rpm. The test was carried out at room temperature (23±0.1° C.). The data collected were normalized to the absorbance at t=0 and the cumulative release profile of DF-1 calculated.

The IV Characterization

The characterization of electrical properties of the different electrode stack combinations under a series of externally applied increasing voltage steps was performed. This includes qualitative observation of electrolytically induced bubbling. This was done to optimize both electrode stack and the biasing conditions to extend the operational lifetime of the nDS devices and to determine the effective operational range, in terms of applied voltage, of the nDS devices with an upper bound marked by significant gas formation. NDS membranes were soaked in IPA with the same procedure used in the previous experiments, and dried in an oven at 90° C. for approximately 1 hour. Then, they were broken onto halves in which the electrode stack was deposited approximately equally (squares or rectangles ≥1 cm on each side).

36 AWG black and red wire was stripped of its insulation and H20E 10Z epoxy (Epoxy Technology, Billerica, Mass., USA) was applied to one of the stripped ends of the red wire. The epoxy-coated end of the red wire was placed onto the corner of one of the cleaved chips on the electrode side. Once the wire was in place, the chip was placed onto an isotemp oven at 150° C. for 10 minutes to cure the epoxy. The process was then repeated with the black wire on the other cleaved chip. Reusable tabs were cut to a size that covers the full width and half length of each chip. With a distance of 1 mm between the two electrodes, the halves were placed on the reusable tab facing each other to create a sandwich. 50 mM NaCl solution was prepared using Millipore water. The end of the chip sandwich was attached to the shaft of a clean room swab using an appropriately sized piece of the reusable tab with the wire/insulating tape end in contact with the swab. Aluminum foil was placed under the petri dish (Fisher Scientific Inc., Hampton, N.H., USA) as a mirror to allow easier observation of bubble formation. The chip sandwich was then suspended over the petri dish using the swab. 50 mM NaCl solution was poured into the petri dish up to the level of the bottom of the insulating on the chip sandwich. A series of increasing DC voltage steps were applied between the membranes using a E3643A DC power supply (Agilent Technologies, Santa Clara, Calif., USA) and generated current was recorded, using a multimeter (Agilent Technologies, Santa Clara, Calif., USA), every second until the current stabilized for that particular voltage. The applied DC voltages usually ranged from 0.5 V to 2 V in steps of 0.25 V. As the voltage was being applied, the chips were checked periodically for bubble generation resulting from the applied voltage. The chip configurations were tested using the DC power supply and a 34970A Data Acquisition/Switch Unit (Agilent Technologies, Santa Clara, Calif., USA).

Surface Charge Measurement

Surface charge measurements of membranes were carried out using wafers (size 33×37 mm) that replicate the surface chemistry and structure of the membranes. The wafers were soaked in IPA, rinsed with Millipore water, dried and fitted into the flat surface cell of a Delsa Nano C Submicron Particle Size and Zeta Potential Analyzer (Beckman Coulter, Inc., CA, USA) with electrode side face down. Then, they were immersed in a 10 mM NaCl solution. Measurements, at 20 V with an expose surface area of 562 mm$^2$, were taken in a series of short (20-40 minutes) and long (5 hours) runs.

Results

Figure 11:
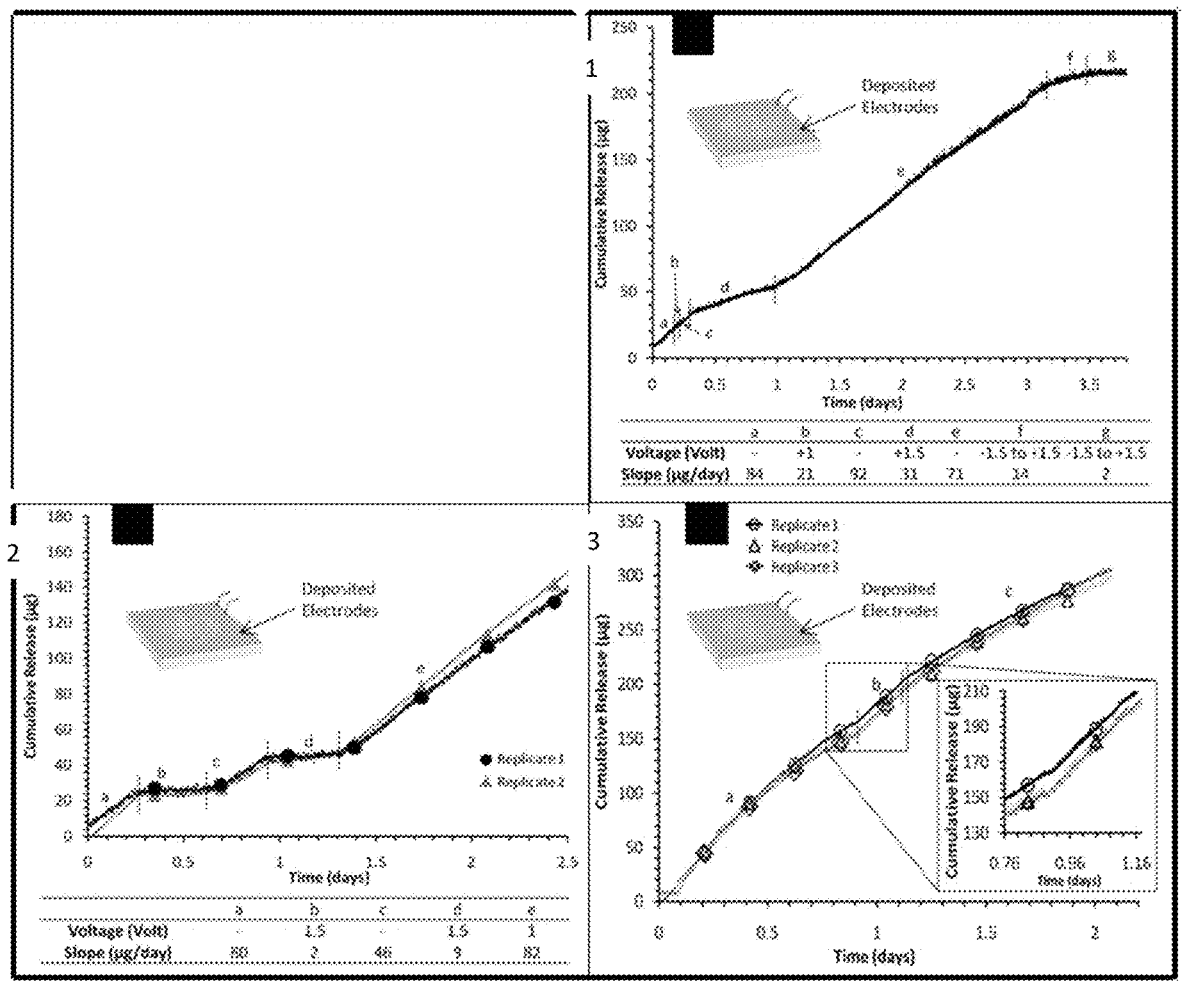
FIG. 11 illustrates graphs of the cumulative release of DF-1 during testing of a nanochannel device. Panels 1 and 2 show cumulative released amounts of DF-1 for electron beam deposited electrodes. The tables show the voltage applied in each period, labeled with letters, and the amount released (μg) in the corresponding period. Panel 3 presents the release trend of nDS membranes divided in three regions, each of which had different modulation setting: region a. $1.5V_{p-p}$, 20 sec pulse period, 50% duty cycle, positive bias at the source reservoir side, region b, enlarged in the inset, $2V_{p-p}$, 20 sec pulse period, 50% duty cycle, positive bias at the sink reservoir side, and region c, in which there was no voltage applied.
Figure 12:
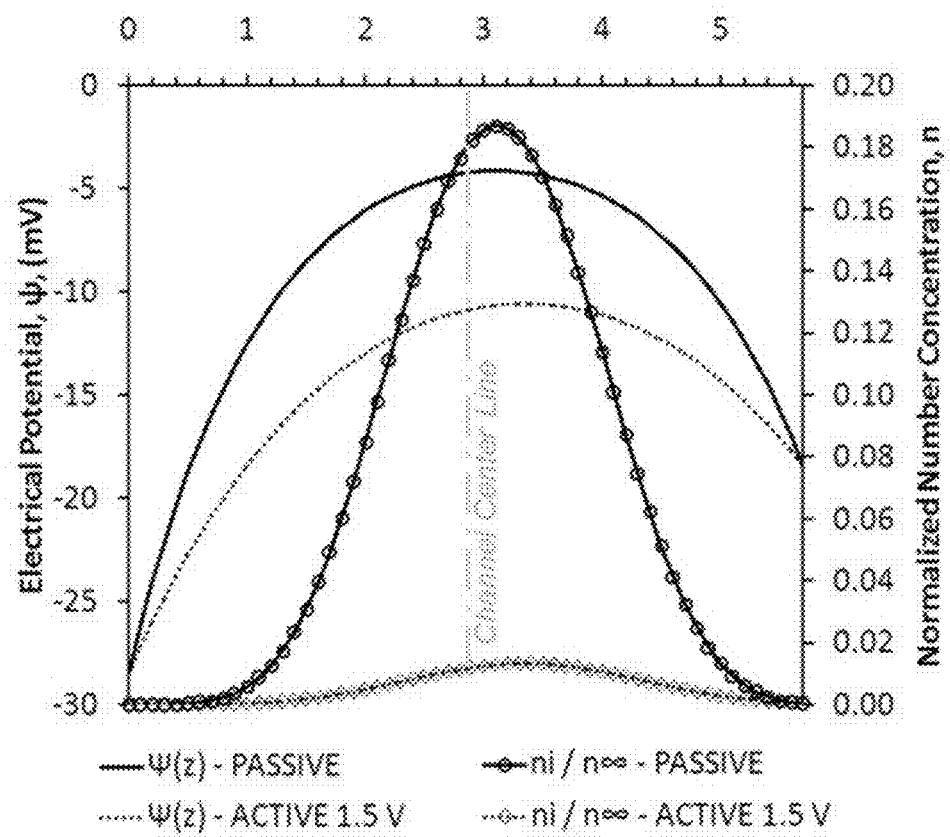
FIG. 12 illustrates a graph of passive and active release modes of a nanochannel device. Schematic representations of the electrical potential, Ψ (mV), and the normalized number, n, concentration of DF-1 into 5.7 nm nanochannel for deposited platinum electrodes. Three conditions of release are showed: passive, active 1.25 V and 1.5 V. n was normalized with respect to the source solution concentration.

FIGS. 11 and 12 depicts the cumulative release amount versus time of DF-1 through 5 nm (FIG. 11) and 1 µm (FIG. 12) membranes intermittently influenced by the previously described electrical waveform. The 5.7 nm nanochannels in these membranes were lined with silicon nitride (5 nm channels) with a zeta potential that was experimentally determined to be approximately 24 mV.

Discussion

By incorporating surface deposited platinum electrodes onto our previously reported nanochannel membranes, we have leveraged a mechanically robust and clinically relevant platform to temporally control drug release without significantly increasing fabrication or design complexity. Furthermore, these membranes do not require separate pumping compartments or any moving parts. These previously described drug delivery membranes can be incorporated into highly flexible capsule designs that can shield the larger biological elements found within the in vivo environment, including cells and large organellar structures, from any direct interaction with the modulating potentials. This is important given that some current is required to produce the release modulation, in the neighborhood of 1 to 50 µAmps. The lack of fabrication and design complexity from the delivery architecture leads to a more limited range of analytes that can be considered, as the delivered agents must be highly charged given the high ionic strength present in the in vivo environment, or would require a highly charged delivery vector, such as a micelle or fullerene complex similar to the DF-1 used here. Further enhancement and lower leakage currents can be achieved by moving the electrodes ever closer to the nanochannel, a very real possibility because of the highly flexible silicon fabrication techniques used to fabricate these membranes. The fabrication process allows for the manufacture of high nanochannel densities while allowing for the exquisite control over their total number and geometry optimized by means of the size of the chosen molecule. An optimum molecular hydrodynamic diameter-to-nanochannel height ratio of approximately 1:3 was determined to guarantee the release of molecules. This results in the confinement of the Brownian motion and a saturation of the mass flux for concentrations above a threshold. The design of the implantable capsules meant to host and protect the active nDS membrane can be highly adaptable to the requirements set by the pathology of the patient. This kind of customization may be controlled by volume of the reservoir and the material of which is made.

To accomplish a significant reduction of the drug release, a relatively high voltage was required. A square waveform, shown in FIG. 10 (section 5), was used to lower the average current. The applied potential was 1.5 V and the power consumption measured was between 1.5 µW and 75 µW, a very low power requirement for a battery.

FIG. 12 describes the electrical potential Ψ (mV), and the normalized number concentration n, for the surface deposited platinum electrodes. The figure shows the difference between the passive and active release modes for a 5.7 nm nanochannel The application of an electric potential creates a concentration polarization in the device, therefore there is an adjustment of the Debye length that leads to a different electric potential inside the channel. Since fewer particles with sufficient thermal energy can surmount the energy barrier once it is increased by the variation of the concentration of charge molecules due to the ion depletion, the modulation of the release rate results.

As used herein, the term "direct fluid communication" is interpreted as fluid communication between two bodies that are directly connected, e.g. such that fluid may exit one body and immediately enter the second body without flowing through an intermediate body.

Furthermore, as used herein, the term "inlet" is interpreted as a chamber or reservoir within a nanochannel delivery device that initially retains a substance being delivered via the nanochannel delivery device. Similarly, an "outlet" is interpreted as a chamber or reservoir within a nanochannel delivery device that retains a substance immediately prior to the substance exiting the nanochannel delivery device.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

By incorporating surface deposited platinum electrodes onto the previously reported nanochannel membranes, it is possible to leverage a mechanically robust and clinically relevant platform to temporally control drug release without significantly increasing fabrication or design complexity. Furthermore, these membranes do not require separate pumping compartments or any moving parts. These previously described drug delivery membranes can be incorporated into highly flexible capsule designs that can shield the larger biological elements found within the in vivo environment, including cells and large organellar structures, from any direct interaction with the modulating potentials. This is important given that some current is required to produce the release modulation, in the neighborhood of 1 to 50 µAmps. The lack of fabrication and design complexity from the delivery architecture leads to a more limited range of analytes that can be considered, as the delivered agents must be highly charged given the high ionic strength present in the in vivo environment, or would require a highly charged delivery vector, such as a micelle or fullerene complex similar to the DF-1 used here. Further enhancement and lower leakage currents can be achieved by moving the electrodes ever closer to the nanochannel, a very real possibility because of the highly flexible silicon fabrication techniques used to fabricate these membranes. The fabrication process allows for the manufacture of high nanochannel densities while allowing for the exquisite control over their total number and geometry optimized by means of the size of the chosen molecule. An optimum molecular hydrodynamic diameter-to-nanochannel height ratio of approximately 1:3 was determined to guarantee the release of molecules. This results in the confinement of the Brownian motion and a saturation of the mass flux for concentrations above a threshold. The design of the implantable capsules meant to host and protect the active nDS membrane can be highly adaptable to the requirements set by the pathology of the patient. This kind of customization may be controlled by volume of the reservoir and the material of which is made.

Experimental Apparatus and Procedures

Fluorescence Microscopy Imaging

In certain embodiments, a testing apparatus can be utilized to perform fluorescence microscopy imaging of the electrophoretic transport of analytes in the micro- and nanochannels of exemplary devices. In certain embodiments, the testing apparatus consists of a double-chamber system, in which a source and a sink solution are concentrically assembled on the top side of a glass coverslip.

Figure 13:
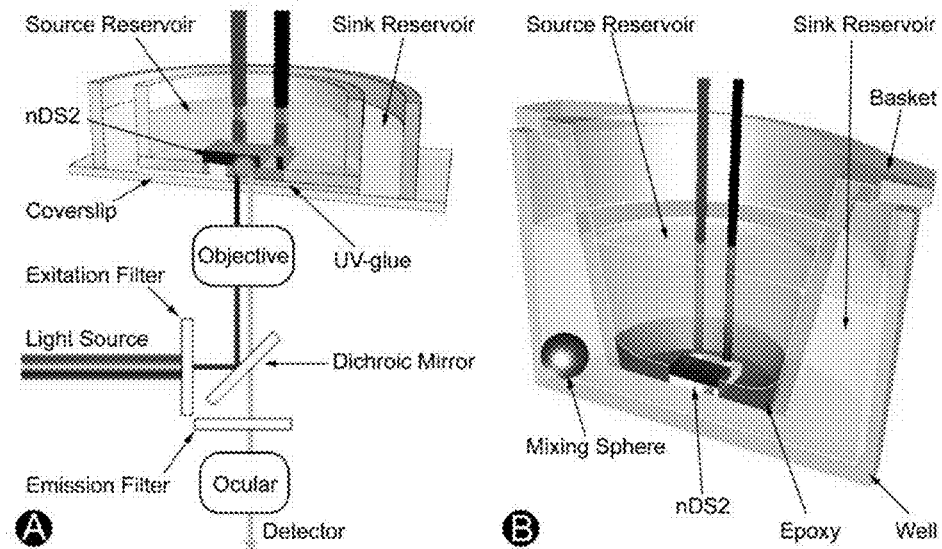
FIG. 13 illustrates a schematic of one embodiment of a nanochannel device testing apparatus.

FIG. 13 (section A) shows a schematic of one embodiment of a testing apparatus. In this embodiment, a wired NDD is epoxied at the bottom of a polyethylene ring with the Pyrex cap facing out of the cylinder in order to create a source reservoir. Next, the source reservoir is glued onto the glass coverslip by using an optical UV-glue (68, Norland Optical Adhesive). This procedure is carefully performed to 1) create a parallel empty gap between the coverslip and the membrane outlet and 2) to create an unobstructed optical path for the imaging of the inner structure of the NDD by means of an inverted fluorescence microscope (Zeiss LSM 510). Finally, a second larger ring is epoxied onto the same side of the coverslip circumscribing the source basket and thus creating the sink reservoir.

The sink reservoir is loaded with phosphate buffered saline (PBS) buffer and the membrane wetted from the outlet to prevent bubbles from clustering in the gap between the membrane and the coverslip. After 24 hours the complete wetting of the membrane can be verified by optical microscopy. In this embodiment, the source reservoir is filled with PBS to create continuity of fluid between the reservoirs and throughout the membrane. The PBS in the source reservoir is replaced with a PBS solution of 2%$_{wt}$ FITC-BSA (Sigma-Aldrich). A difference in potential of 3 VDC can then be applied to the NDD electrodes with the positive polarity at the outlet electrode. Snapshots of the fluorescence profile can then be collected through the fluorescence microscope camera at intervals of a few seconds.

Cumulative Active Release

In order to perform the cumulative active release measurement, the NDD can be wired and assembled into a testing device composed of a cell culture basket inserted into a cell culture well (see FIG. 13).

Electrical Contact

In this embodiment, the NDD membranes can be wired by using a solid silver-filled conductive epoxy (EPO-TEK® H20E), in a Part A:Part B ratio of 1:1. Wires (36 AWG) can be bonded to the membrane electrodes by means of small drops of epoxy applied to the contact pad of the electrode such that no conductive epoxy touched the diced sides of the membrane. In this embodiment, the epoxy can be cured for 15 minutes on a hot plate at 120° C. followed by approximately 1 hour in an oven at 110° C.

Insert Assembly

The NDD can be assembled into polystyrene cell culture inserts (12 well format, Becton Dikinson, USA) by using EPO-TEK® 353ND epoxy glue in a Part A:Part B ratio of 10:1. The epoxy mixture can then be loaded into a syringe with a 19½ G needle. A wired NDD membrane can be placed on a soft silicon rubber film that adheres well enough to prevent undercut of the epoxy. The polymeric membrane at the bottom of the basket can be removed and the insert placed on the silicon rubber in such way as to circumscribe the adhering membrane. The epoxy mixture can then be injected to fill the space between the basket and the membrane on the surface of the silicon rubber while preventing epoxy deposition on top of the membrane. The epoxy can then be hardened on a hot plate for a minute and completely cured in the oven for an additional 30 minutes at 110° C. after stripping-off the bottom silicon rubber film. Once the epoxy is cured the wires and electrodes can be fully insulated.

Wetting Procedure

In this embodiment, the cell culture wells can then be filled with 2 mL of ethanol, and the baskets placed in the filled wells after previously wetting the membrane outlet with a drop of ethanol that prevented air bubble formation at the membrane outlet. Ethanol fills the membrane in a few seconds up to the membrane inlet opening without trapping any bubbles in the microchannels, which can be verified by optical microscopy. The baskets can then be filled with ethanol, ensuring the continuity of the fluid between the source and sink reservoirs. Ethanol can then be replaced with deionized water (exchanged 2 times every 12 hours) and then finally substituted with PBS in the upstream and downstream reservoirs for 24 hours.

FITC-BSA Release Test

In this embodiment, a solution of FITC-BSA (Sigma-Aldrich) is prepared in PBS (pH 7.2, GIBCO) at a concentration of 10 mg/mL. Sodium azide (0.05% wt) can be added to the solution to prevent the growth of bacteria. 1.6 mL of PBS is loaded into the cell culture wells while 0.8 mL of solution is loaded into the basket inserts. The baskets can be capped with adhesive Teflon tape (Gore Gasket Tape). In this embodiment, two stainless steel (SS-316L) spheres can be added into each well to mix the sink solution, and the 12-well plate hermetically capped using the same Teflon tape. 1 and 2 VDC can be applied to a set of 3 replicates for each by means of stabilized DC power supplies (e.g., E3643A, Agilent Technologies). In this embodiment, no voltage is applied to an additional 3 baskets which were used as passive release controls. Finally, the plate can be stored in a black box in order to prevent photobleaching of the samples. The box can be placed on a rocker plate (VWR) causing the stainless steel spheres to constantly mix and homogenize the sink solution. At time intervals of approximately 3 days, 200 μL of the sink solution can be loaded into a 96-well plate. A fluorescence spectrophotometer (Fluostar Optima, BMG Labtech) can be utilized to measure their fluorescence. The samples can then be re-added to the cell culture wells, along with fresh PBS to compensate for evaporation from the well. In this embodiment, the release concentration of the sample is finally obtained through a fluorescence-concentration standard curve.

Results

Figure 14:
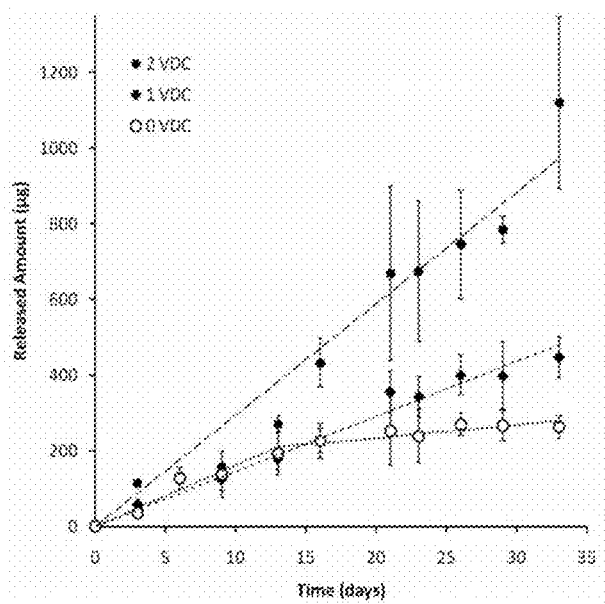
FIG. 14 illustrates the cumulative release of FITC-BSA through a nanochannel device.

FIG. 14 depicts the cumulative release of FITC-BSA through an NDD membrane at 11 different times over a 33 day period. The passive release of FITC-BSA shows a fast transient profile, which saturates to a much lower steady-state rate. This transient may be associated with attainment of the equilibration of the concentration gradient across the long structure of the membrane. Additionally, this may be due to a progressive reduction of the effective nanochannel cross-section related to the adsorption of FITC-BSA on the silica walls. BSA adsorption on silica substrates has indeed been widely documented[38-42] and reported to have an impact over release rates from smaller nanochannels (22 nm)[5]. The release rates while applying an electrical potential of 1 or 2VDC at the NDD electrodes are approximately 3.9 and 9.8 times higher than the passive release rate measured after the attainment of the concentration gradient equilibrium: 13.5 (at 1V) and 33.9 (at 2V) versus 3.5 (passive release) μg/day.

Figure 15:
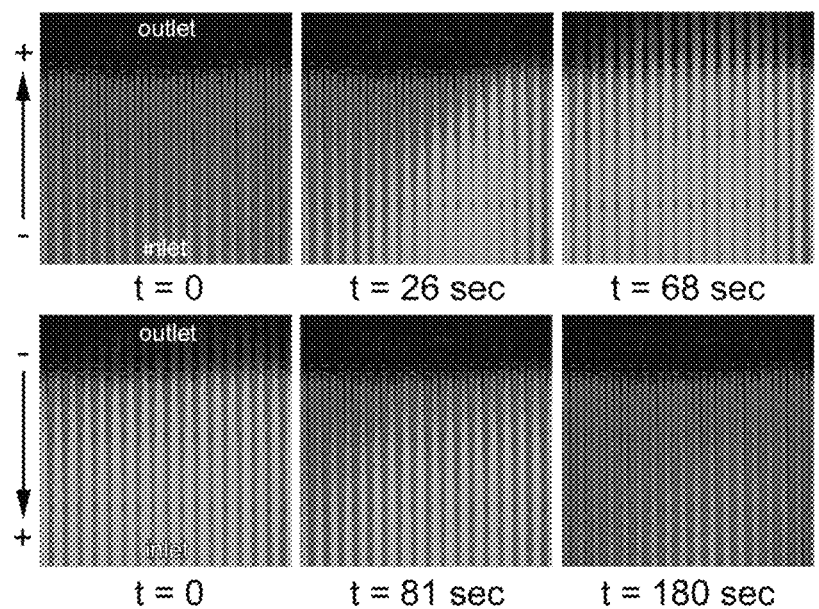
FIG. 15 illustrates fluorescent images of the electrokinetic transport of FITC-BSA under forward and reverse bias demonstrating reversibility of the electrokinetic flow. Fluorescent microscope images depicting FITC-BSA under both forward and reverse bias, demonstrating reversibility of the molecular transport.

FIG. 15 depicts fluorescent images of the electrokinetic transport of FITC-BSA under forward and reverse bias demonstrating reversibility of the electrokinetic flow.

Discussion

The integration of electrodes at the inlet and outlet of silicon based nanofluidic membranes is an important extension of this promising class of robust drug delivery architectures. The electrodes can be used to electrokinetically actuate and modulate the release of therapeutics at low applied voltage without the need of a pressure gradient generally applied to an intervening piston or flexible membrane[33,34]. Short electrode spacing yields high electric fields at voltages that induce minimal electrolysis at the electrode surface[43] (minimal electrolysis is required to maintain the ionic current). Complete flow reversal and low-power control of the release can be achieved from a membrane with a release rate of 34 μg/day at 2V that compares well with other optimized drug delivery architectures[5] and reaches the range of therapeutic interest not achievable with passive transport in a similarly designed system[44,45].

The experimental data were analyzed to understand the balance between the electrokinetic phenomenon of electrophoresis and electroosmosis. We determined the effective mobility of the system from the average amount of drug released per second, $1.57 \times 10^{-7}$ mg/s at 1V and $3.93 \times 10^{-7}$ mg/s at 2V. The average fluxes, 0.0147 mg/cm²s at 1V and 0.0369 mg/cm²s at 2V, were then obtained by dividing the average release rate by the cumulative cross-section of the outlet microchannels ($1.064 \times 10^3$ μm²). This was feasible considering that at steady-state the inlet and outlet fluxes must be equal. Maximum effective release velocities ($v_{\text{eff}}$) were calculated and equal to 14.7 μm/s at 1V and 36.9 μm/s at 2V, by dividing the fluxes by the initial concentration, 10 mg/mL[46]. Finally, an effective mobility ($\mu_{\text{eff}}$) was determined as[47]:

$$\mu_{\text{eff}} = \frac{v_{\text{eff}}}{E_x} \quad (1)$$

where $E_x$ is the externally applied electric field in the axial direction. In this context, simulations were performed to determine an appropriate value for $E_x$.

Figure 16:
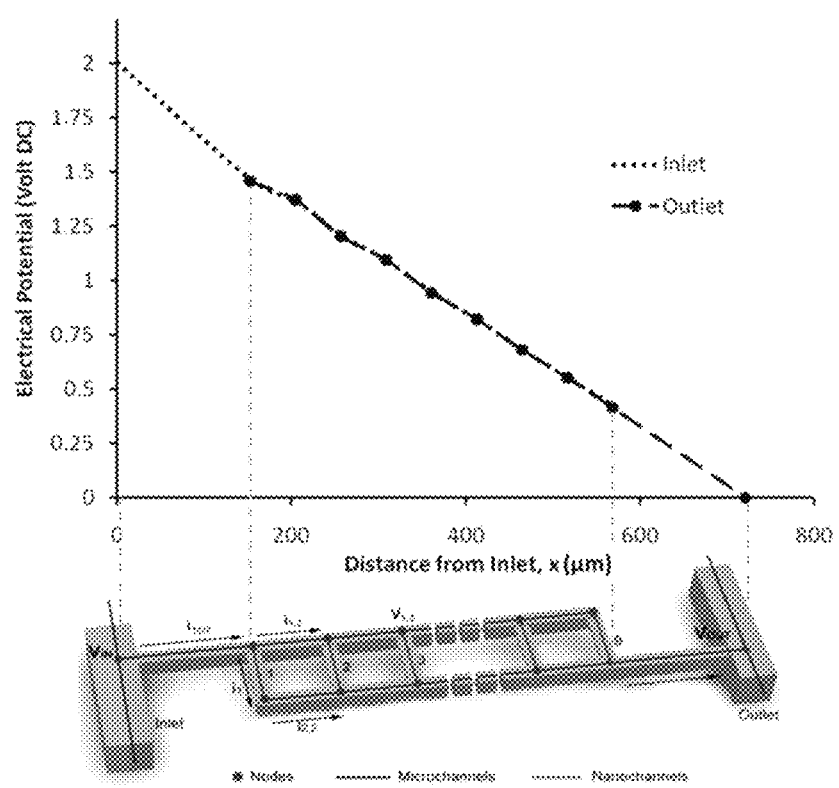
FIG. 16 illustrates a resistive network used to model the electrical properties of a nanochannel device fluidic system. Results of the numerical simulation of the resistive network used to model the fluidic system. Inset: The resistive network used in the model.

The inset of FIG. 16 shows the resistive network used to model the electrical properties of the fluidic system. Since the aqueous solutions used to subcutaneously administer pharmaceutical agents usually have high ionic strength to more closely match the in vivo physiological environment, the Debye length ($\lambda_D$) of the electrical double layer (EDL) is usually in the nanometer or sub-nanometer range, as determined by[48]:

$$\lambda_D = \sqrt{\frac{\varepsilon_r \varepsilon_o kT}{\Sigma_i N_A c_i z_i^2 e^2}} \quad (2)$$

where $\varepsilon_r$ is the relative dielectric constant of the solution, $\varepsilon_o$ is the permittivity of free space, k is Boltzmann's constant, T is temperature in Kelvin, $N_A$ is Avogadro's number, $c_i$ is the molar concentration of the ith ion, $z_i$ is the charge valence of the ith ion, and e is the elementary charge. The FITC-BSA used to characterize this electrokinetic delivery system was loaded in standard PBS buffer (137 mM NaCl, 2.7 mM KCl, 8 mM $Na_2HPO_4$, 2 mM $KH_2PO_4$[49]) resulting in a calculated $\lambda_D$ of 0.75 nm. Given such a thin EDL, the resistance (R) was treated as a common proportionality throughout all of the network branches. Thus an approximate geometrical resistance of each segment was obtained from:

$$R \approx \frac{L}{A} \quad (3)$$

where L is the length of the segment and A is the cross-sectional area. The voltage drop across each resistor in the network was then defined as a system of equations which was numerically solved (Matlab, The MathWorks, Inc.) The solution was declared convergent when the maximum residual for the variables became smaller than $10^{-9}$. Because of the short length of the nanochannels (5 μm) and their significant cross section (4.5 μm²) as compared to the microchannels (590 μm and 9.16 μm²), their overall contribution to the total resistance is relatively small. As shown in FIG. 12, this leads to a quasi-linear voltage drop across the whole system. $E_x$ can therefore be estimated by dividing the applied voltage by 725 μm, the longest path from inlet to outlet (assuming minimal contact resistance at the platinum electrodes). The calculated effective mobilities should be identical at each applied voltage. Effective mobility was $1.12 \times 10^{-4}$ cm²/Vs at 1V and $1.41 \times 10^{-4}$ cm²/Vs at 2V, which are in reasonable agreement.

The electroosmotic ($\mu_{eof}$) and electrophoretic ($\mu_{ep}$) mobilities relate to the effective mobility as[50]:

$$\mu_{\text{eff}} = \mu_{eof} + \mu_{ep} \quad (4)$$

Figure 17:
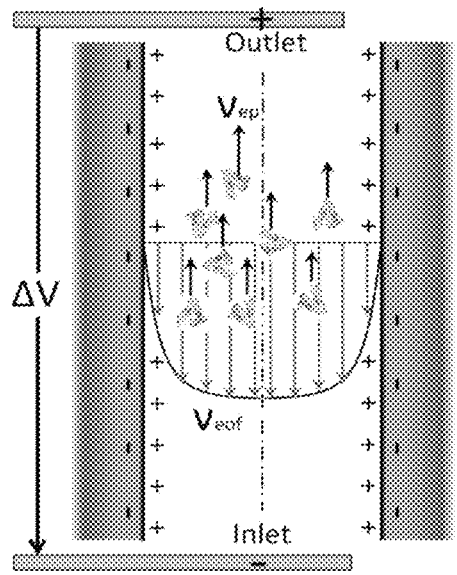
FIG. 17 illustrates a schematic of the balance between electroosmosis and electrophoresis.

Under the thin $\lambda_D$ approximation, the electroosmotic and electrophoretic mobilities can be calculated as[51]:

$$\mu_{eof} = \frac{\varepsilon_r \varepsilon_o \zeta}{\eta(T)} \text{ (Helmholtz-Smoluchowski equation)} \quad (5)$$

$$\mu_{ep} = \frac{q}{6\pi r \eta(T)} \quad (6)$$

where $\zeta$ is the zeta potential, $\eta$ is the viscosity (previously determined at room temperature to be 0.93 mPa·s for PBS buffer[52]), and r and q are the hydrodynamic radius and total charge of the FITC-BSA. Given that the silicon dioxide surface and the FITC-BSA have net negative charge, these calculated mobilities are expected to lead to velocities in opposite directions, as illustrated in FIG. 17. The zeta potential of the silicon dioxide surfaces that line the channel was then obtained using the Grahame equation[53]:

$$\sigma(\zeta) = \frac{2\varepsilon_r \varepsilon_o kT}{e \lambda_D} \sinh \frac{e\zeta}{2kT} \quad (7)$$

where $\sigma(\zeta)$ is the silicon dioxide surface charge, previously estimated at $-1$ $\mu C/cm^2$ [10]. From this equation a zeta potential of $-10.5$ mV was obtained. $\mu_{eof}$ was $7.997 \times 10^{-5}$ $cm^2/Vs$. This value represents a good approximation even given the complex architecture as it has been previously demonstrated that both electric fields and electroosmotic velocity fields have the ability to conform to complex geometries[54].

In this embodiment $\mu_{ep}$ was calculated as well using a FITC-BSA hydrodynamic radius of 6 nm[55]. The selection of the charge on this molecule was more complicated. A titration value indicating the maximum theoretical charge of $-11$ for BSA is available; however, shielding by the solvent plays a crucial role on the effective charge which produces the electromotive force in the presence of an electric field[56]. Estimated ratios of 7 to 10 FITC per BSA, with a theoretical charge of $-1$ for each FITC, have been reported in the literature[55]. Therefore the total charge on the molecule could theoretically approach $-18$ in pH 6.8 ($7^* -1 + -11$)[56,55]. However, such a charge results in an effective velocity which exceeds our experimentally determined values. The effective charge of BSA can also be as low as $-8.4$ in pH 6.8[56] and, similar to the zeta potential of the surfaces, can be further affected by ionic strength. A charge range between $-13$ and $-15$ is sufficient to lead to an electrophoretic mobility, between $-1.980 \times 10^{-4}$ and $-2.28 \times 10^{-4}$ $cm^2/Vs$ (sign based on electrical conduction convention), which in conjunction with the calculated electroosmotic mobility and equation 4, produces an effective mobility that agrees well with our experimental data.

The transmembrane current was also measured in pure PBS and determined to be 17 and 52 µA at 1 and 2 VDC, respectively. This equates to consumed powers of 17 and 104 µW, respectively, and compares quite favorably to other reported delivery architectures[33].

Although these calculations involve a number of approximations, they demonstrate a good agreement between theory and experimental analysis such that the rational design of highly controllable drug delivery architectures can be achieved. Furthermore, they elucidate the relative contributions of electrophoresis and electroosmosis to the electrokinetic transport. In the high ionic strength environment present in vivo, such considerations are crucial in deciding what drugs to deliver and how much power will be required. Future analysis would include thorough probing of the system parameters in the context of drug delivery as well as investigating new delivery constructs which can take further advantage of these phenomena that may lead to broader ranges in delivery rate and even lower operating powers.

Exemplary embodiments presented here have been characterized for cumulative long-term molecular release and release reversibility with FITC-BSA using fluorescent spectroscopy and microscopy. Furthermore, the relative contributions of electrophoresis and electroosmosis have been determined, and clinically relevant release rates have been observed. This architecture could ultimately allow for continuous modulation of drug release, a requirement for many emerging therapeutic regimes, including chronotherapy. This sustained rhythmic delivery could be attained with a pre-programmed control unit embedded in a powered implantable capsule. Additionally, such a system could include telemetry hardware for remote external control of the activation or modulation of the delivery regimen. Finally, the implant could incorporate sensors, capable of transducing environmental, physical and biological changes, with a logic unit regulating the administration of therapeutics, enabling the realization of artificial glands.

In addition to the preceding design and fabrication techniques, NDD devices can also be designed and fabricated according to methods and apparatus disclosed in U.S. Patent Publications U.S. Patent Publication 2007/0066138 ("Diffusion Delivery Systems and Methods of Fabrication") and U.S. Patent Publication 2010/0152699 ("Nanochanneled Device and Method of Fabrication"), incorporated herein by reference.

Nanochannel Delivery Systems with Electrodes

1 Fabrication Process for Exemplary Embodiment

Exemplary embodiments of nanochannel delivery systems with electrodes (NDSE) were composed of two primary components: a silicon substrate and a Pyrex cap with integrated electrodes.

1.1 Silicon Substrate Fabrication

In this embodiment, the processing of the silicon substrates was started with double side polished p-type 4 inch wafers. The first major process of silicon substrates was to define nanochannels. To fabricate the nanochannels, a pad oxide layer was deposited followed by a layer of nitride on wafers. Then, standard lithography was applied to generate nanochannel patterns. After that, CF4 reactive ion etching (RIE) was used to remove nitrides on these channel patterns. Etching time was controlled so that there was a thin layer of silicon dioxide remaining to prevent reactive ions from attacking the silicon underneath. A diluted HF solution was used to clean the oxide in channel patterns, Then, the silicon wafers were put into thermal oxide furnace and a desired amount of silicon oxide was grown, The thickness of oxide defined the height of nanochannels. The thickness of the oxide film was measured by using ellipsometry. HF solution was then used to remove all dielectrics on the substrates. A new layer of silicon nitride was deposited for the second major step to define the microchannels. Microchannels were patterned on top of nanochannels. Then, RIE was repeated. After that, KOH etching was performed to get 3 micron deep microchannels. The third major step was back side openings. A new layer of silicon nitride was deposited on the silicon substrates. The exit ports were patterned on back of the wafers by double side alignment. $CF_4$ RIE was used to open the exit port pattern. Then a through-wafer KOH etching was performed (approximately eight hours) to etch through silicon wafers. After removing dielectric materials using HF solution, a 15 nm thick silicon oxide layer was deposited as an insulating layer for easy wire bonding. The real nanochannel height was measured using AFM, 5 selected points were measured for each substrate.

1.2 Pyrex Glass Fabrication

An exemplary method of fabricating a Pyrex glass cap with electrodes is summarized here as an example. There were three major steps in the process. The first step was to derive electrodes. A sandwich of titanium, gold and titanium was evaporated on four inch Pyrex wafers. Then, standard lithography was used to pattern the electrodes. Multi-step wet etching was applied to etch the Ti—Au—Ti sandwich, and the remaining photoresist was then cleaned up. Here, the height of electrodes was 150 nm above the Pyrex surface. Then, a lift-off process was performed to match the thickness of electrode with evaporated Pyrex glass film, To do so, a photolithograph was performed to cover the electrodes followed by a 150 nm glass film evaporation using CHA. Next, the wafer was sonicated in acetone to remove the photoresist and clean the deposited Pyrex on the top of electrodes. After that, a 100 nm thick Pyrex film was evaporated to cover electrodes. Then, a CMP step was applied to polish the surface to reach desired roughness, and the CMP process was optimized. During the CMP process, many parameters such as pressure, speed, time, and pads, needed to be controlled. Many different fabrication techniques were tried with proper control of pressure, speed, time along with other parameters. The surface roughness was finally reduced to ~1 nm.

1.3 Layer Bonding

Holes were drilled in the Pyrex wafers and the anodic bonding was done using and EVG® 520. The bonding conditions are adjusted for different nanochannel height. After the bonding step, the wafers were cleaned, diced, and NDDE devices were delivered.

1.4 Membrane Cleaning

Five NDDE wafers were received from the fabrication group. All the membranes had to be cleaned to remove any fabrication residue before any type of testing. First, the silicone layer was removed from all the membranes. Then, the membranes were separated into groups of 10 and were put into plastic microtubes. The microtubes were filled with ethanol and were placed on a plate shaker for 30 minutes. After the time elapsed, the ethanol was removed and the membranes were separated on a petri dish. Finally, the petri dishes were placed in a vacuum oven at a 115° C. for the night to let the membranes to fully dry.

2 New NDDE Membrane Configuration Descriptions

Figure 18:
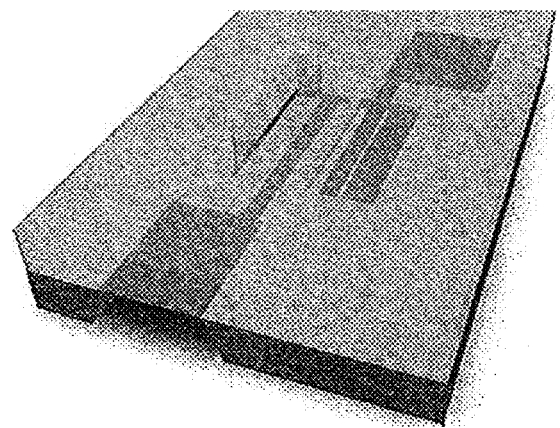
FIG. 18 illustrates a model of a nanochannel membrane.

There are eleven configurations for the new NDDE membranes. Each configuration differs in the number of electrodes and structural support pillars, type of microchannel and nanochannel structure, and the presence of electrodes inside the channels. FIG. 18 shows the simple layout of a membrane. The main difference between the new NDDE and the prior configurations is the addition of electrodes for active release.

Figure 19:
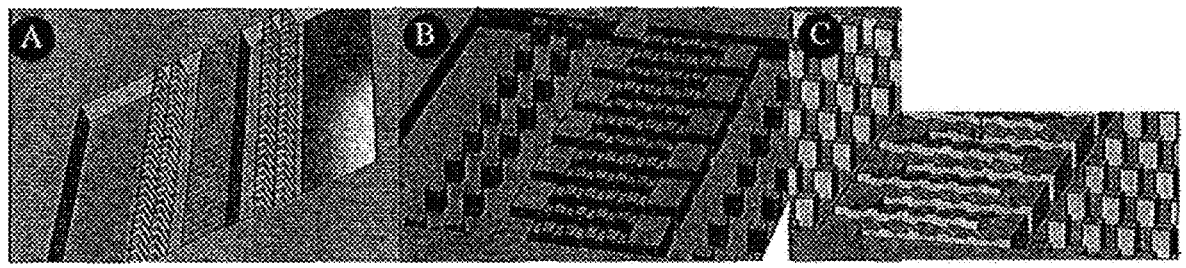
FIG. 19 illustrates a model of different nanochannel arrangements.

In these embodiments, there are three types of nanochannels, straight, perpendicular and tilted nanochannels. In the configurations with straight nanochannels, the fluid crosses directly from inlet to outlet. In the perpendicular channels, the inlet and outlet are not directly connected. The micro-channels and nanochannels are interdigitated. The same case occurs in the tilted nanochannels however the channels are in an angle. FIG. 19 shows these differences.

In these embodiments there are three configurations with straight nanochannels, configurations #1, 5 and 10. Configurations #1 and #5 each have two electrodes but differ in nanochannel length. Configuration #10 has a third electrode which lies across the middle of the channels. Three configurations have tilted nanochannels (#7, #8 and #9) and five configurations have perpendicular nanochannels (#2, #3, #4, #6 and #11). The nanochannels in configurations #2, 3 and 4 are shorter that those of configurations #6-9 and #11. As a result, there are more micro and nano scale channels in configurations #2, 3, and 4, Six configurations have 4 electrodes (#3-4, #6, #8-9 and #11). They are arranged as two pairs of opposing electrodes running along the longer dimension of the membrane. Configurations #9 and #11 have long nanochannels present on only one side of the microchannels. The information is summarized in Table 1 below.

| Configuration | # Electrodes | Channel Structure | # Pillars | Nanochannel Type | Electrodes Inside |
|---|---|---|---|---|---|
| 1 | 2 | straight | 3 | straight/short | NO |
| 2 | 2 | interdigit | 4 | perpendicular | NO |
| 3 | 4 | interdigit | 8 | perpendicular | NO |
| 4 | 4 | interdigit | 8 | perpendicular | YES |
| 5 | 2 | straight | 3 | straight/LONG | NO |
| 6 | 4 | interdigit | 8 | perpendicular/LONG | YES |
| 7 | 2 | interdigit | 4 | tilted/LONG | NO |
| 8 | 4 | interdigit | 8 | tilted/LONG | YES |
| 9 | 4 | interdigit | 8 | tilted/LONG/1 side only | YES |
| 10 | 3 | straight | 3 | straight/LONG | YES |
| 11 | 4 | straight | 8 | perpendicular/LONG/1 side | YES |

These images were taken after the gas testing was performed.

3 Membrane Characterization 3.1 AFM Measurements

The measurement of the nanochannel depth was performed through Atomic Force Microscopy (AFM) (Digital Instrument Dimension 3000, Columbus, Ohio). The measurements were performed on 4-5 different points of the wafer, located in different area of the wafer. The variation of the nanochannel size smaller that 2.62% was observed for each NDDE substrate.

3.2 Optical Microscopy

Prior to performing the gas testing, all membranes were washed in ethanol while being agitated on a plate shaker. After completely drying in an oven, they were selected by using an upright optical microscope. For the purpose of selecting the devices for further electro-osmosis testing, all membranes presenting visible defects (micro-sized) were discarded. The membranes screened were 20 nm without electrodes, 50 nm with and without electrodes, 100 nm with electrodes, and 150 nm with electrodes. The membranes without electrodes will be designated with "WO" while those with electrodes will be indicated with "W". In general for the varying nanochannel depths, configurations #3, 6, 7, 8, 9, 10 and 11 had a greater number of viable membranes compared to configurations #1, 2, 4 and 5.

First, the membranes were checked for visible or major defects such as over etching, broken edges and missing glass. About 62-75% of the membranes passed this inspection, The most common defect was over etching of the silicon—especially in the nanochannel area, in some membranes, there were large pinholes in the channels. These three major defects were randomly distributed within configurations and sizes.

The second inspection checked for dust particles in the channel area, membranes with bad contrast between anchor points and nanochannels, and problem with the attachments of the glass. In general, the configuration #2 and #3 had problems with contrast. It was hard to verify if the channels were present or not. For all nanochannel depths, configuration #4 exhibited over-deposition of electrodes. For depths 100 nm and 150 nm, no membranes were feasible for subsequent testing. At the end of the screening process, 68% of the 20 nm WO, 67% of the 50 nm WO, 63% of the 50 nm W, 74% of the 100 nm W and 71% of the 150 nm W were viable for further testing.

Also present were some defects that were characteristic to the membranes of the same nanochannel depth size. The inlets will refer to openings on the glass side and the outlets will refer to openings on the silicon side.

3.3 Electrode Resistance Test

The electrode resistance test was performed by measuring the resistance between two electrodes and between one electrode and the silicon surface to determine if there was an electrical connection between them. The membranes tested were 50 nm, 100 nm and 150 nm in depth. The configurations measured were #1, 2, 3, 4 (when applicable), 5, 6, 7, 8, and 10.

Figure 20:
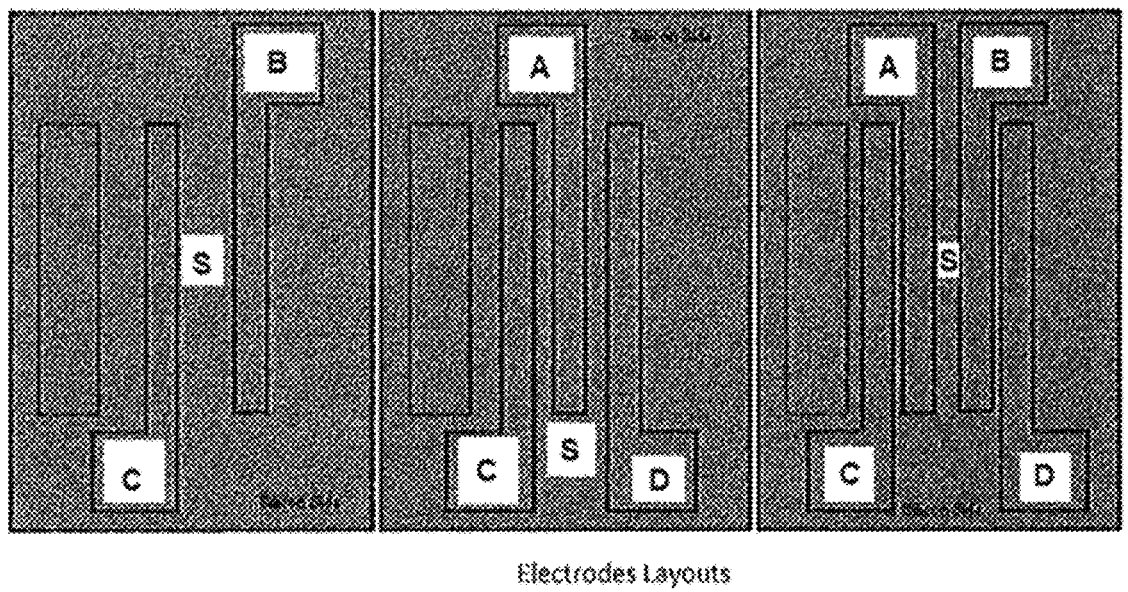
FIG. 20 illustrates schematics for different electrode layouts.

The designation of each electrode is presented in FIG. 20 shown below. For the membranes with only two electrodes, two resistance measurements were taken. First, the resistance was measured across electrodes B and C. Then, it was measured across electrode B and the silicon surface of the membrane. For the membranes with three electrodes, the resistances were measured across A-C, A-D, and electrode A and the silicon surface of the membrane. Finally, for membranes with four electrodes, the resistances were measured across A-B, A-C, B-D, A-D, and electrode A and the silicon surface of the membrane.

Two hundred and thirty-four membranes were measured. Each membrane had a resistance value greater than 1 M$\Omega$ between the electrodes. All of the membranes had a value greater than 60 M$\Omega$ (over the limit of the multimeter) between electrode A and the silicon surface of the membrane.

3.4 Gas Testing System

A custom gas testing system composed of a high purity nitrogen, $N_2$, tank (Research Purity Grade 99.9999%, Matheson Tri-Gas®), a dual stage pressure regulator (3120-580, Matheson Tri-Gas®), a membrane holder, a clamping system, a pressure transducer (Full Scale 200 psi, accuracy 0.05%, PX01C1-200G5T, Omegadyne Inc.), a gas filter (Matheson Trigas 200 nm) and a system of valves pipes and connections was designed in order to provide a testing apparatus for exemplary embodiments. The membrane holder was designed to assure effective sealing housing one NDDE and a silicon rubber custom seal (molded by Apple Rubber, Lancaster, N.Y., USA). It was made of a stainless steel SS316 machined rod and a mechanical clamp. The clamping system employs two opposite threaded rods which are forced against each other through an interposed nut.

3.4.1 Measuring Boundary Conditions

The zero voltage, $V_0$, was measured by the while the system was insulated from the gas tank and the pressure inside the system was 0 psi. The full-scale voltage, $V_{FS}$, was measured at the full-scale pressure, $P_{FS}$, of 200 psi. Previous gas pressure testing on older membrane versions were started at an initial pressure of roughly 45 psi. This corresponded to an initial voltage of 1.125V. The boundary conditions listed in Table 2 below were used to generate Equation 1, the linear equation relating voltage to pressure, where $V_1$ is the instantaneous voltage.

3.4.2 Gas Testing Procedure

First, a membrane was placed inside the grooves of the cylindrical silicon rubber seal. The seal was then placed into the threaded rod. Next, the rod was locked into place with a hexagonal nut. The separation distance was 37.00±0.05 mm. After the membrane was secured, the vacuum valve was opened briefly to remove any air from the system (absolute pressure 15.6 kPa). Once the vacuum valve was closed, the filtered N2 gas was allowed into the system until the handheld multimeter read 1.134+0.005V (corresponding to a pressure of about 0.31 MPa). After the system had become saturated with N2 gas, all valves were closed and the system was insulated from the gas tank at $t_0$=0 seconds. The system pressure drop due to the gas flow throughout the membrane was measured and the data were collected with a digital multimeter (model 34410A, Agilent Technologies, Santa Clara, Calif., USA) at 0.1 Hz for 600 seconds.

3.4.3 Gas Testing System Performance Test

3.4.3.1 Leakage Analysis

A series of tests were performed to ensure that any leakage inherent to the setup would not affect the repeatability and reproducibility of the system. First, the gas test was performed by replacing the silicon seal and membrane with a bulk silicon rubber disc. A second test was performed by using a bulk silicon chip (presenting same sizes as NDDE but without inlet and outlet port and without channels), to analyze the efficacy of the custom silicon seal. Both tests were in triplicate. The standard deviation STDEV of the replicates of the leakage test was calculated respect the mean of data. The percentage pressure drop is related to an initial $\Delta P=3.110^5$ Pa and was measured at the end of the test (elapsed time of 600 sec).

The noise of the pressure transducer was also measured. A noise <0.004% of the full scale (FS) value was observed which, in pressure, correspond to an absolute noise in the pressure measurement of 51 Pa (0.51 bar $10^{-3}$). The noise is comparable, in magnitude, to the pressure drop caused by the leakage. Thus, in both cases the leakage was considered negligible.

3.4.3.2 System Repeatability

The reproducibility of the system was also verified by performing the gas testing ten times with the same NDD device. The test was performed on 2 membranes that presented a "high" and "low" $N_2$ flow rate (NDSE 150 nm config. #2, NDDE 150 nm config. #5 respectively).

Figure 21:
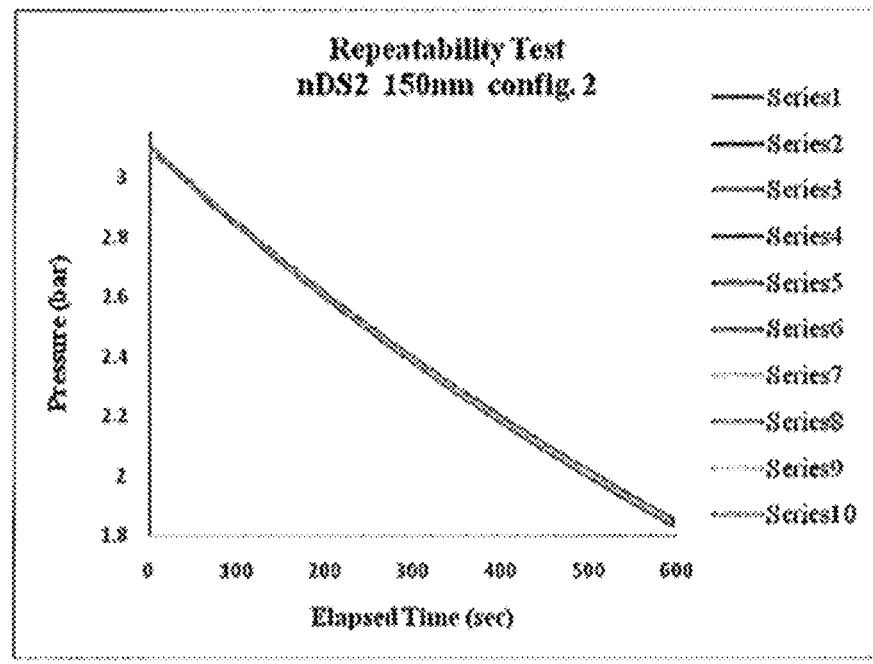
FIG. 21 illustrates a comparison of the experimental results for a specific nanochannel device configuration tested.

FIG. 21 shows the comparison of the experimental results for the NDDE 150 nm configuration #2. The standard deviation of data was found to be within the repeatability limit of the pressure transducer (±0.05% FS=6.8·$10^2$ Pa). The skew of the population of data was calculated to evaluate the normality of the data distribution. The values of the skew indicate that the data presents a small deviation from a Gaussian distribution.

3.4.4 Experimental Data Processing

The voltage data collected from the pressure transducer were converted into the corresponding pressure data through Equation 1. The pressure drop is well described by a single exponential decay, consistent with the solution to a one-dimensional transient problem. Thus, the collected pressure data were fitted to an exponential function, Equation 2, where D is the time constant.

$$P(t)=k*e^{-Dt} \qquad (2)$$

The interpolation to resample each curve was performed in a time range of 600 s and was started from a relative pressure of k=0.31 MPa. The maximum standard deviation, S, correlation coefficient, $R^2$, between experimental data, and the interpolated fitting curve were calculated for each tested NDDE configuration.

From the normalized data, each membrane can be characterized by D which is proportional to the gas flow rate of the membrane. The average time constant, $D_{AVG}$ was calculated for each distinct membrane configuration without excluding any outlier membranes. The average time constant based on the selection of membrane profiles that were most clustered together, $D_s$, was also calculated after excluding outlier data. The difference between the two averages can suggest the consistency of the data. The percentage standard deviation of the pressure data at t=600 seconds was calculated in relation to the starting pressure (0.31 Pa). Additionally, the skew of the data distribution was calculated. These values are listed in Table 10 together with the number of tested devices and the number of discarded membranes.

3.4.5 Results and Discussion

The first goal of the gas testing was to analyze the membrane structure to provide feedback on the fabrication process. The second goal was to select membranes most viable for further electro-osmosis testing.

Generally, the number of devices tested for each configuration was not sufficient to provide a complete statistical analysis. However, the values listed in Table X qualitatively suggest the range for selecting the most viable membranes. The configuration 4 for nanochannel depth of 100 and 150 nm were unavailable for testing.

Figure 22:
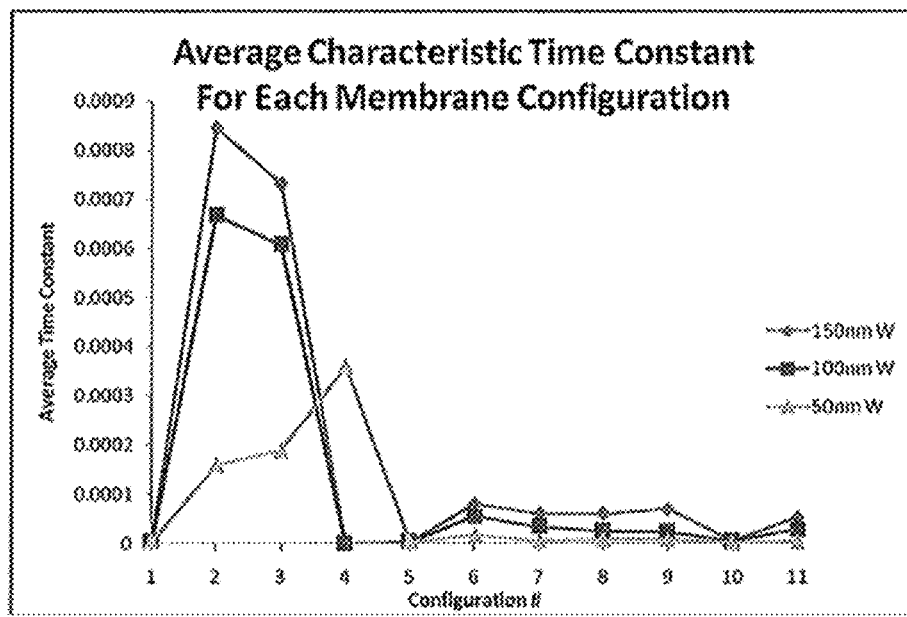
FIG. 22 illustrates a comparison of average time constant between the different configurations and nanochannel depths.

The gas flow was sensitive to differences in nanochannel depth and membrane configuration. FIG. 22 shows the comparison of average time constant $D_s$ between the different configurations and nanochannel depths. Configurations #2 and 3 showed the largest $D_s$ value for each of the nanochannel depths. This is due to the shorter length of the nanochannels and the larger number of interdigitated microchannels. Configuration #3's lower $D_s$ value in relation to configuration #2's is due to the extra micro-sized spacing between the inlet and outlet and the channel area. Configurations #6, 7, and 8 contained a fewer number of microchannels due to the increased length of the nanochannels. This caused a significant decrease in the $D_s$ value for these configurations with respect to configuration #2 and 3.

The three membrane configurations that contain only straight nanochannels, #1, 5, and 10, exhibited an extremely low gas flow rate. This is in agreement with the significantly smaller cross-sectional channel area with respect to other configurations (approximately 2-3 orders of magnitude). For these membranes, the pressure range detected by the gas testing is the same order of magnitude of the repeatability range of the pressure transducer (+0.05% FS=6.9 mBar). Thus, the results related to these configurations are not reliable for the purpose of selection. For this reason, the gas testing system needs to be modified by drastically decreasing the volume of the system reservoir.

4 NDDE Electro-Osmosis Testing 4.1 Testing Inserts Assembly

In order to perform the electro-osmosis (EO) test the NDDE were wired and assembled into a testing device. The testing device is composed by a cell culture basket and a cell culture well.

Figure 23:
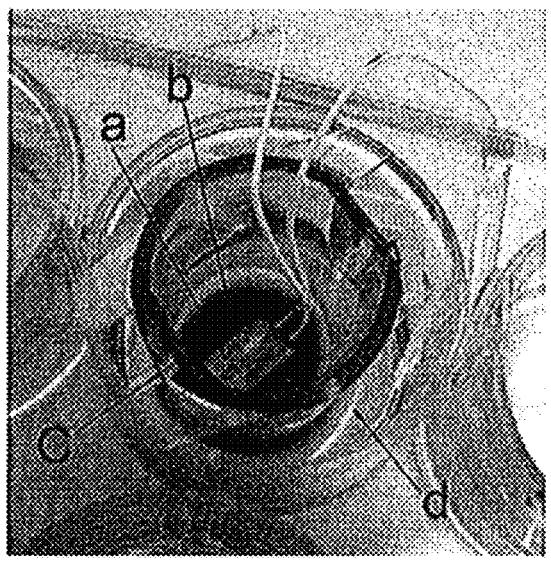
FIG. 23 illustrates a nanochannel device testing fixture.

FIG. 23 shows the picture of one testing fixture. The membrane is assembled into the cell culture basket by using epoxy glue. The basket, which works as solution reservoir, is placed into the well which contains the sink solution.

4.1.1 Wire Bonding

Figure 24:
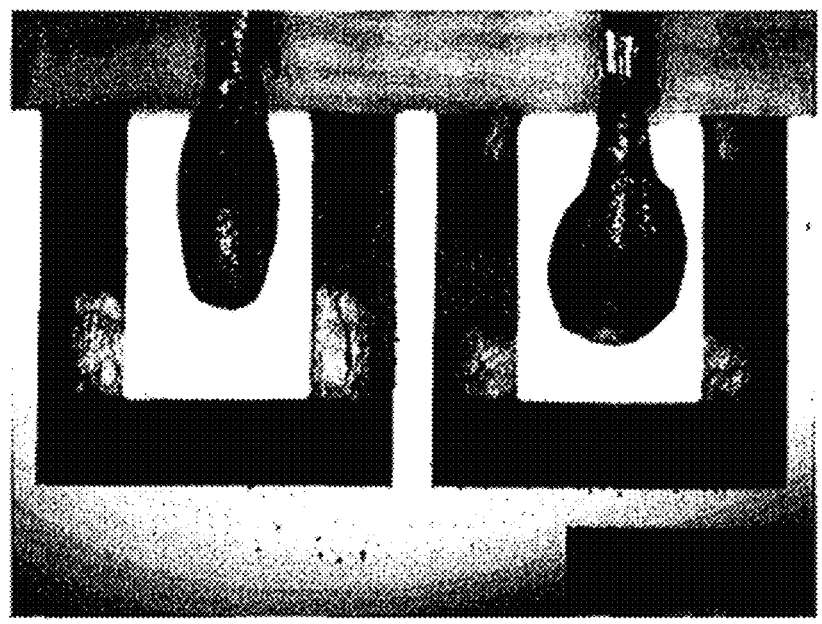
FIG. 24 illustrates a bonding spot on an nanochannel device electrode used in the testing fixture of FIG. 23.

The NDDE membranes were assembled by bonding conductive wires to the electrodes through EPO-TEK® H20E glue. EPO-TEK® H20E is a two component, 100% solids silver-filled conductive epoxy. To prepare the epoxy, a mix ratio by weight of 1:1 (Part A:Part B) was mixed. Five centimeters wires were cut and the ends were stripped out. A small drop of epoxy mixture was added to the wire and bonded to the electrode. The wire was positioned in the middle of the electrodes although the silicon surface was oxidized to achieve electrical insulation. FIG. 24 shows the bonding spot on an NDDE electrode. The membrane was verified that no conductive epoxy touched the diced sides of the membrane. The membrane was cured for 15 minutes on a hot plate at 120° C. Finally, it was baked in the oven at 110° C. for at least 1 hour.

4.1.2 Basket Preparation

Figure 25:
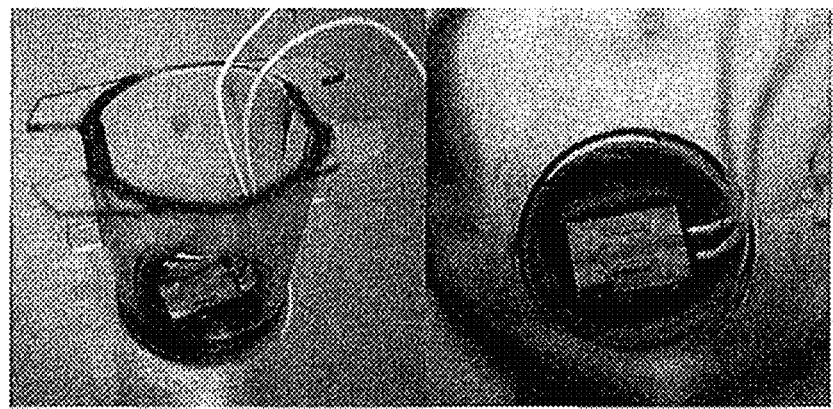
FIG. 25 illustrates a component used in the nanochannel device testing fixture of FIG. 23.

The NDDE was assembled into the basket by using EPOTEK® 353ND epoxy glue. EPO-TEK® 353ND is a two component, high temperature epoxy. To prepare the epoxy, a mix ratio by weight of 10:1 (Part A:Part B) was mixed. The epoxy mixture was loaded to a syringe with a 19½ G needle. The sharp tip of the needle was flattened preventing any damages on the membranes and optimizing the epoxy injection into the cell culture baskets. The baskets are commercially available for cell culture use. They present a polymeric membrane at the bottom of the basket. The membrane was removed from the basket and the insert was placed on the silicon rubber square around a membrane. The epoxy mixture was injected in the basket around the membrane, filling the silicon rubber surface (no epoxy was added on top of the membrane). The wires were carefully coated with the epoxy glue in order to create a sealing for the fluid and the electric insulation. The culture insert was hold down for a minute or until the epoxy was heat cured to amber color. Any air bubbles were removed during the curing procedure. The glass plate was left on the hot plate for more than 5 minutes to completely cure the epoxy. After the epoxy hardened, the baskets were removed from the silicone square, if the epoxy did not fill the electrode space, drops of epoxy were applied in the empty spaces and the basket was baked in the oven for additional 30 minutes at 110° C. Finally, the masking tape was removed from the silicon. FIG. 25 shows an assembled basket.

4.2 Wetting Procedures

Prior to run the electro-osmosis testing the membrane were filled (membrane wetting) with the solvent used during the following experiment. The wetting was performed by using different procedures.

4.2.1 PBS Wetting

The baskets were filled with 800 µL of PBS and placed in a 12-well plate. The PBS was left to wet the membrane by capillary filling. The outlet of each membrane was open to the air. The membrane were left to wet. After 24 hours the membranes were checked at the optical microscope. The wetting was found not to be complete. In particular the outlet area with supporting pillars was completely dry for all NDDE devices. It was found that the PBS cannot wet the membrane were the outlet microchannels are connected to the large opening which connect to the outlet. Additionally some bubbles were found in the micro-nanochannels area.

4.2.2 PBS+Vacuum

In order to aid the NDDE wetting with PBS vacuum was applied on the outlet side of the membranes. The vacuum was kept at 20 in Hg for 12 hours. The amount wet area was observed by optical microscopy. The application of a vacuum helped to further the amount of wetting by the PBS. Large parts of the outlet areas presenting the pillars were filled. However, many of the NDDE still exhibited a number of unfilled areas in both the channel region and outlet areas. In conclusion, the employment of vacuum did not sufficiently aid the NDDE wetting with PBS.

4.2.3 PBS+Vacuum+Electroosmosis

Figure 26:
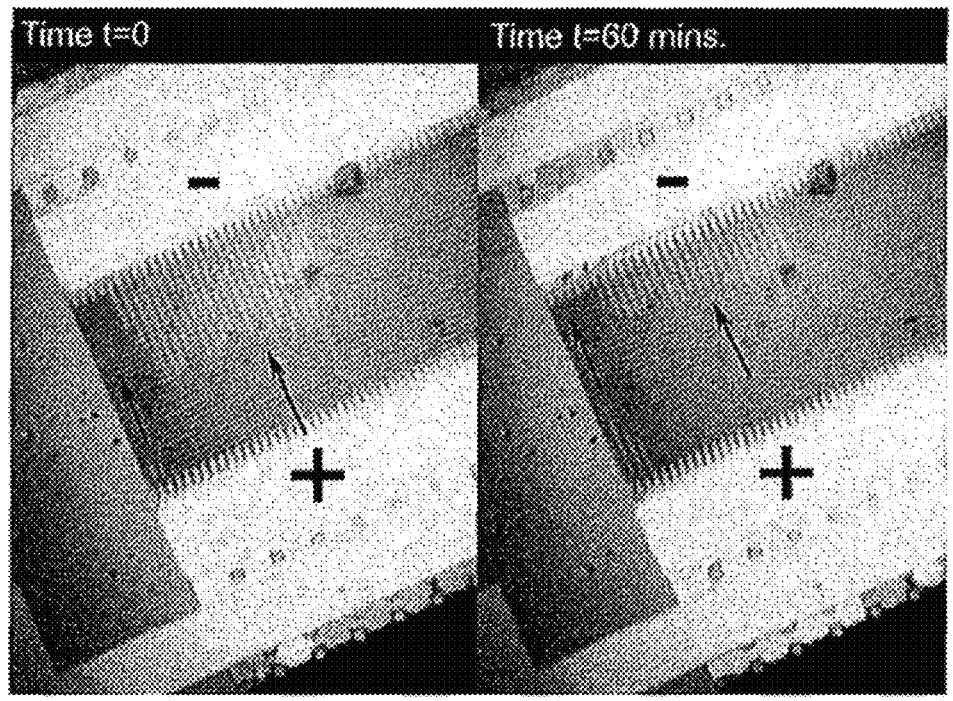
FIG. 26 illustrates the effect of the electroosmotic transport on the motion of air bubbles entrapped inside microchannels of a nanochannel device.

A difference in electrical potential of 1 Volt was applied between the electrodes of the NDDE membranes to analyze if the electroosmotic flow could be used in the wetting procedure. The motion of air bubbles entrapped inside the microchannels was observed suggesting a corresponding motion of PBS in the surrounding micro-nanochannels area. FIG. 26 shows the effect of the electroosmotic transport on the bubble motion over an interval of time of 60 minutes. The Voltage was kept constant for 12 hours. At the end of this procedure the membrane wetting was still not complete. In conclusion, Although the motion of fluid was observed as result of the applied electrical field, the complete NDDE wetting would be time consuming.

4.2.4 Ethanol, DI Water and PBS

The direct wetting with PBS was proven to be inefficient. For this reason, a different wetting procedure was employed for other NDDE membranes. The cell culture wells were filled with 2 ml of ethanol. The baskets were placed in the filled wells by previously wetting the membrane outlet with a drop of ethanol. This step avoided air bubbles in the membrane outlet. The ethanol filled the membrane in few seconds reaching the membrane inlet opening. After verifying the complete wetting through the optical microscope, the baskets were filled with ethanol, ensuring the continuity of the fluid between the basket reservoir and the well fluid, By using the optical microscope it was verified no bubbles were entrapped inside the membranes. The ethanol in the baskets and the wells was replaced with DI water which was replaced 2 times every 12 hours. Twenty-four hours were required to allow the ethanol to diffuse out of the membrane and be replaced by the DI water. The water was then replaced with PBS with was left in the upstream and downstream reservoirs for 24 hours. The intermediate step of DI water was necessary to avoid the salt precipitation from PBS in direct contact with ethanol. In conclusion, the ethanol wetting procedure guaranteed an immediate and complete wetting of the NDDE membranes.

4.2.5 BSA-FITC Standard Curve

The purpose of this experiment was to determine the standard curve of BSA-FITC conjugated (SIGMA ALDRICH) from serial and non-serial dilutions. The initial solution of BSA-FITC was prepared at a concentration of 10 mg/mL 181.48 mg of BSA-FITC were added to 18.148 mL of the buffer solution (PBS (GIBCO) pH 7.2 calcium chloride+0.05% wt sodium azide). A starting solution of 1 mg/mL BSA-FITC was made by 1:10 dilution of the 10 mg/mL BSA-FITC solution.

The standard curve was prepared by serial dilutions (iterative dilutions) and non-serial dilutions (from the 1 mg/mL BSA-FITC starting solution). Table 3 shows the thirteen solutions prepared for the non-serial dilutions. It includes the dilution ratio, the amount of BSA-FITC solution and the buffer solution and the final concentration.

TABLE 3

Non-serial Dilution Chat starting with a 1 mg/mL BSA-FITC solution

| Dilution | BSA-FITC Solution (uL) | PBS Solution (uL) | Conc (ug/mL) |
| --- | --- | --- | --- |
| 1:2 | 200 | 200 | 500 |
| 1:2.5 | 200 | 300 | 400 |
| 1:3 | 150 | 300 | 333 |
| 1:5 | 200 | 800 | 200 |
| 1:6.6 | 60 | 336 | 151.5 |
| 1:10 | 40 | 360 | 100 |
| 1:20 | 50 | 950 | 50 |
| 1:40 | 10 | 390 | 25 |
| 1:100 | 10 | 990 | 10 |
| 1:125 | 5 | 620 | 8 |
| 1:200 | 5 | 995 | 5 |
| 1:400 | 2.5 | 997.5 | 2.5 |
| 1:1000 | 1 | 999 | 1 |

Table 4 illustrates the three dilution sequences employed preparing the serial dilutions. Table 5 describes the three sequences by listing the amount of BSA-FITC solution, amount of buffer solution, amount of solution taken from previous dilution, the total amount of solution and its concentration.

TABLE 4

Sequences for Serial Dilutions

| Serial Path # | Concentration (ug/mL) |
| --- | --- |
| 1 | 500 → 333 → 151.5 |
| 2 | 400 → 200 → 100 → 50 → 25 → 10 → 5 → 2.5 → 1 |
| 3 | 15.873 |

TABLE 5

Serial Dilutions starting with a 1 mg/mL BSA-FITC solution

| Serial Path # | BSA-FITC Solution (uL) | PBS Solution (uL) | Taken from previous solution (uL) | Total (uL) | Conc (ug/ml) |
| --- | --- | --- | --- | --- | --- |
| 1 | 100 | 100 | 0 | 200 | 500 |
|  | 0 | 50 | 100 | 150 | 333 |
|  | 0 | 60 | 50 | 110 | 151.5 |
| 2 | 400 | 600 | 0 | 1000 | 400 |
|  | 0 | 100 | 100 | 200 | 200 |
|  | 0 | 100 | 100 | 200 | 100 |
|  | 0 | 100 | 100 | 200 | 50 |
|  | 0 | 100 | 100 | 200 | 25 |
|  | 0 | 150 | 100 | 250 | 10 |
|  | 0 | 100 | 100 | 200 | 5 |
|  | 0 | 100 | 100 | 200 | 2.5 |
|  | 0 | 150 | 100 | 250 | 1 |
| 3 | 10 | 620 | 0 | 630 | 15.873 |

A FLUOstar OPTIMA spectrophotometer (BMG LABTECH) was utilized to measure the fluorescence of the samples. Table 6 below shows the settings of the spectrophotometer that were used to perform the measurement. Triplicates of both serial and non-serial standard curve samples were prepared and measured. 100 uL was added into each.

TABLE 6

| Specifications of spectrophotometer | |
| --- | --- |
| Emission Filter | 485 |
| Excitation Filter | 520 |
| Gain | 735 |
| Optic | Bottom |
| Microplate | Greiner 96 F-Bottom |
| Positioning delay | 0.2 s |

The collected fluorescence data were fitted to an exponential function $$f = k(1 - e^{-dc}) \quad (1)$$

The inverse function $f^1$ was calculated to correlate the fluorescence intensity of the samples with the sample concentration. The expression of $f^1$ is $$c = -\frac{1}{d}\log\left(1 - \frac{f}{k}\right) \quad (2)$$

Figure 27:
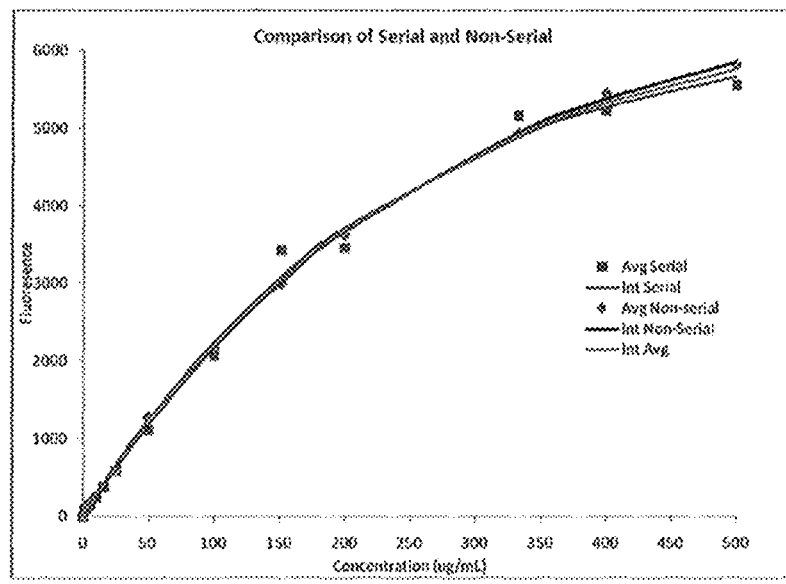
FIG. 27 illustrates a comparison between the interpolated fitting curve of fluorescence versus concentration for serial and non-serial dilutions in a nanochannel device.

The average of the fluorescence values of the triplicate of standard curve was calculated. The exponential fitting of the average was calculated for both serial and non-serial standard curve. The correlation coefficient, R, and the percent standard deviation of the fitting curve with respect to the average of the triplicates were calculated for both serial and non-serial dilutions. Generally the fluorescence results for the standard curve triplicates show a smaller standard deviation than 5%. Only exceptions were observed at small concentration for serial dilution where multiple dilutions can introduce larger errors. The fitting curves for serial and non-serial standards display a percentage deviation respect the experimental data smaller than 10% for concentration higher than 5 ug/tnL Nevertheless the measurements of non-serial diluted samples show larger scattering. For low concentrations serial dilutions are more accurate than non-serial dilutions because the amount of BSA-FITC solution initially added is small compared to the total solution. Larger variations were also observed for concentrations smaller than 5 ug/mL Generally agreement between standard curves prepared with serial and non-serial dilutions was found. Table 7 and FIG. 27 illustrate the comparison between the interpolated fitting curve of the serial and non-serial dilutions. The average of the fitting curve was chosen as the final standard deviation curve for BSA-FITC samples. The percent standard deviation of the interpolated fitting curve with respect to the average of both interpolated fitting curves was calculated.

TABLE 7

Comparison between serial and non-serial interpolated curves

| Conc (ug/ml) | INTNS | INTS | Average | % STDEV INT-AVG |
| --- | --- | --- | --- | --- |
| 500 | 5853 | 5666 | 5760 | 2.3 |
| 400 | 5380 | 5269 | 5325 | 1.5 |
| 333 | 4946 | 4889 | 4917 | 0.8 |
| 200 | 3672 | 3711 | 3691 | 0.7 |
| 151.5 | 3020 | 3082 | 3051 | 1.4 |
| 100 | 2183 | 2252 | 2217 | 2.2 |
| 50 | 1196 | 1247 | 1221 | 3.0 |
| 25 | 626 | 657 | 642 | 3.4 |
| 10 | 258 | 272 | 265 | 3.7 |
| 15.873 | | 426 | 426 | |
| 8 | 207 | | 207 | |

TABLE 7-continued

Comparison between serial and non-serial interpolated curves

| Conc (ug/ml) | INTNS | INTS | Average | % STDEV INT-AVG |
| --- | --- | --- | --- | --- |
| 5 | 130 | 137 | 134 | 3.8 |
| 2.5 | 65 | 69 | 67 | 3.8 |
| 1 | 26 | 28 | 27 | 3.9 |
| 0 | 0 | 0 | 0 | 1.0 |

In conclusion, the relation between concentration and fluorescence is expressed by the formula:

$$c = -\frac{1}{0.0040784}\log\left(1 - \frac{f}{6620.428}\right)$$

where the calculated coefficients d and k are introduced.

4.3 4.4 Electroosmosis Testing

The electro-osmotic (EO) transport in micro-nanochannels is strongly influenced by parameters related to the membrane structure and surface properties as well as parameters related to the chemistry of the solutions, in particular the parameters that strongly affect the transport are:

Applied Voltage (DC or AC)
Shape, Ratio and Frequency of the AC Voltage-Channel size
Electrodes position as referred to the channels position
pH of the buffer solution.

The aim of the test described in the following paragraphs is to quantify the influence of the above parameters to provide insight on the control of the electro-osmotic transport.

4.4.1 TEST 1. Electroosmotic Transport of BSA-FITC.

4.4.1.1 The aim of this test is to obtain preliminary results related to the influence of channel size, applied DC voltage, and electrodes configuration over the EO transport, In order to perform this test 14 membranes were selected:

| 6 | NDSE 50#3, |
| --- | --- |
| 2 | NDSE 50#4, |
| 3 | NDSE 100#3, |
| 3 | NDSE 150#3, |

The membranes were selected through optical microscopy and gas testing as previously described. The following Table 8 summarizes the test setup, displaying the testing configuration.

TABLE 8

Test setup. Number of membranes employed for each testing configuration. The table lists the number of membrane employed in the Voltage effect test, the electrodes configuration test and the nanochannels size effect test

| nDS2 config. | Passive (0 Volt) | 0.9 VDC | 1.8 VDC |
| --- | --- | --- | --- |
| 50#3 | 2 | 2 | 2 |
| 50#4 | | | 2 |
| 100#3 | | | 3 |
| 150#3 | | | 3 |

As shown in Table 8 above, the effect of the applied voltage over the EO transport was evaluated by comparing the passive BSA-FITC diffusion (2 replicates) with the active transport 0.9 VDC (2 replicates) and 1.8 VDC (2 replicates).

In order to evaluate the effect of the electrodes configuration 2 membranes of configuration #3 and 2 membranes presenting configuration #4 were selected. The NDDE #3 presents the same channel structure as NDDE #4. However, while the electrodes of NDDE #3 are placed in the inlet and outlet areas, the NDDE #4 electrodes cover the entire top surface of the interdigitated microchannels. For this reason 2 NDDE 50 #4 were selected to be compared with the NDDE 50 #3. The nanochannel size effect was evaluated by testing NDDE #3 for the nanochannels size 50, 100 and 150 nm.

4.4.1.2 Results and Discussion Test 1

Applied DC Voltage.

Figure 28:
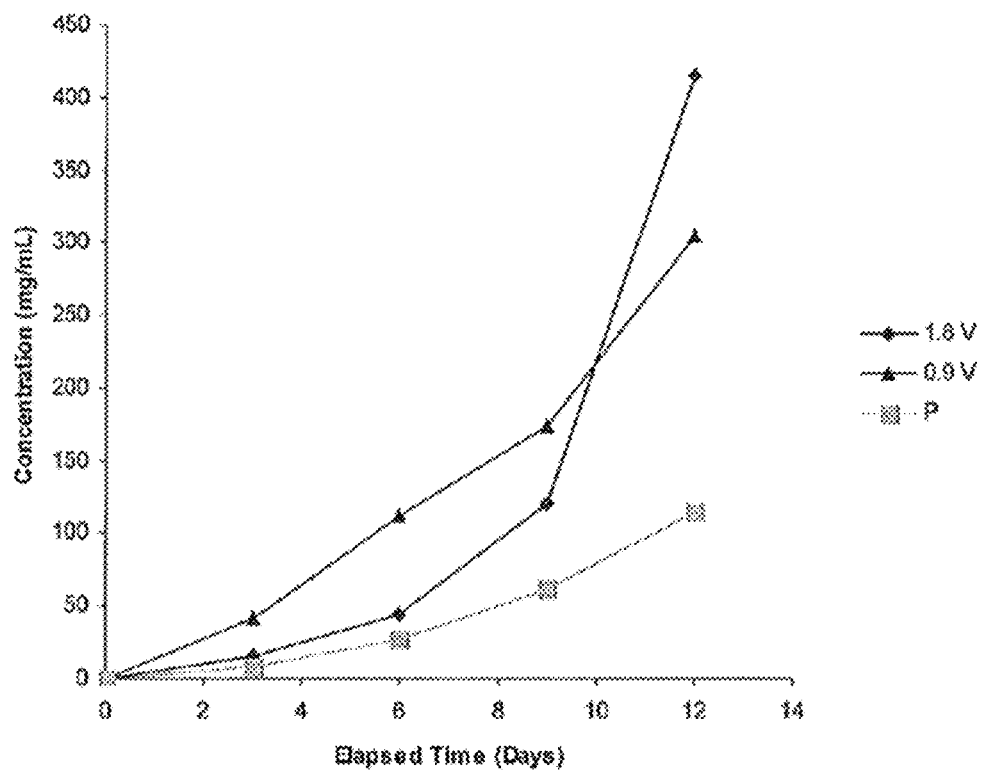
FIGS. 28-33 illustrate graphs indicating BSA-FITC released from nanochannel devices over time.

The results (over 12 days) of the active release of BSA-FITC throughout NDDE 100 #3 membranes are shown in FIG. 28. The figure shows the cumulative release curves for 1.8 and 0.9 applied Volts as compared to the cumulative passive release. A significant difference among the active and passive release rate was found. In particular an increase in the released amount of approximately 300% and 400% was measured at 0.9 and 1.8 applied Volts, respectively. For each testing configuration, the release rate of BSA-FITC increases over the elapsed time. The increase in the release rate is significant for the case of 1.8 applied Volts. Indeed the release rate for 1.8 applied Volts results smaller than for 0.9 applied Volts for the first 9 days of testing. The results show the clear effect of the applied voltage over the release rate of the membrane. However, due to the small number of replicates and the large standard deviation of data (approximately 30% of measured data) the results can only be considered qualitative.

Figure 29:
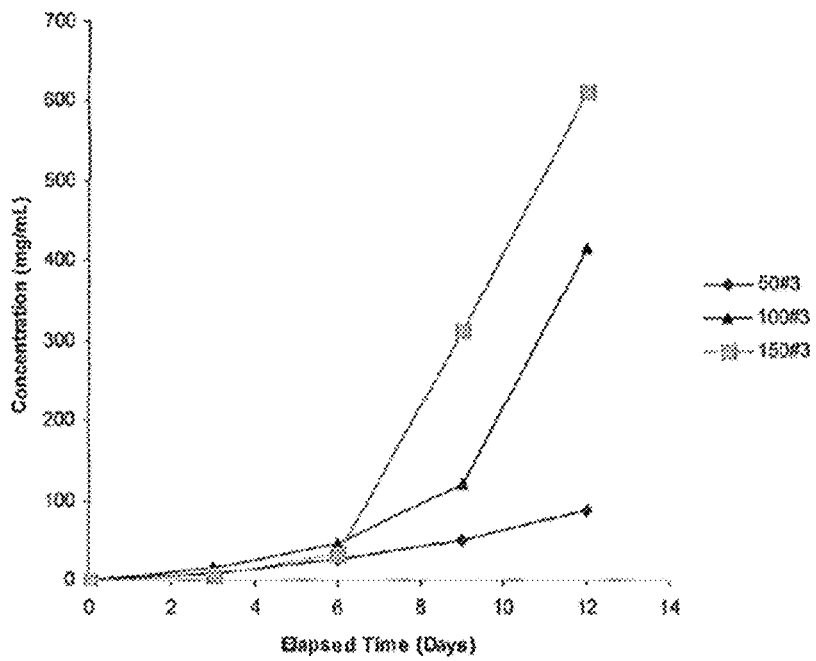

Effect of Channel Size,

The comparison of the active cumulative release (over 12 days) BSA-FITC throughout NDDE 50 #3, 100 #3, 150 #3 membranes is shown in FIG. 29. The results show that by applying the same voltage (1.8 Volts) the cumulative release increases at increasing nanochannel size. In particular if compared to the release results of NDDE 50 #3, an increase of approximately 400% and 600% was measured for the membranes presenting 100 nm and 150 nm nanochannels. As previously described, for each testing configuration the release rate of BSA-FITC increases over the elapsed time. A significant increase was measured after the sixth day of experimental testing. The results show the clear effect of the nanochannel size over the release rate of the membrane. However, due to the small number of replicates and the large standard deviation of data (approximately 30% of measured data) the results can only be considered qualitative.

Effect of Electrodes Configuration.

Figure 30:
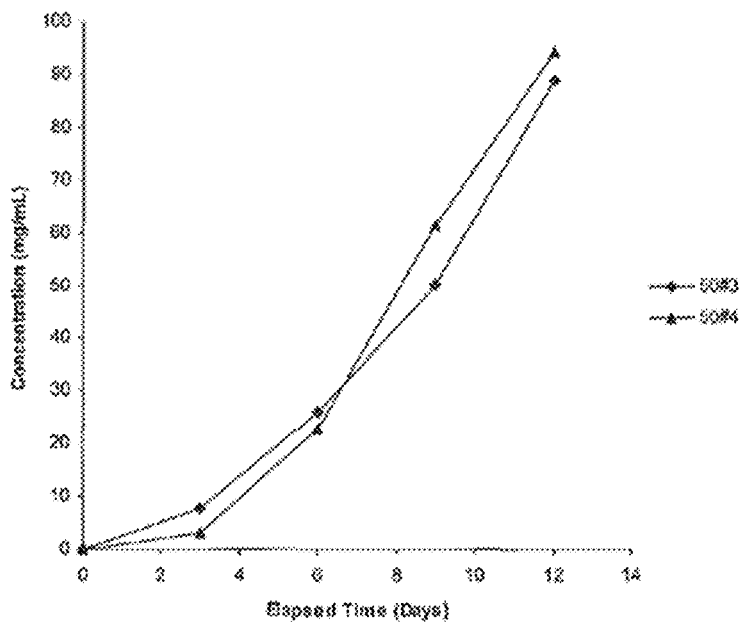

The analysis of the effect of the electrodes configuration over the release rate of BSA-FITC was performed by testing the 1.8 Volts active release of NDDE 50 #3 (electrodes in the inlet and outlet area) and NDDE 50 #4 (electrodes in the microchannels). The results (over a period of 12 days) are shown in FIG. 30. As shown in FIG. 30, no significant difference in the cumulative results was measured. The release seems not to be affected by different electrode configuration. Due to the small number of replicates and the large standard deviation of data (approximately 40% of measured data) the results can only be considered qualitative.

4.4.2 Test 2. Electro-Osmotic Transport of BSA-FITC 4.4.2.1 The aim of this test is to repeat the TEST 1 (above) with different NDDE configurations analyzing the influence of channel size, applied DC voltage, and electrodes configuration over the EO transport, in order to perform this test 17 membranes were selected:

| 9 | NDSE 150#7, |
| 2 | NDSE 150#8, |
| 3 | NDSE 100#7, |
| 3 | NDSE 50#7. |

The membranes were selected through optical microscopy and gas testing as previously described. The following Table 9 summarizes the test setup, displaying the testing configuration.

TABLE 9

Test setup. Number of membranes employed for each testing configuration. The table lists the number of membrane employed in the voltage effect test, the electrodes configuration test and the nanochannels size effect test.

| nDS2 Config. | P | 0.9 V | 1.8 V |
|---|---|---|---|
| 150 # 7 | 3 | 3 | 3 |
| 150 # 8 |   |   | 2 |
| 100 # 7 |   |   | 3 |
| 50 # 7 |   |   | 3 |

As shown in the table the effect of the applied voltage over the EO transport was evaluated by comparing the passive BSA-FITC diffusion (3 replicates) with the active transport 0.9 VDC (3 replicates) and 1.8 VDC (3 replicates).

In order to evaluate the effect of the electrodes configuration 3 membranes of configuration #4 and 2 membranes presenting configuration #8 were selected. The NDDE #7 presents the same channel structure as NDDE #8. However, while the electrodes of NDDE #7 are placed in the inlet and outlet areas, the NDDE #8 electrodes cover the entire top surface of the interdigitated microchannels. For this reason 2 NDDE 150 #8 were selected to be compared with the NDDE 150 #7. The nanochannel size effect was evaluated by testing NDDE #7 for the nanochannels size 50,100 and 150 nm.

4.4.2.2 Test 2. Results and Discussion

Applied DC Voltage.

Figure 31:
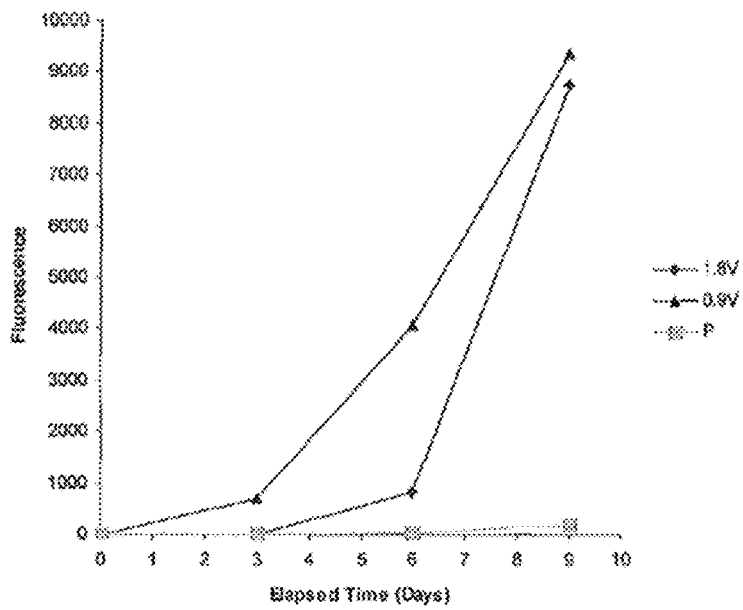

The results (over 9 days) of the active release of BSA-FITC throughout NDDE 150 #7 membranes are shown in FIG. 31. The figure shows the cumulative release curves for 1.8 and 0.9 applied Volts as compared to the cumulative passive release. A significant difference among the active and passive release rate was found. In particular after 9 days of experimental analysis the released amount for 0.9 and 1.8 Volts active release is approximately 45 times larger than the passive released amount. Also in this case, the release rate of BSA-FITC increases over the elapsed time for each testing configuration. The increase in the release rate is again more significant for the case of 1.8 applied Volts. However the overall released amount for 0.9 applied Volts results larger than the amount released by applying 1.8 Volts. Similar result was found in the TEST 1. Although the effect of the applied voltage is clear, due to the small number of replicates and the large standard deviation of data (approximately 35% of measured data) the results can only be considered qualitative.

Effect of Channel Size.

Figure 32:
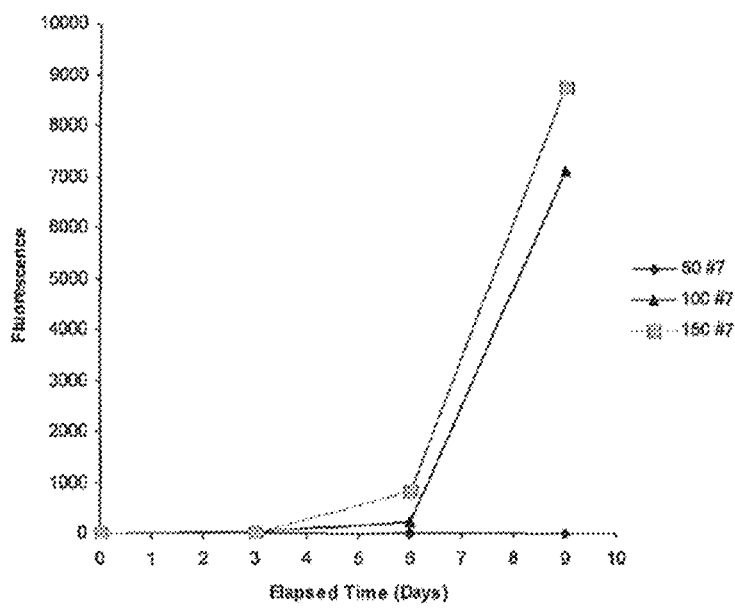

The comparison of the active cumulative release (over 12 days) BSA-FITC throughout NDDE 50 #7; 100 #7, 150 #7 membranes is shown in FIG. 32. The results show that by applying the same voltage (1.8 Volts) the cumulative release increases at increasing nanochannel size. In this case, by comparing the release data for NDDE 100 #7 and NDDE 150 #7 result two orders of magnitude larger than the results for NDDE 50 #7. As previously described, for each testing configuration the release rate of BSA-FITC increases over the elapsed time, and the significant increase occurs at approximately six days from the beginning of the test. The results show a proportional effect of the nanochannel! size over the release rate of the membrane. However, due to the small number of replicates and the large standard deviation of data (approximately 35% of measured data) the results can only be considered qualitative.

Effect of Electrodes Configuration.

Figure 33:
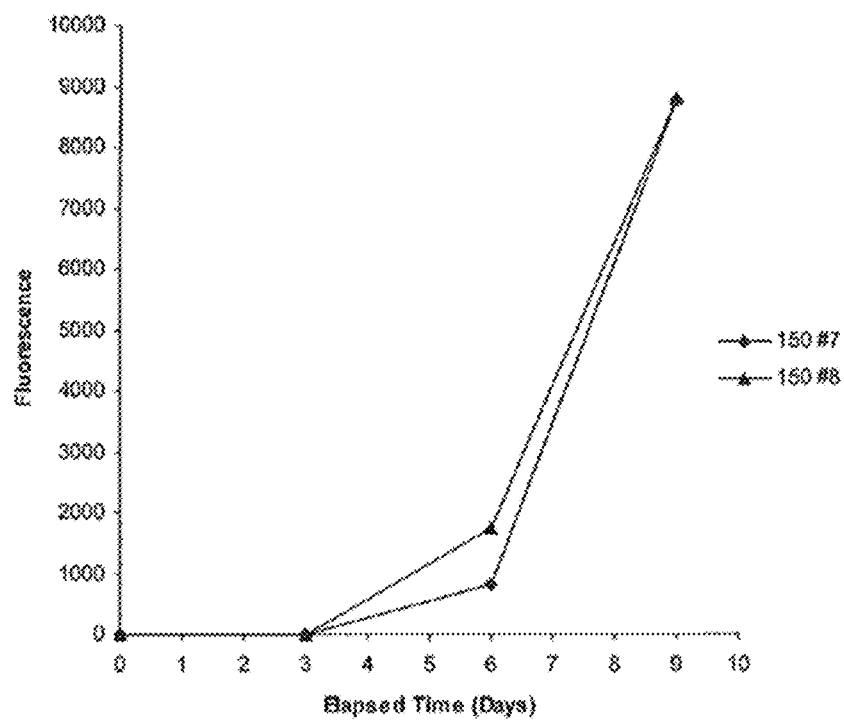

The analysis of the effect of the electrodes configuration over the release rate of BSA-FITC was performed by testing the 1.8 Volts active release of NDDE 150 #7 (electrodes in the inlet and outlet area) and NDDE 150 #8 (electrodes in the microchannels). The results (over a period of 9 days) are shown in FIG. 33. No significant difference in the cumulative results was measured. The release seems not to be affected by different electrode configuration. Due to the small number of replicates and the large standard deviation of data (approximately 40% of measured data) the results can only be considered qualitative.

4.4.2 Test 3. Electro-Osmotic Transport of Glucose 4.4.2.1 Test 3. Objectives

The goal of this test is to demonstrate the EO transport by employing a nominally uncharged molecule such as glucose. In order to perform this test, 6 NDDE 50 #1 membranes were selected. To compare the active release with the passive release, 3 NDDE #1 50 were selected from a different wafer which did not present electrodes. All of the membranes were selected through optical microscopy. Gas testing for configuration #1 showed that the gas flow was too small to reliably measure.

Each membrane was fixed into the basket setups used in other EO testing. For the membranes receiving an applied voltage, each basket held 0.8 mL of a 4M glucose solution. Their respective wells held 1.6 mL of Dl H$_2$O+0.05% wt sodium azide. For the passively releasing membranes, each basket held 1 ml of a 4M glucose solution. Their respective wells held 2 mL of Dl H2O+0.05% wt sodium azide. Every few days, two 1 uL samples from each well were read with a glucose meter. 5 uL of Dl H$_2$O were added back for every day that passed between readings to account for evaporation of the solution.

4.4.2.2 Test 3. Results and Discussion

Figure 34:
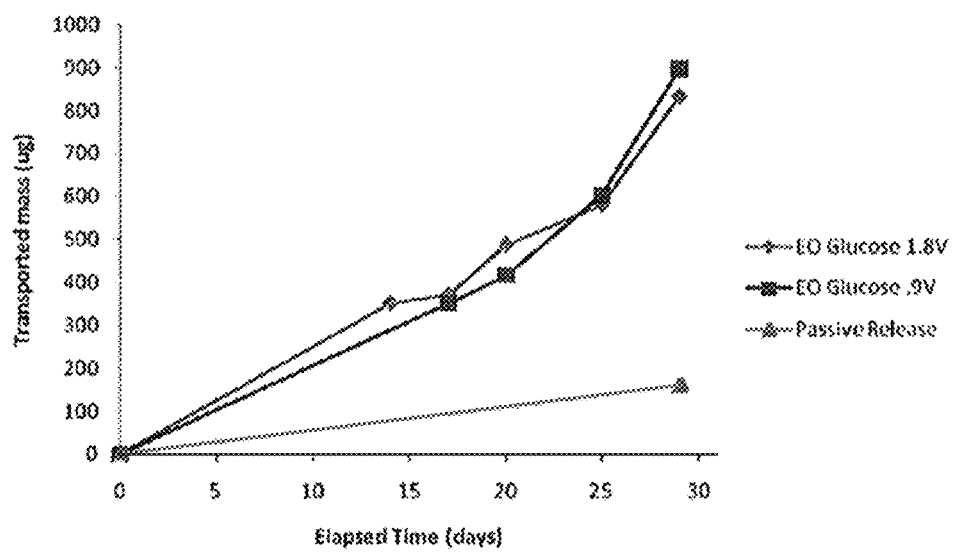
FIG. 34 illustrates a graph indicating glucose released from a nanochannel device over time. Experimental results over 29 days are shown.

FIG. 34 shows the experimental results over 29 days. It is important to note that for the passively releasing membranes, the first measurable concentrations were read on day 54. For this reason, the data points corresponding to data extrapolated from day 54 by hypothesizing a linear cumulative release over time for the membranes. In addition, the membranes used in the passive release experiment came from a different wafer than those used in the active release experiment. They came from a wafer that did not have electrodes on the glass.

The data shows that varying the applied voltage did not significantly influence the release rate of glucose through the membrane. The number of replicates was small, but the difference between the active and passive release amounts was quite large. Thus, qualitatively, the data clearly demonstrates that EO increases the transport rate of glucose through the membrane.

To test the validity of the passive release data for the comparison above, the theoretical release of glucose through was calculated by considering the diffusion, D, as a function of the concentration. This assumption helps to generate equation 6.

$$\dot{M} = 1.557E-6 \cdot \left(\frac{NWH}{L}\right)\left[D_F - \frac{B}{2}(C_{in} - C_{out})\right](C_{in} - C_{out}) \tag{6}$$

$$\dot{M}\left(\frac{\mu g}{day}\right)$$

is the mass flow rate. N is the number of nanochannels. W, H, and L (μm) are the width, height, and length of a single nanochannel. The diffusion constant, $D_F$, is $$6.9E-6\left(\frac{cm^2}{s}\right).$$

The concentration coefficient, B, is $$1.7E-12\left(\frac{cm^2}{s \cdot \mu Molar}\right) \cdot C_{in}(\mu Molar)$$

and $C_{out}$ (μMolar) are 2.75E6 and 0, respectively.

Based on the experimental data at day 54, the amount of glucose passively release was 430 ug. The theoretical amount of glucose released on day 54 was 632.778 ug. The calculations are approximately 30% larger than the experimental results which confirm that the order of magnitude of the passive release is reasonable.

4.4.3 Test 4. V-I Characteristic Curves

The electroosmotic flow generated by the applied electrical field consists in the directional motion of ions along the channels. By applying a difference in electrical potential to the electrodes a current of ions is generated. The current gives an indication of the magnitude of the electroosmotic transport corresponding to the applied voltage. The achievement of the V-I curves associated with the specific membrane configuration allows to design the control of the active transport. The investigation of the V-I curves allows to determine important parameters such as the stability of the electrodes over time.

4.4.3.1 Test 4. Material and Methods

One membrane for each nanochannel size and each configuration was prepared in same manner as the baskets for the NDDE EO testing (as described in paragraph 4.1.2). After wetting the membranes with ethanol and Dl water (see paragraph 4.2.4) the baskets were filled with 0.8 mL of PBS and placed in 12 well plates. The wells were filled with 1.6 mL of PBS. One membrane at the time was then connected to a power supply (Agilent E3643A) used to apply a constant DC voltage at the electrodes of the membrane. The connected electrodes were located closest to the channel area. A digital multimeter (Agilent 34410A) was connected in series with the membrane to measure the current produced by the ion flow generated by the EO phenomena.

Increasing DC voltage was applied to the membrane following a step profile. The steps included 0.4V, 0.8V, 1.2V, 1.6V and 1.9V. After applying a DC voltage to the membrane, the current was left to equilibrate before to increase the voltage level to the following step value. The current data were collected at 1 minute intervals. Finally the equilibrium points as function of the applied voltage were plot for each NDDE configuration.

4.4.3.2 Test 4. Results and Discussion

Figure 35:
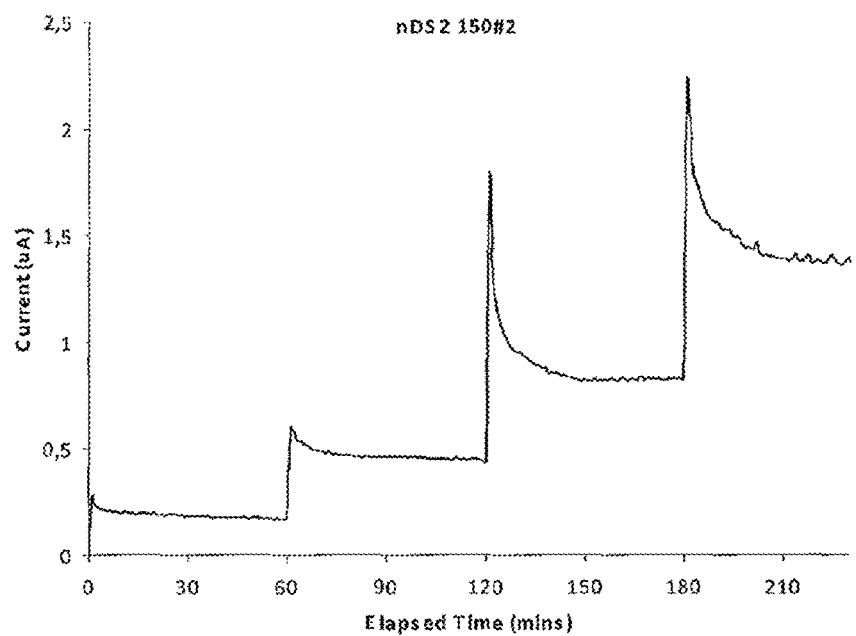
FIGS. 35-36 illustrate current profiles of the DC voltage applied to nanochannel devices over time.

As result of the experimental measurement, a current profile over elapsed time was collected. FIG. 35 shows the collected data for one membrane NDDE 150 #2. The figure shows the current profile at increasing step values of the applied DC voltage. In particular the sequence of steps 0.4 V, 0.8 V, 1.2V and 1.6V is shown. Every time that the voltage level was increased at a higher step a peak was observed in the current profile. The current was then gradually equilibrating at a lower value.

Figure 36:
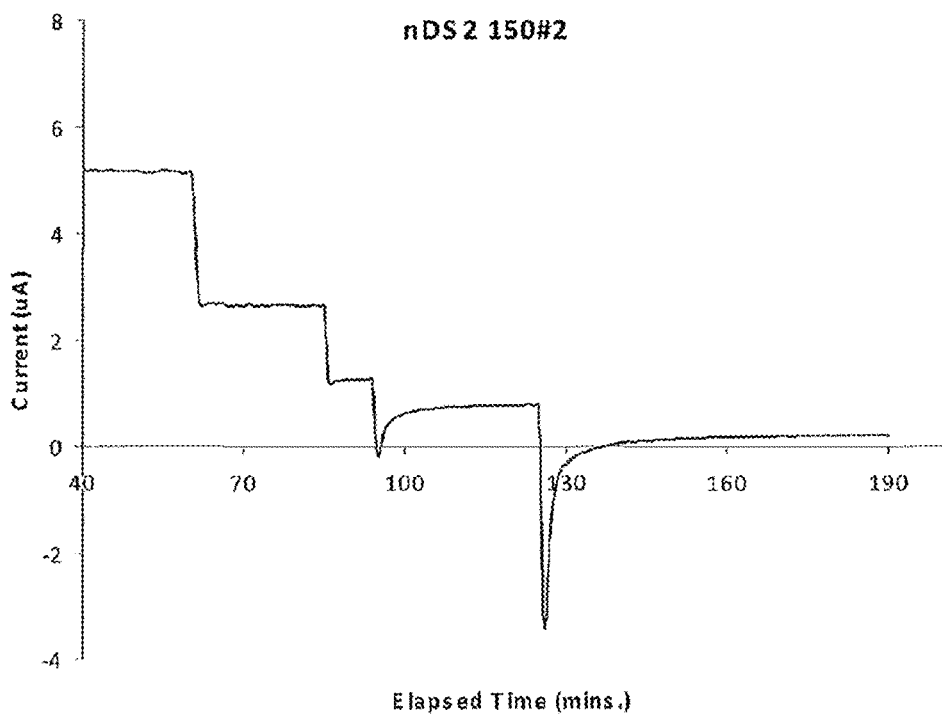

Similar results were observed at reducing applied voltage. In this case by stepping down the level of the voltage, a negative peak was observed in the current profile. FIG. 36 shows the data collected with the NDDE 150 #2 membrane. In this case the reduction of the voltage from 0.8V to 0.4V caused a current drop reaching negative values (or temporary inversion of the current).

Figure 37:
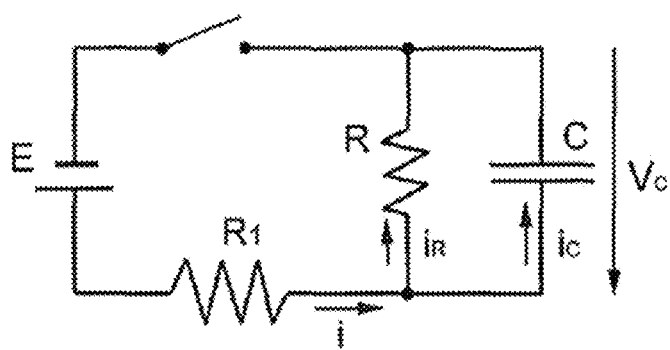
FIG. 37 illustrates a schematic of an electrical circuit used for testing nanochannel devices (schematic of the simplified equivalent model of nDS2).

The behavior shown in FIGS. 35 and 36 is typical of an electrical circuit presenting a parallel between a capacitor and a resistor. FIG. 37 below shows the schematic of the circuit. In the schematic the capacitor represents the electrodes and their ability in accumulating charges. $R_1$ represents the electrical resistance of the electrodes and wiring, R represents the electrical resistance of the fluid.

By instantaneously applying a constant electrical potential E, the voltage at the nodes of the capacitor $V_c$ is equal zero. Thus, at time t=0 the current i is only determined by the resistance $R_1$ of the electrodes. A transient-state follows in which $V_c$ gradually increases determining an exponential reduction of the current i toward a lower steady-state level $$i = \frac{E}{R + R_1} \tag{7}$$

The transient-state presenting a spike in the current and an exponential equilibration happens every time the voltage is instantaneously changed. Positive peaks of current occur at increasing voltage (as shown in FIG. 35), negative peaks of current occurs at reducing voltage (as shown in FIG. 36). The differential equation describing the behavior of the circuit is here derived and the solution calculated.

$$i = i_C + i_R \tag{8}$$

$$V_C = \frac{1}{C} \int i_C dt \tag{9}$$

$$i_R = \frac{V_C}{R} = \frac{1}{RC} \int i_C dt \tag{10}$$

$$i = i_C + i_R = i_C + \int i_C dt \tag{11}$$

$$E = R_1 i + V_c = R_1 i_c + \frac{R_1 + R}{RC} \int i_C dt \tag{12}$$

$$\int i_C dt = (E - R_1 i_c) \frac{RC}{R_1 + R} \tag{13}$$

derivating equation (13), $$i_c = \frac{RC}{R_1 + R} \frac{dE}{dt} - \frac{R_1 R}{R_1 + R} C \frac{di_c}{dt} \tag{14}$$

By applying a constant electrical potential $$E, \frac{dE}{dt} = 0,$$

thus, $$i_c = -R_{eq} C \frac{di_c}{dt}; \text{ where: } R_{eq} = \frac{R_1 R}{R_1 + R} \tag{15}$$

The particular solution of the differential equation (15) is $$i_c = \frac{E}{R_1} e^{\frac{1}{R_{eq} C}} \tag{16}$$

Which is calculated by imposing the boundary conditions:

$$i_c(t = 0) = \frac{E}{R_1} \text{ and } i_c(t = \infty) = 0 \tag{17}$$

The current i(t) is then trivially obtained $$i = i_c + i_r = ic + \frac{V_c}{R} \tag{18}$$

$$V_c = E - R_1 i \tag{19}$$

By introducing (17) and (19) into equation (18) the expression of the current is obtained $$i(t) = \frac{E}{R_1 + R}\left(1 + \frac{R}{R_1} e^{-\frac{1}{R_{eq} C}}\right) \tag{20}$$

The peak of current is obtained at t=0

$$i(t = 0) = \frac{E}{R} \tag{21}$$

The current at steady state is $$i(t = \infty) = \frac{E}{R_1 + R} \tag{22}$$

The analytical solution was calculated for the case of increasing voltage, corresponding to the charging of the capacitor. The solution for the case of decreasing voltage is similarly derived. The simplified model gives an explanation of the positive and negative peaks of current measured during the experimental analysis. The model also describes the increase in the absolute value of the current peak at voltage variation. The model does not take into account a variation of the fluid electrical resistance R.

Figure 38:
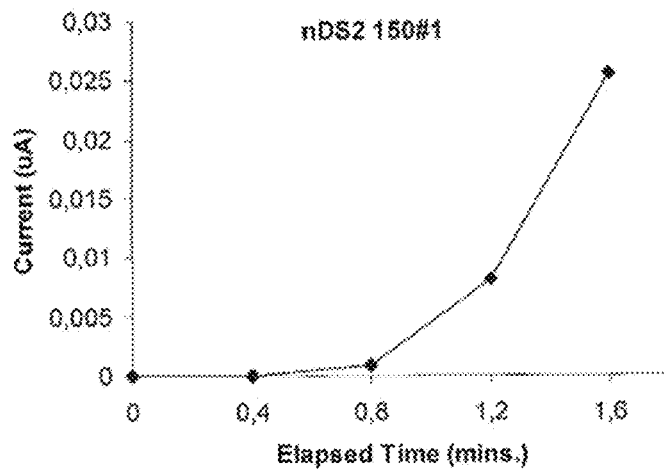
FIGS. 38-39 illustrate current versus voltage graphs generated from the circuit of FIG. 37.
Figure 38:
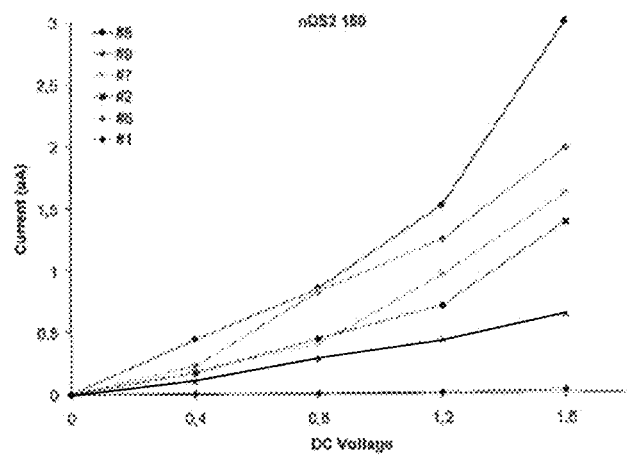

By plotting the current equilibrium points over the applied voltage, the V-1 curve of the membrane was obtained. FIG. 38 shows the V-1 curve for one membrane NDDE 150 #1.

The current exponentially increases with the applied voltage. Similar results were observed for the other tested configurations (NDSE 150 #2, #6, #7, #8, #9).

In FIG. 38 the V-1 curves for the tested membranes are shown. The measured current for all configurations is in the order of magnitude of uA. In this regard NDDE 150 #1 represents an exception displaying current values in the range of 0-30 nA.

The difference in the current value for different membrane is strictly related to the structure of the channel and the configuration of the electrodes. The membranes presenting interdigitated electrodes running on top of each microchannel (configuration #8 and #9) show higher current if compared to configuration presenting electrodes outside the microchannels. In other words, the current depends on the electrical field generated by the difference in potential. It also depends on the number and size of the channels available for the motion of ions. In this regard the membrane NDDE #1 is reasonably showing the smallest values of current, being the number of the nanochannels the smallest among all the other configurations. The V-1 curves help understanding the intensity of the ionic motion from one electrode toward the other. However, there is no direct correlation between the V-1 characteristic curve and the active release of molecules, A clear example is represented by the NDDE configurations 150 #7 and #8. Significant difference was observed between the measured V-1 curves for 150 #7 and #8. However, the active release results (TEST 2) show that, in first analysis, there is a negligible difference in the behavior of the 2 different configurations.

Additional Experimental Results.

Figure 39:
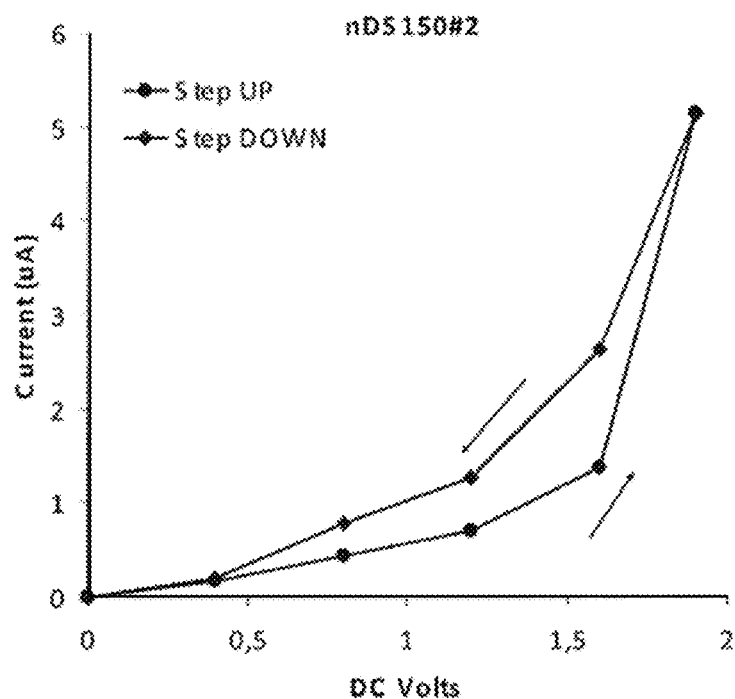

The V-1 curve for increasing and decreasing voltage was measured for the NDDE 150 #2 membrane. FIG. 39 shows the graph representing the measured data. Larger values of current were measured at decreasing voltage. The measurement at decreasing steps was performed right after measuring the increasing steps. Thus, charge accumulation at the electrodes may have caused a temporary increase in the reverse current and thus, the hysteresis effect.

Figure 40:
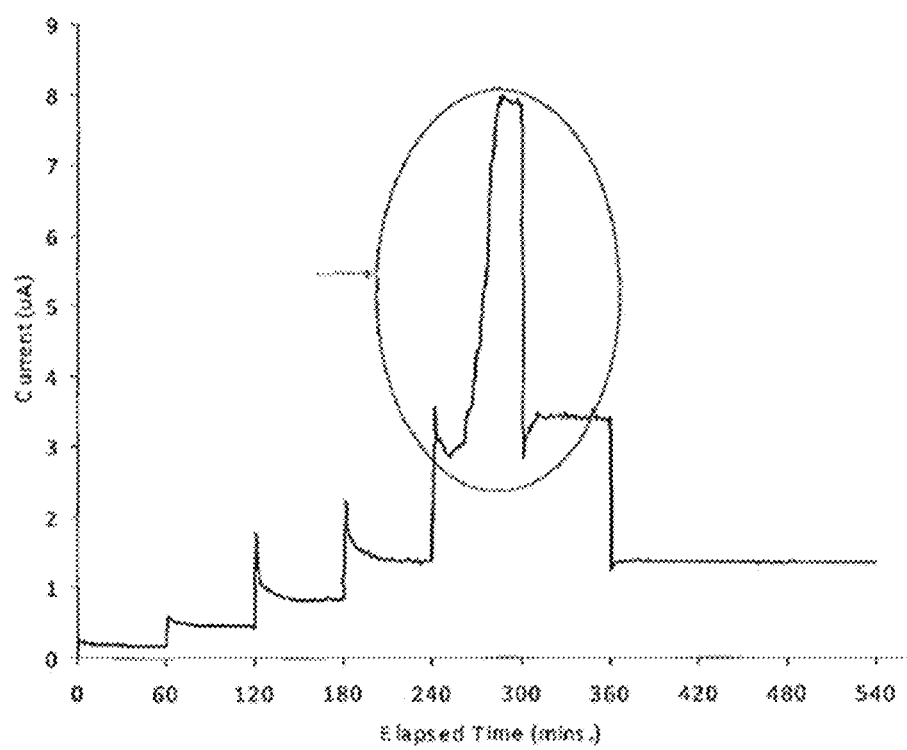
FIG. 40 illustrates a graph of current over time generated from the circuit of FIG. 37. The graph shows a sudden increase in the current at 1.9 VDC (nDS2 150 #2).

While measuring the current at increasing voltage step in some cases a sudden irregular peak in the current was observed. This effect was found to happen at 1.6 or 1.9 Volts. FIG. 40 shows an example of the irregular peak observed for the NDDE 150 #2 membrane. The peak reaches a current value which is double than expected. This effect may be caused by sudden degradation of the superficial layer of the electrodes.

In addition to the preceding design and fabrication techniques, NDD devices can also be designed and fabricated according to methods and apparatus disclosed in U.S. Patent Publication 2007/0066138 ("Diffusion Delivery Systems and Methods of Fabrication") and U.S. Patent Publication 2010/0152699 ("Nanochanneled Device and Method of Fabrication"), incorporated herein by reference.

Flow Field Effect Transistor (FlowFET) Embodiments

Additional exemplary embodiments of the present disclosure provide control of the passive diffusion or the electrokinetic transport of therapeutic components (e.g. drugs) through nanochannels using integrated top and bottom electrodes. Exemplary embodiments may be referred to as double gated Flow Field Effect Transistor (FlowFET).

The zero-order release of biological sourced molecules from nanofluidic membranes has been demonstrated both passively CD. Fine, et al, *Lab Chip,* 2010. 10. 3074-3083) and actively (Fine et al. "A low-voltage electrokinetic nanochannel drug delivery system" *Lab Chip*, submitted). In the case of passive release, the release is zero-order and continuous with a rate that is mechanically determined by the membrane architecture. In the case of active release, the release rate is determined by the electric field applied by electrodes at the inlet and outlet of the nanochannels that induces electroosmosis, electrophoresis, or both. Several prototypes have been developed capable of influencing the active and passive transport of analytes through micro- and nanochannels by modulating the surface charge on one or more of the nanochannel surfaces leading to a change in the zeta potential and by extension the electric double layer that extends into the nanofluidic channel (R. B. M. Schasfoort, et al., *Science,* 1999, 286, 942-945, R. Kamik, et al., *Nano Letters,* 2005, 5, 943-948, R. Karnik, et al., *Appl Phys. Lett.,* 2006, 88, 123114, and C. S. Lee, W. C. Blanchard, and C. T. Wu, *Analytical Chemistry,* 1990, 62, 1550-1552). This modulation leads to either a squeezing of the available cross-section for charged analytes to diffuse or drift through in the nanochannels or influences the induced electroosmotic flow, in some cases reversing it. The implementations which use micro and nanofabricated devices with integrated metallic or semiconducting gates, as opposed to capillary tubes, are referred to as flow field effect transistors (FlowFET). The major drawback of the currently available FlowFETs is that the gate only influences one of surfaces of the nanochannel. This is a problem because the intrinsic zeta potential in neutral pH of silicon dioxide, a material which usually coats the surface of silicon nanochannels, is quite high. Furthermore, the ionic strength of most physiological solutions is also very high leading to very effective charge shielding and very thin Debye lengths. As such, the ability to modulate the surface charge on both the top and bottom of the nanochannel (these two sides make up more than 99% of the total nanochannel perimeter) would be a huge improvement on the current designs and could allow such technology to be extended to drug delivery in highly charged physiological environments. Source and drain electrodes are required in this structure to insure that the surface charge is modulated in the same direction (increased or decreased) for both gate electrodes to maximize the effect. Such a device has an extension in the electronic world in terms of fin field effect transistors (FinFET). One FinFET has source and drain electrodes created on the top and bottom of a thin mesa which is wrapped by the dielectric and gate electrode. This geometry allows the channel to be fully depleted of intrinsic charge, vastly improving the switching speed of the transistor.

A second operational mode which this embodiment would enable, other than DC zeta potential modulation to control diffusion, drift, or DC electroosmosis, is AC coupled traveling wave electroosmosis (A. Ramos, et al. *Proc. SPIE,* 5839. 305-313 and A. Ramos, et al., *J. Appl. Phys.,* 2005, 97. 084906-084906-8). This phenomena occurs when a series of phase shifted AC electrical waveforms are applied to an array of closely spaced electrodes. If properly phase shifted at the right frequency, bulk unidirectional flow can be achieved in microchannels with electrodes on only one surface of the channel. The bulk of the electric field is thus only dropped over a short distance but, through viscous coupling, allows for solution over the whole cross-section of the channel to be moved. Such a system has yet to be implemented at the nanoscale. This could be implemented in nanofluidic membranes by putting a large number of the aforementioned FlowFET double gates in series and applying the appropriate AC potential waveforms.

Figure 41:
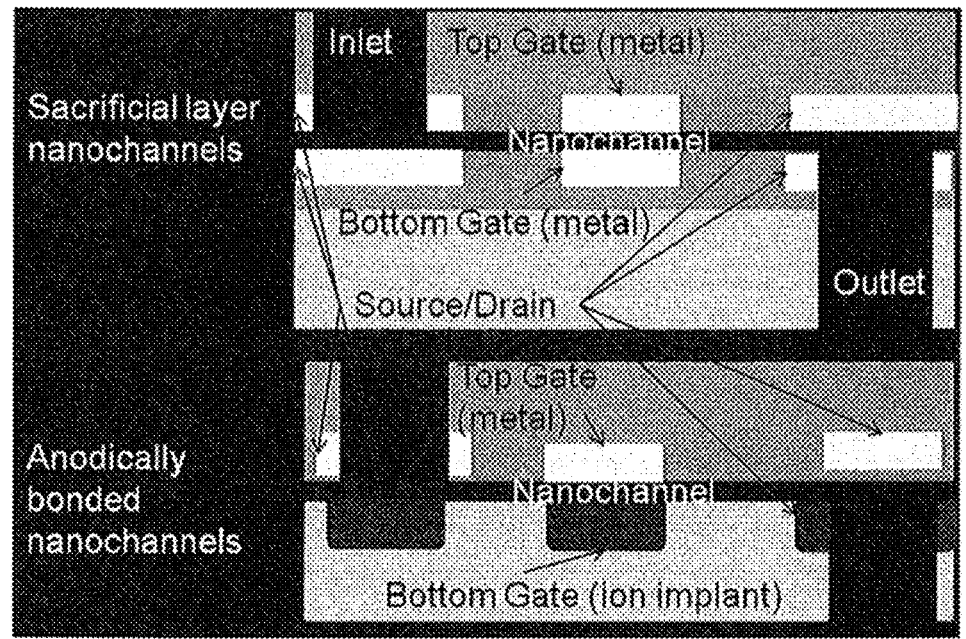
FIGS. 41 and 42 illustrate schematics of a FlowFET device configured for testing nanochannel devices.
Figure 42:
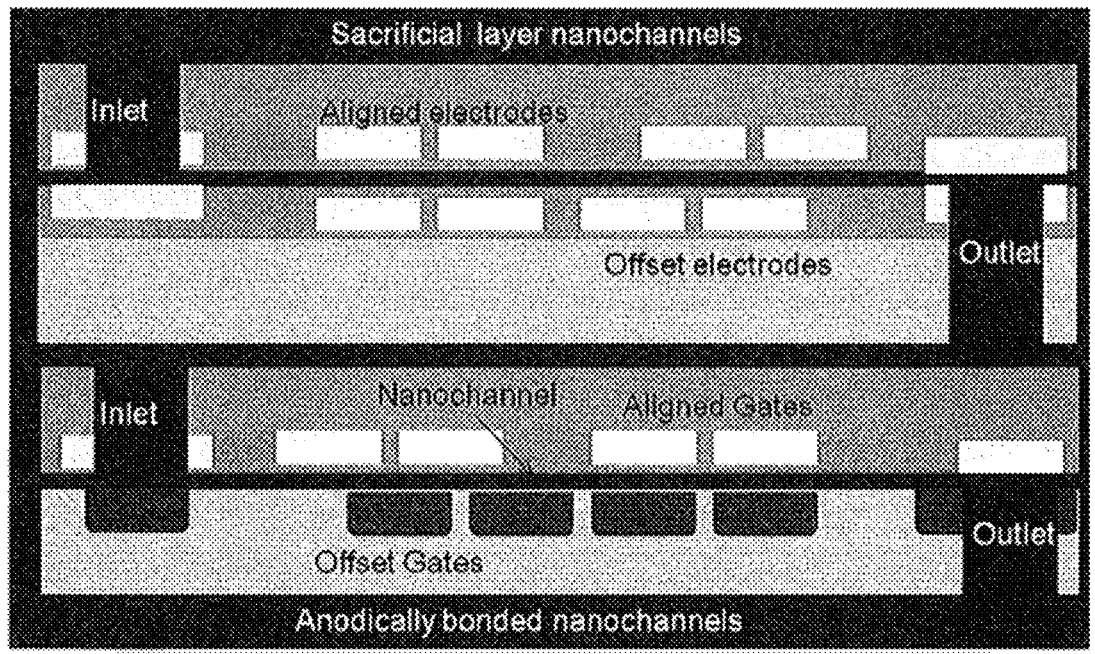

An exemplary embodiment of this device can be seen in FIGS. 41 and 42. The nanochannel membranes that can be used in conjunction with this design are either described in the fabrication procedure at the end of this section or in P. Fine, et al., *Lab Chip,* 2010. 10. 3074-3083 (both anodically bonded nanochannel membranes and nanochannel membranes fabricated with a sacrificial layer technique). Fabrication of the double gated FLowFET or series of FLowFETs for exciting traveling-wave electroosmosis depends on the method of fabrication of the nanofluidic membrane into which it is incorporated. For anodically bonded membranes, the bottom gate and/or source/drain electrodes are ion implanted with a high dose into a high resistivity silicon-on-insulator (SOI) substrate that is covered with a photolithographically patterned ion implant masking layer (preferably with an intrinsic resistivity exceeding 1000 ohm*cm or using isolation oxidation and chemical mechanical polishing (CMP)). The top gate and/or source/drain electrodes are made as follows: trenches are etched into the top Pyrex layer and then filled with Ti/Au or Ti/Pt (although not limited to these metals) to a level higher then the trench. The electrodes are then chemical mechanical polished back to the original Pyrex surface. The fabrication of the membrane is then completed as described in P. Fine, et al. *Lab Chip,* 2010. 10. 3074-3083 with the exception that the anodic bond must be aligned so that the electrodes in the Pyrex will properly align to the nanochannel features in the SOI substrate.

For nanochannels made using a sacrificial metal, the bottom gate and/or source/drain electrodes are first deposited onto the SOI substrate and then patterned, etched, and finally covered with dielectric or other appropriate nanochannel surrounding material. The dielectric is chemical mechanical polished back to the electrode surface followed by the deposition, patterning, and etching of the sacrificial metal which defines the nanochannels once it is removed in a later step. The sacrificial metal is then also coated with dielectric and chemical mechanical polished back to the sacrificial metal surface followed by the deposition, patterning, and etching of the top gate and/or source/drain electrodes. The whole stack is then embedded in the appropriate amount of dielectric or other material. In each CMP step, a thin dielectric can be retained to separate the metal layers if desirable. The process then continues according to P. Fine, et al. *Lab Chip,* 2010, 10, 3074-3083. As the nanochannels are quite thin, electrode width and spacing may have to be quite small as well, sub-micron. Current micro- and nano-fabrication photolithographic capabilities can produce features smaller than 25 nm. Nanoimprint lithography could also be used to produce electrodes as small as 20 nm.

Nanodevice Design and Fabrication (Second Prototype)

The bulk microfabricated nanochannel delivery device (NDD) membranes used in this study consist of a micromachined silicon wafer and a Pyrex cap housing electrodes. The silicon wafer presents an interdigitated finger geometry composed of parallel microchannels connected to each other by an array of perpendicular nanochannels. The top surfaces of the micro- and nanochannels are obtained by anodically bonding the Pyrex capping wafer to a grid of anchor points. The nano-metric dimension of the nanochannels is the depth. As a result of a difference in potential applied to the embedded membrane electrodes, drug molecules enter the membrane through the inlet that is drilled through the Pyrex, move through a set of 136 microchannels, then into a mesh of 120 nanochannels (two sets of 60 on each microchannel), and finally reach the outlet that is wet etched through the silicon wafer through another set of 136 microchannels.

Exemplary embodiments provide the ability to modulate drug release in vivo for both passive diffusion and electrokinetically driven membranes, including completely turning off drug release (e.g. an electrostatic valve), at low power.

Advantages of the double gate structure include allowing for the surface charge to be modulated on more of the nanochannel surface than is possible with current designs, i.e. on one of the FlowFET surfaces. This is important in high ionic strength environments, the case for most physiological environments, or high intrinsic surface charge materials, like silicon dioxide.

In addition to the preceding design and fabrication techniques, NDD devices can also be designed and fabricated according to methods and apparatus disclosed in U.S. Patent Publication 2007/0066138 ("Diffusion Delivery Systems and Methods of Fabrication") and U.S. Patent Publication 2010/0152699 ("Nanochanneled Device and Method of Fabrication"), incorporated herein by reference Exemplary embodiments of the present disclosure also provide passive or active fluid and pressure compensation of an electrokinetic nanochannel implant.

Drug delivery implants are typically constructed of rigid capsules to prevent internally and externally applied stresses from rupturing the drug reservoir leading to catastrophic implant failure. Electrokinetic drug delivery through nanochannel membranes from these rigid bodies can produce fluid flows, and thus pressures, which must be compensated for to prevent the establishment of negative pressure that can prematurely terminate the drug release. Exemplary embodiments of the present disclosure provide methods and structures to compensate this electrokinetically generated fluid flow using a second nanochannel membrane either passively, by means of pressure induced flow, or actively, by means of electrokinetically induced flow.

Figure 43:
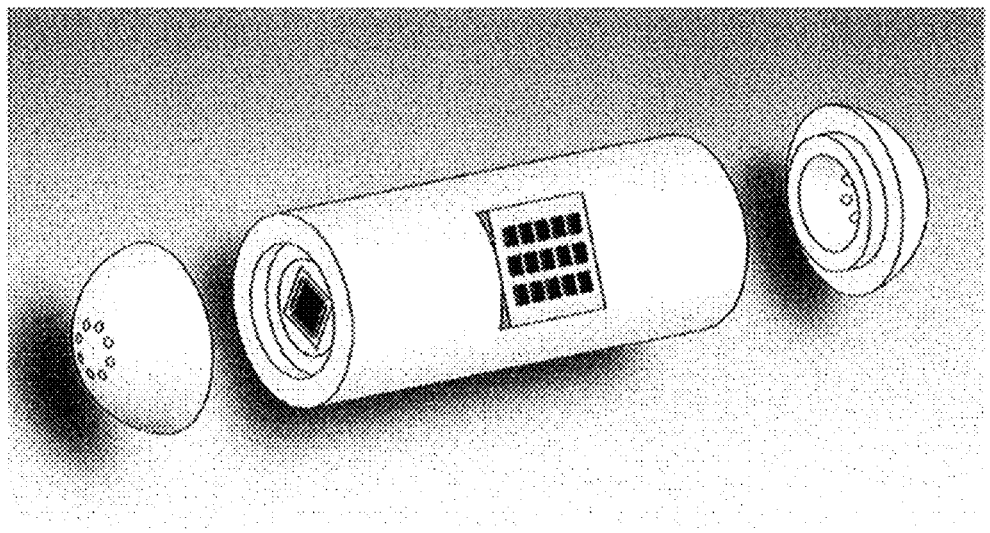
FIGS. 43-45 illustrate a drug delivery implant configured for use with a nanochannel device.
Figure 44:
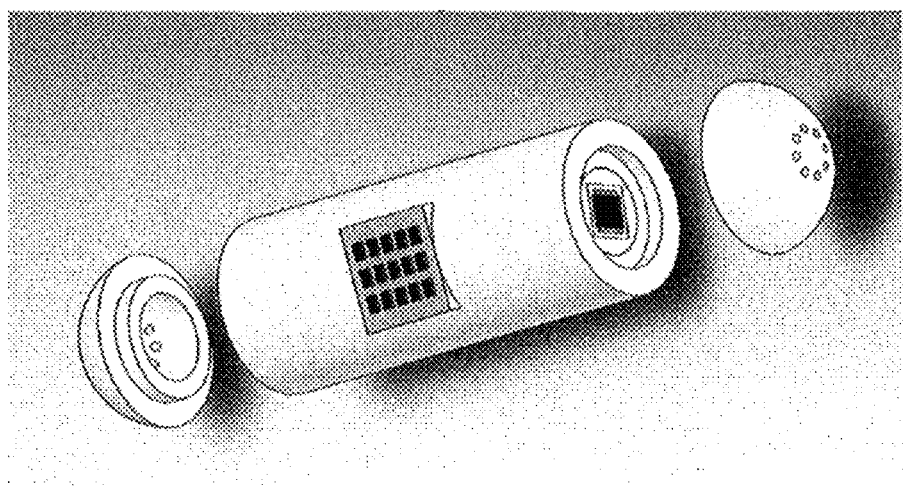
Figure 45:
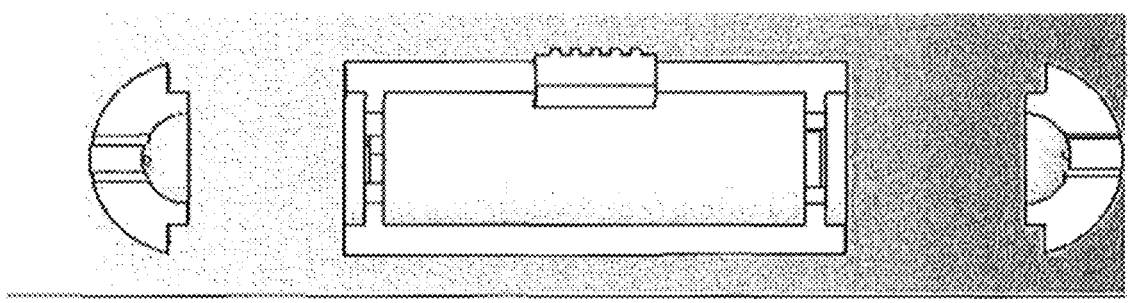

An exemplary illustration of an embodiment can be seen in FIGS. 43, 44 and 45. The nanochannel membranes that can be used in conjunction with this design are either described in the fabrication procedure at the end of this section or in P. Fine, et al., *Lab Chip,* 2010. 10, 3074-3083. The implant architecture consists of strategically placed nanochannel membranes at opposing ends of the implant body. One nanochannel membrane, the delivery membrane, has integrated electrodes to generate an outward electrokinetic flow for delivering drugs. The second nanochannel membrane, the compensation membrane, can be either passive or active and has an inward flow initiated by either the negative pressure induced by the delivery membrane or by active electrokinetically induced flow similar to the delivery membrane. Careful balancing of the total nanochannel cross-section between the delivery membrane and the compensation membrane is required to insure proper compensation and depends on whether the compensation is active or passive. As such, multiple compensation membranes can also be used if necessary. While the delivery membrane is normally selected based on the drug being delivered, the compensation membrane can be selected based many criteria, including the level of protection from an immune response required by the drug as it rests in the reservoir. This consideration is important given the fluid is being drawn into the compensation membrane. A larger number of smaller cross section nanochannels can be used if the payload is highly susceptible to immune markers or proteins such as trypsin. By compensating the fluid flow with physiological fluid, osmotic pressure can also potentially be compensated for.

Nanodevice Design and Fabrication

Second Embodiment

The bulk microfabricated nanochannel membranes (NDS) used in this study consists of a micromachined silicon wafer and a Pyrex cap housing electrodes. The silicon wafer presents an interdigitated finger geometry composed of parallel microchannels connected to each other by an array of perpendicular nanochannels. The top surfaces of the micro- and nanochannels are obtained by anodically bonding the Pyrex capping wafer to a grid of anchor points. The nano-metric dimension of the nanochannels is the depth. As a result of a difference in potential applied to the embedded membrane electrodes, drug molecules enter the membrane through the inlet that is drilled through the Pyrex, move through a set of 136 microchannels, then into a mesh of 120 nanochannels (two sets of 60 on each microchannel), and finally reach the outlet that is wet etched through the silicon wafer through another set of 136 microchannels.

Exemplary embodiments enable electrokinetic drug delivery by properly compensating any induced fluid flows or pressures. Electrokinetic nanochannel drug delivery is a highly controllable process and represents one of the few drug delivery technologies that allows for both analog and digital modulation of drug release.

Prior methods included surrounding the nanochannel membranes or nanoporous frits with deformable membranes. Such an implementation either requires a separate pumping compartment which has a closed pumping reservoir and pushes out drug based on applying pressure to the membrane or a piston or requires a deformable inner liner to be designed into the capsule.

In addition to the preceding design and fabrication techniques, NDD devices can also be designed and fabricated according to methods and apparatus disclosed in U.S. Patent Publication 2007/0066138 ("Diffusion Delivery Systems and Methods of Fabrication") and U.S. Patent Publication 2010/0152699 ("Nanochanneled Device and Method of Fabrication"), incorporated herein by reference.

Exemplary embodiments of the present disclosure also comprise an implantable electrode-coated membrane for actively-controlled drug delivery system, including the structures and methods for manufacturing disclosed in U.S. Patent Publication 2007/0066138 ("Diffusion Delivery Systems and Methods of Fabrication") and U.S. Patent Publication 2010/0152699 ("Nanochanneled Device and Method of Fabrication"), incorporated herein by reference.

Specific exemplary embodiments comprise an implantable robust nanofluidic membrane coated with metallic electrodes (platinum, gold, silver, polysilicon, etc.) in proximity to micro- and nanochannels. The membrane is manufactured using highly precise and accurate silicon nanofabrication techniques. Such a design enables the electrokinetic (electrophoretic, electroosmotic) transport of drugs through nanofluidic channels at low voltage applied directly to the drug solution as it flows through the nanochannels. This implementation allows dramatically increasing and finely tuning the release rate of drugs, as compared to a concentration-driven transport, enabling release rates of clinical relevance.

Exemplary embodiments of the device have been developed to control the release of drugs from an implantable drug reservoir in an actively controlled, dynamic fashion. The application of electric fields using electrodes that are closely integrated to the nanochannels allows for dynamic modulation of drug release at low power. Passive nanochannel membranes can sustain constant zero-order release of drugs for extended periods but cannot be switched or have outputs capable of dynamic control, i.e. the absolute release cannot be modulated nor can the release be switched on and off. The electrode proximity is required to allow for sufficient electric field strength while staying below the potential required causing significant electrolysis. The invented device allows for the modulation, enhancement and fine tuning of the release rate from nanochannel membranes which are already capable of releasing drugs in ranges of therapeutic relevance. Exemplary embodiments include advantages such as dynamic release control, low power, and implant shape flexibility and simple implementation.

Figure 46:
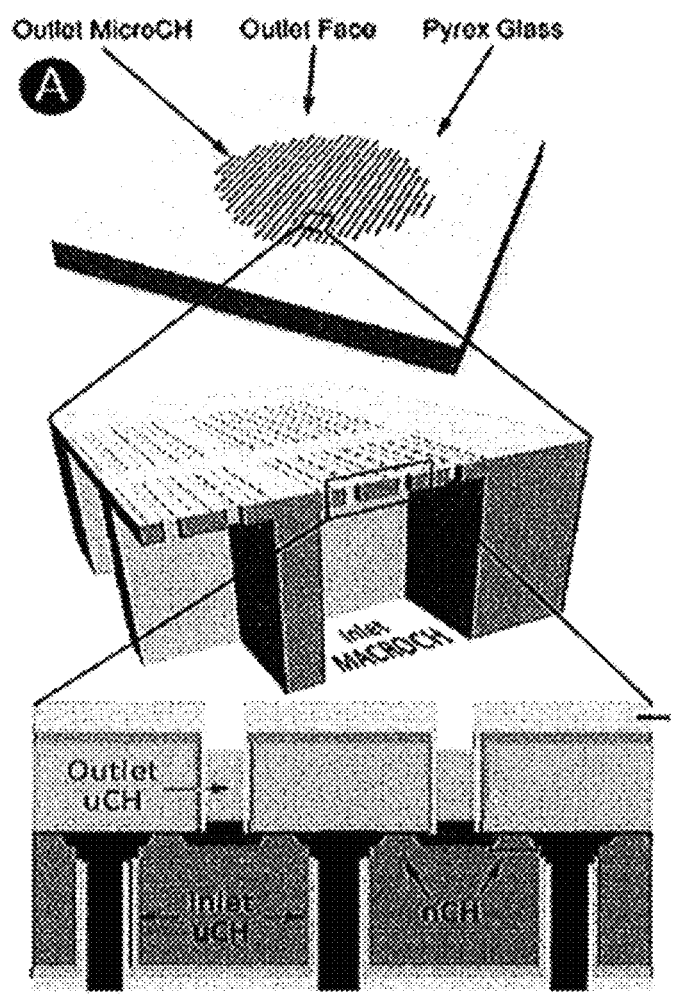
FIG. 46 illustrates a schematic of an electrode-coated nanochannel device and inner structure.

Exemplary embodiments comprise a system for the active and electrokinetic control of drug and particles release from implantable device as described elsewhere in this disclosure. Exemplary embodiments also relate to the coating of the inlet and outlet faces of the passive nanochannel membrane with metal electrodes that can be used for the application of an electrical field across the nanofluidic membrane. Prototypes were fabricated by vacuum evaporation of a titanium layer (10 nm) and a gold layer (100 nm) directly on the silicon and Pyrex surfaces of the passive membrane. FIG. 46 shows schematics of the electrode-coated membrane and its inner structure.

Figure 47:
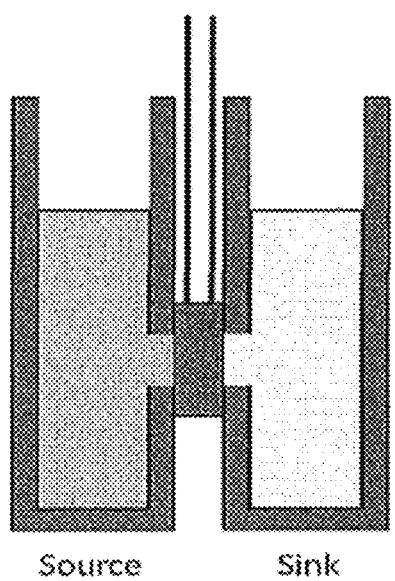
FIG. 47 illustrates the experimental setup for the proof of principle experiments. The wired membrane is glued in between two UV-cuvettes. The cuvettes serve as source and sink reservoirs and allow for the measurement of the molecules or particle release amount by UV absorbance.

By way of demonstration of the invention, experiments were performed with 20 nm nanochannel prototypes. The active control of the release of bovine serum albumin (BSA), 13 nm Qdots and dendritic fullerene (DF1) was measured in a device composed of two UV-cuvettes, placed side by side and clamping the membranes in between. The membrane was epoxied in correspondence of 2 holes drilled on the side walls of the cuvettes. FIG. 47 below shows a schematic of an exemplary embodiment of the device.

Figure 48:
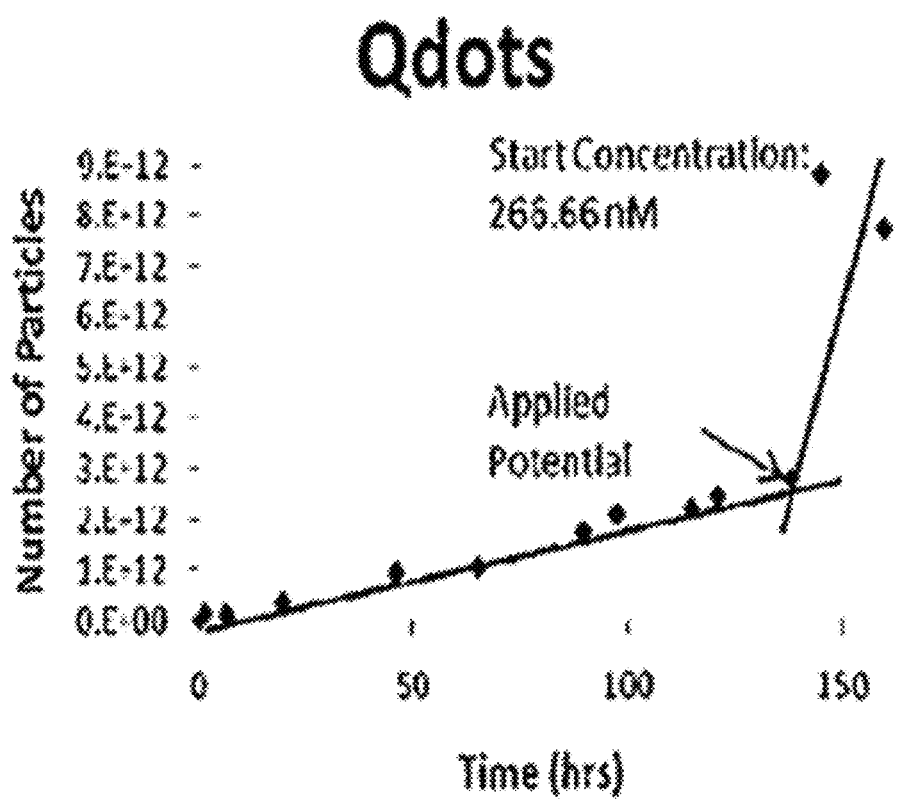
FIGS. 48-50 illustrate experimental results of the active release of Qdots, BSA and DF1 during testing of the device of FIG. 47.
Figure 49:
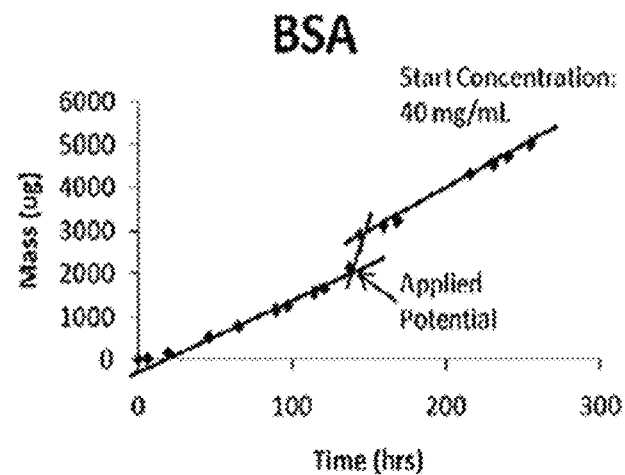
Figure 50:
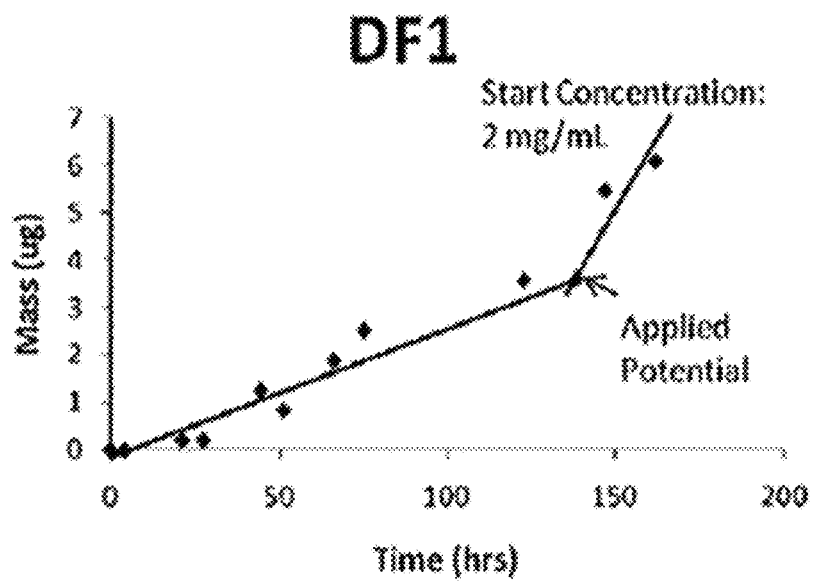

The experimental results of the active release of Qdots, BSA and DF1 are shown in FIGS. 48-50. The graphs show that by applying an electrical potential across the membrane it was possible to significantly enhance the release of molecules and particles.

Exemplary embodiments comprise numerous advantages, including the active electrokinetic control of drug and particle release from implants. In addition, control over the release can be pre-programmed, or remotely controlled. Furthermore, energy consumption is reduced as a result of the efficiency of electroosmosis in nanochannels, and the features can be implemented as a fabrication step of the nanochannel membranes. The electrode-coated membrane can also be integrated in a implantable device. The system may enable long term chronotherapy, and the device can be tuned for electrophoretic or electroosmotic transport of drugs and particles according to needs.

The electrodes can be fabricated in a variety of biocompatible materials including metals (e.g., titanium, platinum, gold), polymers and ceramics. The electrodes can be fabricated in ITO (transparent) to allow for optical quality control. In addition, this technology can be used for the electrokinetic separation of molecules and particles according to molecular/particular charge and size.

REFERENCES

The contents of the following references are incorporated by reference herein: References (each incorporated by reference herein)

[1] F. Martin, R. Walczak, A. Boiarski, M. Cohen, T. Westa, C. Cosentino and M. Ferrari, *J. Controlled Release,* 2005, 102, 123-133.

[2] R. Karnik, K. Castelino and A. Majumdar, *Appl. Phys. Lett.,* 2006, 88, 123114.

[3] W. Sparreboom, A. van den Berg and J. C. T. Eijkel, *Nat. Nanotech.,* 2009, 4, 713-720.

[4] R. B. Schoch and P. Renaud, *Appl. Phys. Lett.,* 2005, 86, 253111.

[5] J. Han and H. G. Craighead, *J. Vac. Sci. Technol. A,* 1999, 17, 2142.
[6] D. Kim, J. D. Posner and J. G. Santiago, *Sensors and Actuators A: Physical,* 2008, 141, 201-212.
[7] M. Z. Bazant, K. Thornton and A. Ajdari, *Phys. Rev. E,* 2004, 70, 021506.
[8] S. J. Kim, Y. C. Wang, J. H. Lee, H. Jang and J. Han, *Phys. Rev. Lett.,* 2007, 99, 044501.
[9] A. Mani, T. A. Zangle and J. G. Santiago, *Langmuir,* 2009, 25, 3898-3908.
[10] T. A. Zangle, A. Mani and J. G. Santiago, *Langmuir,* 2009, 25, 3909-3916.
[11] Q. Pu, J. Yun, H. Temkin and S. Liu, *Nano Lett.,* 2004, 4, 1099-1103.
[12] D. Fine, A. Grattoni, E. Zabre, F. Hussein, M. Ferrari and X. Liu, *Lab Chip,* 2011, 11, 2526-2534.
[13] J. Fu, R. B. Schoch, A. L. Stevens, S. R. Tannenbaum and J. Han, *Nat. Nanotech.,* 2007 2, 121-128.
[14] W. Chu, T. Huen, J. Tu and M. Ferrari, *Proceedings of SPIE,* 1997, 2978, 111.
[15] S. Oleksandrov, J. W. Lee, J. H. Jang, S. Haam and C. H. Chung, *J. of Nanosc. and Nanotech.,* 2009, 9, 1551-1554.
[16] S. M. Kim, M. A. Burns and E. F. Hasselbrink, *Anal. Chem.,* 2006, 78, 4779-4785.
[17] D. Fine, A. Grattoni, S. Hosali, A. Ziemys, E. De Rosa, J. Gill, R. Medema, L. Hudson, M. Kojic, M. Milosevic, L. Brousseau III, R. Goodall, M. Ferrari and X. Liu, *Lab Chip,* 2010, 10, 3074-3083.
[18] A. Grattoni, H. Shen, D. Fine, A. Ziemys, J. S. Gill, L. Hudson, S. Hosali, R. Goodall, X. Liu and M. Ferrari, *Pharm. Res.,* 2011, 28, 292-300.
[19] A. Grattoni, D. Fine, E. Zabre, A. Ziemys, J. Gill, Y. Mackeyev, M. A. Cheney, D. C. Danila, S. Hosali, L. J. Wilson, F. Hussain and M. Ferrari, *ACS Nano,* 2011, 5, 9382-9391.
[20] R. Farra, N. F. Jr. Sheppard, L. McCabe, R. M. Neer, J. M. Anderson, J. T. Jr. Santini, M. J. Cima and R. Langer, *Sci. Transl. Med.,* 2012, 4, 121-122.
[21] M. C. Mormont and F. Levi, *Cancer,* 2003, 97, 155-169.
[22] M. H. Smolensky and N. A. Peppas, *Advance Drug Delivery Reviews,* 2007, 59, 828-851.
[23] C. H. Chen and J. G. Santiago, *J. of Microelectromechanical Systems,* 2002, 11, 672-683.
[24] T. Hoare, J. Santamaria, G. F. Goya, S. Irusta, D. Lin, S. Lau, R. Padera, R. Langer and D. S. Kohane, *Nano Lett.,* 2009, 9, 3651-3657.
[25] M. R. Prausnitz, C. S. Lee, C. H. Liu, J. C. Pang, T. P. Singh, R. Langer, J. C. Weaver, *J. Controlled Release,* 1996, 38, 205-217.
[26] R. B. Schoch, J. Han and P. Renaud, *Rev. Mod. Phys.,* 2008, 80, 839-883.
[27] X. Liu, F. Pu, Y. Fan, X. Deng, D. Li and S. Li, *Am. J. Physiol. Heart Circ. Physiol.,* 2009, 297, H163-H170.
[28] A. Plecis, R. B. Schoch and P. Renaud, *Nano Lett.,* 2005, 5, 1147-1155.
[29] Y. C. Wang, A. L. Stevens and J. Han, *Anal. Chem.,* 2005, 77, 4293-4299.
[30] R. Bakry, R. M. Vallant, M. Najam-ul-Haq, M. Rainer, Z. Szabo, C. W. Huck and G. K. Bonn, *Int. J. Nanomedicine,* 2007, 2, 639-649.
[31] 1. R. S. Kerbel and B. A. Kamen, *Nat Rev Cancer,* 2004, 4, 423-436.
[32] E. Pasquier, M. Kavallaris, and N. Andre, *Nat Rev Clin Oncol,* 2010, 7, 455-465.
[33] M. H. Smolensky and N. A. Peppas, *Advanced Drug Delivery Reviews,* 2007, 59, 828-851.
[34] M. Mormont and F. Levi, *Cancer,* 2003, 97, 155-169.
[35] D. Fine, A. Grattoni, S. Hosali, A. Ziemys, E. De Rosa, J. Gill, R. Medema, L. Hudson, M. Kojic, M. Milosevic, L. Brousseau Iii, R. Goodall, M. Ferrari, and X. Liu, *Lab Chip,* 2010, 10, 3074-3083.
[36] A. Grattoni, H. Shen, D. Fine, A. Ziemys, J. S. Gill, L. Hudson, S. Hosali, R. Goodall, X. Liu, and M. Ferrari, *Pharm. Res,* 2010.
[37] R. Walczak, A. Boiarski, M. Cohen, T. West, K. Melnik, J. Shapiro, S. Sharma, and M. Ferrari, *NanoBioTechnology,* 2005, 1, 35-42.
[38] J. T. Santini, M. J. Cima, and R. Langer, *Nature,* 1999, 397, 335-338.
[39] J. H. Prescott, S. Lipka, S. Baldwin, N. F. Sheppard, J. M. Maloney, J. Coppeta, B. Yomtov, M. A. Staples, and J. T. Santini, *Nat. Biotechnol.,* 2006, 24, 437-438.
[40] R. Karnik, R. Fan, M. Yue, D. Li, P. Yang, and A. Majumdar, *Nano Letters,* 2005, 5, 943-948.
[41] T. Kuo, L. A. Sloan, J. V. Sweedler, and P. W. Bohn, *Langmuir,* 2001, 17, 6298-6303.
[42] S. Pennathur and J. G. Santiago, *Analytical Chemistry,* 2005, 77, 6782-6789.
[43] S. Pennathur and J. G. Santiago, *Analytical Chemistry,* 2005, 77, 6772-6781.
[44] A. Plecis, R. B. Schoch, and P. Renaud, *Nano Lett,* 2005, 5, 1147-1155.
[45] R. B. M. Schasfoort, S. Schlautmann, J. Hendrikse, and A. van den Berg, *Science,* 1999, 286, 942-945.
[46] R. Karnik, K. Castelino, and A. Majumdar, *Appl. Phys. Lett.,* 2006, 88, 123114.
[47] P. von Guggenberg, in *Electrical Insulation and Dielectric Phenomena,* 1993. Annual Report., Conference on, 1993, pp. 122-127.
[48] S. A. Miller, V. Y. Young, and C. R. Martin, *Journal of the American Chemical Society,* 2001, 123, 12335-12342.
[49] C. R. Martin, M. Nishizawa, K. Jirage, M. Kang, and S. B. Lee, *Adv Mater,* 2001, 13, 1351-1362.
[50] L. Sun and R. M. Crooks, *Journal of the American Chemical Society,* 2000, 122, 12340-12345.
[51] C. Duan and A. Majumdar, *Nat Nano,* 2010, 5, 848-852.
[52] S. J. Kim, Y. Wang, J. H. Lee, H. Jang, and J. Han, *Phys Rev Lett,* 2007, 99, 044501-044501.
[53] T. A. Zangle, A. Mani, and J. G. Santiago, *Chem Soc Rev,* 2010, 39, 1014-1035.
[54] A. Plecis, C. Nanteuil, A. Haghiri-Gosnet, and Y. Chen, *Analytical Chemistry,* 2008, 80, 9542-9550.
[55] J. H. Lee and J. Han, *Microfluid Nanofluidics,* 2010, 9, 973-979.
[56] J. Fu, R. B. Schoch, A. L. Stevens, S. R. Tannenbaum, and J. Han, *Nat Nano,* 2007, 2, 121-128.
[57] J. Han, J. Fu, and R. B. Schoch, *Lab Chip,* 2008, 8, 23-33.
[58] J. Han and H. G. Craighead, *Science,* 2000, 288, 1026-1029.
[59] B. R. Cipriany, R. Zhao, P. J. Murphy, S. L. Levy, C. P. Tan, H. G. Craighead, and P. D. Soloway, *Analytical Chemistry,* 2010, 82, 2480-2487.
[60] M. J. Levene, J. Korlach, S. W. Turner, M. Foquet, H. G. Craighead, and W. W. Webb, *Science,* 2003, 299, 682-686.
[61] S. Pennathur, F. Baldessari, J. G. Santiago, M. G. Kattah, J. B. Steinman, and P. J. Utz, *Anal. Chem,* 2007, 79, 8316-8322.
[62] L. Chen, J. Choo, and B. Yan, *Expert Opin Drug Deliv,* 2007, 4, 119-129.
[63] S. Litster, M. E. Suss, and J. G. Santiago, *Sensor Actuat A-Phys,* 2010, 163, 311-314.

[64] S. Bhavaraju, J. Gordon, and A. Joshi, *Drug Delivery Technology,* 2010, 10, 24-31.
[65] P. Apel, *Radiat. Meas.,* 2001, 34, 559-566.
[66] Y. Peng, A. Pallandre, N. T. Tran, and M. Taverna, *Electrophoresis,* 2008, 29, 157-178.
[67] A. D'Emanuele and J. N. Staniforth, *Pharm Res,* 1991, 8, 913-918.
[68] C. A. Haynes and W. Norde, *J. Colloid Interf. Sci.,* 1995, 169, 313-328.
[69] O. Svensson and T. Arnebrant, *J Colloid Interface Sci,* 2010, 344, 44-47.
[70] K. C. Kwok, K. M. Yeung, and N. H. Cheung, *Langmuir,* 2007, 23, 1948-1952.
[71] Y. I. Tarasevich, *Theor. Exp. Chem.,* 2001, 37, 98-102.
[72] T. Maruyama, S. Katoh, M. Nakajima, and H. Nabetani, *Biotechnol. Bioeng,* 2001, 75, 233-238.
[73] W. R. Whitney, *J Phys Chem,* 1903, 7, 190-193.
[74] P. M. Sinha, G. Valco, S. Sharma, X. Liu, and M. Ferrari, *Nanotechnology,* 2004, 15, S585-S589.
[75] G. B. Lesinski, S. Sharma, K. A. Varker, P. Sinha, M. Ferrari, and W. E. Carson, *Biomed. Microdevices,* 2005, 7, 71-79.
[76] D. Marro, Y. N. Kalia, M. B. Delgado-Charro, and R. H. Guy, *Pharm Res,* 2001, 18, 1701-1708.
[77] M. H. Oddy and J. G. Santiago, *J Colloid Interface Sci,* 2004, 269, 192-204.
[78] W. Sparreboom, A. van den Berg, and J. C. Eijkel, *New J Phys,* 12, 1-23.
[79] Ambion, Inc., 2008.
[80] J. H. Knox and K. A. McCormack, *Chromatographia,* 1994, 38, 207-214.
[81] G. J. Sommer, S. M. Kim, R. J. Littrell, and E. F. Hasselbrink, *Lab Chip,* 2007, 7, 898-907.
[82] A. Seiyama, Y. Suzuki, and N. Maeda, *Colloid Polym Sci,* 1993, 271, 63-69.
[83] F. van der Heyden, D. Stein, and C. Dekker, *Phys. Rev. Lett.,* 2005, 95.
[84] G. O. F. Parikesit, A. P. Markesteijn, V. G. Kutchoukov, O. Piciu, A. Bossche, J. Westerweel, Y. Garini, and I. T. Young, *Lab Chip,* 2005, 5, 1067.
[85] P. Ramasamy, R. Elmaghrabi, G. Halada, and M. Rafailovich, *Mater. Res. Soc. Symp. Proc.,* 1061, 1-6.
[86] U. Böhme and U. Scheler, *Chem. Phys. Lett.,* 2007, 435, 342-345.
Santen, R. J., Yue, W., Naftolin, F., Mor, G., Berstein, L. The potential of aromatase inhibitors in breast cancer prevention. *Endocrine-Related Cancer.* 6, 235-243 (1999).
Goss, P. E., Strasser, K. Aromatase Inhibitors in the Treatment and Prevention of Breast Cancer. *J. Clin. Oncol.* 19, 881-894 (2001).
Chlebowski, R. T. Reducing the Risk of Breast Cancer. *N. Engl. J. Med.,* 343, 191-198 (2000).
Dowsett, M., Jones, A., Johnston, S. R., Jacobs, S., Trunet, P., Smith, I. E. In vivo measurement of aromatase inhibition by letrozole (CGS 20267) in postmenopausal patients with breast cancer. *Clin. Cancer Res.* 1, 1511-1515 (1995).
Brueggemeier, R. W., Hackett, J. C., Diaz-Cruz, E. S. Aromatase Inhibitors in the Treatment of Breast Cancer. *Endocrine Reviews* 26, 331-345 (2005).
Coates, A. S., Keshaviah, A., Thürlimann, B., et al. Five years of letrozole compared with tamoxifen as initial adjuvant therapy for postmenopausal women with endocrine-responsive early breast cancer: update of study BIG 1-98. *J. Clin. Oncol.* 25, 486-492 (2007).
Goss, P. E., Ingle, J. N., Martino, S., et al. A randomized trial of letrozole in postmenopausal women after five years of tamoxifen therapy for early-stage breast cancer. *N. Engl. J. Med.* 349, 1793-1802 (2003).
Garreau, J. R., Delamelena, T., Walts, D., Karamlou, K., Johnson, N. Side effects of aromatase inhibitors versus tamoxifen: the patients' perspective. *Am. J. Surg.* 192, 496-8 (2006).
Luthra, R., Kirma, N., Jones, J., Tekmal, R. R. Use of letrozole as a chemopreventive agent in aromatase overexpressing transgenic mice. *The Journal of Steroid Biochemistry and Molecular Biology.* 86, 461-467 (2003).
Harper-Wynne, C., Ross, G., Sacks, N., Salter, J., Nasiri, N., Iqbal, J., A'Hern, R., Dowsett, M. Effects of the aromatase inhibitor letrozole on normal breast epithelial cell proliferation and metabolic indices in postmenopausal women: a pilot study for breast cancer prevention. *Cancer Epidemiol. Biomarkers Prev.* 11, 614-21 (2002).

The invention claimed is:
1. A nanochannel delivery device comprising:
a plurality of inlet microchannels;
a first electrode;
a second electrode;
a plurality of nanochannels; and
a plurality of outlet microchannels, wherein:
each inlet microchannel is in direct fluid communication with an outlet microchannel via a single nanochannel;
the single nanochannel is perpendicular to the inlet microchannel and the outlet microchannel with which it is in direct fluid communication; and
the first electrode is directly coupled to a first surface of the nanochannel delivery device.
2. The nanochannel delivery device of claim 1, wherein the second electrode is directly coupled to a second surface of the nanochannel delivery device.
3. The nanochannel delivery device of claim 2, wherein the second surface is a surface of a first inlet microchannel of the plurality of inlet microchannels, a first outlet microchannel of the plurality of outlet microchannels, or a first nanochannel of the plurality of nanochannels.
4. The nanochannel delivery device of claim 3, wherein the first surface is a surface of the first inlet microchannel, the first outlet microchannel, or the first nanochannel.
5. The nanochannel delivery device of claim 3, wherein the nanochannel delivery device is configured to control a release rate of molecules passing through the first nanochannel by application of a voltage to the first electrode and the second electrode.
6. The nanochannel delivery device of claim 5, wherein the nanochannel delivery device comprises a second nanochannel of the plurality of nanochannels, and wherein application of the voltage to the first electrode and the second electrode does not control a release rate of molecules passing through the second nanochannel.
7. The nanochannel delivery device of claim 3, wherein the first electrode comprises electrically-conductive material deposited on the first surface and the second electrode comprises electrically-conductive material deposited on the second surface.
8. The nanochannel delivery device of claim 1 wherein the nanochannel is oriented parallel to a primary plane of the nanochannel delivery device.
9. The nanochannel delivery device of claim 1 wherein an inlet microchannel of the plurality of inlet microchannels and an outlet microchannel of the plurality of outlet microchannels are in direct fluid communication with a common nanochannel of the plurality of nanochannels.

10. The nanochannel delivery device of claim 1 wherein:
individual inlet and outlet microchannels are arranged perpendicular to a primary plane of the nanochannel delivery device;
the plurality of inlet microchannels form a first array;
the plurality of outlet microchannels form a second array; and
the first array and the second array are overlapping so that individual inlet microchannels are distributed between individual outlet microchannels when viewed along a section taken perpendicular to the primary plane.

11. A nanochannel delivery device comprising:
an inlet channel;
an outlet channel; and
a nanochannel in fluid communication with the inlet channel and the outlet channel, wherein:
the nanochannel comprises a first surface and a second surface, wherein the first surface is substantially parallel to the second surface;
the nanochannel is perpendicular to the inlet channel; and
the nanochannel is perpendicular to the outlet channel;
the first surface and the second surface are electrically conductive.

12. The nanochannel delivery device of claim 11, wherein nanochannel delivery device is configured to control a release rate of molecules passing through the nanochannel by application of a voltage to the first surface and the second surface.

13. The nanochannel delivery device of claim 11 wherein the first surface is electrically coupled to the second surface.

14. The nanochannel delivery device of claim 11 wherein the first surface and the second surface of the nanochannel are separated by a distance that is less than 500 nm.

15. The nanochannel delivery device of claim 11 wherein the first surface and the second surface of the nanochannel are separated by a distance that is less than 100 nm.

16. The nanochannel delivery device of claim 11 wherein the first surface and the second surface of the nanochannel are separated by a distance that is less than 50 nm.

17. The nanochannel delivery device of claim 11 wherein:
the first surface and the second surface of the nanochannel form a first electrode;
the nanochannel delivery device comprises a second electrode; and
at least one of the inlet channel and the outlet channel is between the nanochannel and the second electrode.

18. The nanochannel delivery device of claim 11 wherein the first surface and the second surface of the nanochannel are electrically coupled via a third surface extending substantially perpendicular to the first surface and the second surface of the nanochannel.

19. The nanochannel delivery device of claim 11 wherein during operation a voltage can be applied to the first surface and the second surface and movement of a fluid through the nanochannel can be controlled by varying the voltage.

20. The nanochannel delivery device of claim 11 wherein the nanochannel is in direct fluid communication with the first microchannel and the second microchannel.

21. A nanochannel delivery device comprising:
a first exterior surface and a second exterior surface;
a first electrode and a second electrode;
a nanochannel;
a first microchannel in fluid communication with the nanochannel; and
a second microchannel in fluid communication with the nanochannel, wherein:
the first microchannel extends from the nanochannel to the first exterior surface; the second microchannel extends from the nanochannel to the second exterior surface;
the nanochannel is perpendicular to the first microchannel; and
the nanochannel is perpendicular to the second microchannel channel;
the first electrode and the second electrode extend from the nanochannel to the first exterior surface.

22. The nanochannel delivery device of claim 21, wherein the first electrode is directly coupled to a first surface of the nanochannel.

23. The nanochannel delivery device of claim 21, wherein the second electrode is directly coupled to a second surface of the nanochannel.

24. The nanochannel delivery device of claim 21, wherein the first electrode is directly coupled to a first end of the nanochannel proximal to the first microchannel.

25. The nanochannel delivery device of claim 21, wherein the second electrode is directly coupled to a second end of the nanochannel proximal to the second microchannel.

26. The nanochannel delivery device of claim 21, wherein nanochannel delivery device is configured to control a release rate of molecules passing through the nanochannel by application of a voltage to the first electrode and the second electrode.

27. The nanochannel delivery device of claim 21 wherein the nanochannel delivery device comprises a substantially planar body and wherein the first exterior surface and the second exterior surface are substantially parallel.

28. The nanochannel delivery device of claim 21 wherein the nanochannel is in direct fluid communication with the first microchannel and the second microchannel.

* * * * *